(12) United States Patent
Ahlfors

(10) Patent No.: US 8,043,614 B2
(45) Date of Patent: Oct. 25, 2011

(54) AUTOGENIC LIVING SCAFFOLDS AND LIVING TISSUE MATRICES: METHODS AND USES THEREOF

(76) Inventor: Jan-Eric W. Ahlfors, St John's (AG)

( * ) Notice: Subject to any disclaimer, the term of this patent is extended or adjusted under 35 U.S.C. 154(b) by 388 days.

(21) Appl. No.: 11/077,185

(22) Filed: Mar. 9, 2005

(65) Prior Publication Data

US 2005/0226856 A1   Oct. 13, 2005

Related U.S. Application Data

(60) Provisional application No. 60/551,431, filed on Mar. 9, 2004.

(51) Int. Cl.
*A01N 63/00* (2006.01)
*C12N 5/00* (2006.01)
*C12N 5/071* (2006.01)

(52) U.S. Cl. ...... 424/93.7; 424/93.1; 435/325; 435/366; 435/368

(58) Field of Classification Search ............... None
See application file for complete search history.

(56) References Cited

U.S. PATENT DOCUMENTS

| | | | |
|---|---|---|---|
| 5,135,851 A | 8/1992 | Kajander | 435/34 |
| 5,770,417 A | 6/1998 | Vacanti et al. | 435/180 |
| 6,303,112 B1 * | 10/2001 | Worden | 424/78.06 |
| 6,387,367 B1 | 5/2002 | Davis-Sproul et al. | 424/93.1 |
| 7,175,841 B2 * | 2/2007 | Badylak et al. | 424/93.7 |
| 7,560,276 B2 | 7/2009 | Harmon et al. | |
| 2002/0119180 A1 | 8/2002 | Yelick et al. | 424/426 |
| 2002/0151050 A1 | 10/2002 | Vacanti et al. | 435/325 |
| 2002/0172705 A1 | 11/2002 | Murphy et al. | 424/422 |
| 2002/0182241 A1 | 12/2002 | Borenstein et al. | 424/422 |
| 2003/0003575 A1 | 1/2003 | Vacanti et al. | 435/371 |
| 2003/0059939 A1 * | 3/2003 | Page et al. | 435/366 |
| 2003/0129751 A1 | 7/2003 | Grikscheit et al. | 435/378 |
| 2003/0161817 A1 * | 8/2003 | Young et al. | 424/93.21 |
| 2004/0005297 A1 | 1/2004 | Connelly et al. | 424/93.7 |
| 2004/0033598 A1 | 2/2004 | Vacanti et al. | 435/371 |
| 2004/0057942 A1 | 3/2004 | Vacanti et al. | 424/93.21 |
| 2004/0086497 A1 | 5/2004 | MacLaughlin et al. | 424/93.21 |
| 2004/0101518 A1 | 5/2004 | Vacanti et al. | 424/93.7 |
| 2004/0137613 A1 | 7/2004 | Vacanti et al. | 435/366 |
| 2004/0170612 A1 | 9/2004 | Griffith et al. | 424/93.7 |
| 2004/0175823 A1 | 9/2004 | Vacanti et al. | 435/325 |
| 2004/0219489 A1 | 11/2004 | Yelick et al. | 433/202.1 |
| 2005/0002982 A1 | 1/2005 | Mooney et al. | 424/423 |
| 2006/0018886 A1 * | 1/2006 | Klimanskaya et al. | 424/93.7 |
| 2007/0037283 A1 * | 2/2007 | Patel et al. | 435/380 |

FOREIGN PATENT DOCUMENTS

| | | |
|---|---|---|
| EP | 0282746 | 9/1988 |
| WO | WO 01/49113 | 7/2001 |
| WO | 02/20729 | 3/2002 |

OTHER PUBLICATIONS

Jahan et al 2009 Freshman Engineering Clinic II Spring pp. 1-5.*

Huang et al., 2002; Stress and Strain biomechanical guides for imaging Plaque Stability Chapter 15, pp. 277-286.*
Vacanti et al., "Identification and Initial Characterization of Spore-Like Cells in Adult Manuals," *Journal of Cellular Biochemistry* 80:455-460 (2001).
Levenberg, et al., "Differentiation of human embryonic stem cells on three dimensional polymer scaffolds," Proceed of the National Academy of Sciences 100:12741-12746 (2003).
E. Olavi Kajander, et al, "Nanobacteria from blood, the smallest culturable autonomously replicating agent on Earth", *Proceedings of SPIE*—The International Society for Optical Engineering, vol. 3111, pp. 420-428, May 8, 1998.
Becker, et al., "Regeneration of the Ventricular Myocardium in Amphibians," *Nature*, vol. 248, Mar. 8, 1974, pp. 145-147.
Transwell® Permeable Supports, *Corning Incorporated*, 2006, pp. 1-3.
Therapies, *Spinal Cord Injury—Facts and Figures at a Glance*, 2003, pp. 1-2.
Abe, K., et al., A Comparison of Neurotrophic Effects of Epidermal Growth Factor and Basic Fibroblast Growth Factor in Primary Cultured Neurons from Various Regions of Fetal Rat Brain, Japan. *J. Pharmacol.*, 1990, 54:45-51.
Aguayo, A., et al., Axon-Schwann Cell Relationships in Neuropathies of Mutant Mice, *Annals New York Academy of Sciences*, 1979, pp. 512-531.
Aktas, G. , et al., Ultrastructural Immunolocalization of Basic Fibroblast Growth Factor in Fibroblasts and Extracellular Matrix, *Histochem Cell Biol* (2000), 113:227-233.
Basu, A., et al., Loss of Insulin-Like Growth Factor I Receptor-Dependent Expression of p107 and Cyclin A in Cells that Lack the Extracellular Matrix Protein Secreted Protein Acidic and Rich in Cysteine, *Cell Growth and Differentiation*, 1999, vol. 10, pp. 721-728.
Batchelor, P., et al., CNS Regeneration: Clinical Possibility or Basic Science Fantasy?, *Journal of Clinical Neuroscience*, 2003, 10:523-534.
Bell, E., et al., Production of a Tissue-Like Structure by Contraction of Collagen Lattices by Human Fibroblasts of Different Proliferative Potential in Vitro, *Proc. Natl., Acad. Sci.*, 1979, vol. 76, No. 3, pp. 1274-1278.
Bettger, W., et al., Rapid Clonal Growth and Serial Passage of Human Deploid Fibroblasts in a Lipid-Enriched Synthetic Medium Supplemented with Epidermal Growth Factor, Insulin, and Dexamethasone, *Proc. Natl. Acad. Sci.*, 1981, vol. 78, No. 9, pp. 5588-5592.
Bottaro, D., et al., Molecular Signaling in Bioengineered Tissue Microenvironments, *Ann. N.Y. Acad. Sci.*, 2002, 961:143-153.

(Continued)

*Primary Examiner* — Maria Leavitt
(74) *Attorney, Agent, or Firm* — Nevrivy Patent Law Group P.L.L.C.

(57) ABSTRACT

The present invention is drawn to a 3-dimensional cell-produced scaffold construct comprising fibroblasts and the extracellular matrix that has been produced and arranged by these cells. The constructs promote the differentiation, dedifferentiation and/or transdifferentiation of cells and/or formation of tissue in vitro and in vivo, while at the same time promoting cell growth, proliferation, migration, and acquisition of in vivo-like morphology.

53 Claims, 22 Drawing Sheets

OTHER PUBLICATIONS

Bradshaw, A., et al., SPARC-Null Mice Display Abnormalities in the Dermis Characterized by Decreased Collagen Fibril Diameter and Reduced Tensile Strength, *The Journal of Investigative Dermatology*, 2003, pp. 949-955.

Brenner, K., et al., Regulation of Fibronectin Matrix Assembly by Activated Ras in Transformed Cells, *Oncogene* (2000) 19::3156-3163.

Butt, R., et al., Collagen Production and Replication by Cardiac Fibroblasts is Enhanced in Response to Diverse Classes of Growth Factors, *European Journal of Cell Biology*, 1995, 68:330-335.

Carlson, E. et al., Role of $Cys^{41}$ in the N-Terminal Domain of Lumican in Ex Vivo Collagen Fibrillogenesis by Cultured Corneal Stromal Cells, *Biochem. J.*, (2003) 369:461-468.

Cukierman, E., et al., Cell Interactions with Three-Dimensional Matrices, *Current Opinion in Cell Biology*, 2002, 14:633-639, pp. 633-639.

Dar, A., et al., Optimization of Cardiac Cell Seeding and Distribution in 3D Porous Alginate Scaffolds, *Biotechnology and Bioengineering*, vol. 80, No. 3, Nov. 5, 2002, pp. 305-312.

Edgerton, V., et al., Retraining the Injured Spinal Cord, *Journal of Physiology*, (2001), 533.1, pp. 15-22.

Enrlich, H.P., et al., Cell Locomotion Forces Versus Cell Contraction Forces for Collagen Lattice Contradiction: An In Vitro Model of Wound Contraction, *Tissue and Cell*, 1990, 22:407-417.

Fukumoto, H., et al., Recombinant Human Basic Fibroblast Growth Factor (rhbFGF) Induces Secretion of Nerve Growth Factor (NGF) in Cultured Rat Astroglial Cells, *Neuroscience Letters*, 1991, 122:221-224.

Girton, T.S., et al., Mechanisms of Stiffening and Strengthening in Media-Equivalents Fabricated Using Glycation, *ASME*, 2000, vol. 122, pp. 216-223.

Gospodarowicz, D., et al., Structural Characterization and Biological Functions of Fibroblast Growth Factor, *The Endocrine Society*, 1987, vol. 8, No. 2, pp. 95-109.

Grinnell, F., Fibroblast Biology in Three-Dimensional Collagen Matrices, *TRENDS in Cell Biology*, vol. 13, No. 5, May 2003, pp. 264-269.

Grinnell, F., et al., Collagen Processing, Crosslinking, and Fibril Bundle Assembly in Matrix Produced by Fibroblasts in Long-Term Cultures Supplemental with Ascorbic Acid, *Experimental Cell Research*, 1989, 181:483-491.

Hata. R., et al., L-Ascorbic Acid 2-Phosphate Stimulates Collagen Accumulation, Cell Proliferation, and Formation of a Three-Dimensional Tissuelike Substance by Skin Fibroblasts, *Journal of Cellular Physiology*, 1989, 138:8-16.

Houle, J., et al., Repair of Chronic Spinal Cord Injury, *Experimental Neurology*, 2003, 182:247-260.

Huang, D., et al., Mechanisms and Dynamics of Mechanical Strengthening in Ligament-Equivalent Fibroblast-Populated Collagen Matrices, *Annals of Biomedical Engineering*, 1993, vol. 21, pp. 289-305.

Ishikawa, O., et al., Morphological and Biochemical Analyses on Fibroblasts and Self-Produced Collagens in a Novel Three-Dimensional Culture, *British Journal of Dermatology*, 1997, 136:6-11.

Jin, Y., et al., Transplants of Fibroblasts Genetically Modified to Express BDNF Promote Axonal Regeneration from Supraspinal Neurons Following Chronic Spinal Cord Injury, *Experimental Neurology*, 2002, 177:265-275.

Kessler, D., et al., Fibroblasts in Mechanically Stressed Collogen Lattices Assume a "Synthetic" Phenotype, *The Journal of Biological Chemistry*, vol. 276, No. 39, 2001 pp. 36575-36585.

King, V., et al., Mats Made from Fibronectin Support Oriented Growth of Axons in the Damaged Spinal Cord of the Adult Rat, *Experimental Biology*, 2003, 182:383-398.

Kurata, S., et al., Transcriptional Activation of Type I Collagen Genes by Ascorbic Acid 2-Phosphate in Human Skin Fibroblasts and Its Failure in Cells from a Patient with $\chi_2$(I)-Chain-Defective Ehler-Danlos Syndrome, *Experimental Cell Research*, 1993, 206:63-71.

Kurata, S., et al., Epidermal Growth Factors Inhibits Transcription of Type I Collagen Genes and Production of Type I Collagen in Cultured Human Skin Fibroblasts in the Presence and Absence of L-ascorbic Acid 2-Phosphate, a Long-Acting Vitamin C Derivative, *The Journal of Biological Chemistry*, vol. 266, No. 15, pp. 9997-10003.

Lee, K., Tissue-Engineered Human Living Skin Substitutes: Development and Clinical Application, *Yonsei Medical Journal*, 2000, vol. 41, No. 6, pp. 774-779.

Lu, J., et al., Olfactory Ensheathing Cells Promote Locomotor Recovery After Delayed Transplantation into Transected Spinal Cord, *Brain*, 2002, 125:14-21.

Marusich, M., et al., Hu Neuronal Proteins Are Expressed in Proliferating Neurogenic Cells, *Journal of Neurobiology*, 1994, vol. 25, No. 2, pp. 143-155.

McClain, D., et al., Trolox Inhibits Apoptosis in Irradiated MOLT-4 Lymphocytes, *The FASEB Journal*, vol. 9, 1995, pp. 1345-1354.

Milewski, C, et al., Basic Fibroblast Growth Factor (b-FGF) in der Perimatrix des Cholesteatoms, *HNO*, 1998, 46:804-808 (article in non-English).

Mistry, S., et al., Cultured Rat Hippocampal Neural Progenitors Generate Spontaneously Active Neutral Networks, *PNAS*, Feb 2000, vol. 99, No. 3, pp. 1621-1626.

Ohgoda, O., et al., Fibroblast-Migration in a Wound Model of Ascorbic Acid-Supplemented Three-Dimensional Culture System: the Effects of Cytokines and Malotilate, a New Wound Healing Stimulant, on Cell Migration, *Journal of Dermatological Science*, 1998, 17:123-131.

Parenteau, N., Skin: The First Tissue-Engineered Products, *Scientific American*, Apr. 1999, vol. 280, Issue 4, pp. 1-3.

Pouliot, R., et al., Reconstructed Human Skin Produced in Vitro and Grafted on Athymic Mice, *Transplantation*, vol. 73, 1751-1757, No. 11, Jun. 2002.

Ramshaw, J., et al., Effects of Mesh Modification on the Structure of a Mandrel-Grown Biosynthetic Vascular Prosthesis, *John Wiley & Sons, Inc.*, 1999 pp. 309-315.

Reier, P.J., et al., Intraspinal Transplantation of Embryonic Spinal Cord Tissue in Neonatal and Adult Rats, *The Journal of Comparative Neurology*, 1986, 247:275-296.

Salgo, M., et al., Trolox Inhibits Peroxynitrite-Mediated Oxidative Stress and Apoptosis in Rat Thymocytes, *Archives of Biochemistry and Biophysics*, 1996, vol. 333, No. 2, pp. 482-488.

Sannes, P., et al., Biosynthesis of Sulfated Extracellular Matrices by Alveolar Type II Cells Increases with Time in Culture, *AJP—Lung, Cellular and Molecular Physiology*, 1997, 273:840-847.

Segev, R., Formation of Electrically Active Clusterized Neutral Networks, *American Physical Society*, vol. 90, Issue 16, Apr. 25, 2003, p. 168101; abstract.

Senoo, H., et al., Extracellular Matrix Regulates and L-Ascorbic Acid 2-Phosphate Further Modulates Morphology, Proliferation, and Collagen Synthesis of Perisinusoidal Stellate Cells, *Biochemical and Biophyiscal Research Communications*, 1994, vol. 200, No. 2, pp. 999-1006.

Shipley, R., et al., Multiplication of Swiss 3T3 Cells in a Serum-Free Medium, *Experimental Cell Research*, 1983, 146:249-260.

Takezawa, T., et al., Concept for Organ Engineering: A Reconstruction Method of Rat Liver for in Vitro Culture, *Tissue Engineering*, 2000, vol. 6, No. 6, pp. 641-650.

Tucker, R., et al., Tenascin Expression in the Mouse: In Situ Localization and Induction in Vitro by bFGF, *The Journal of Cell Science*, 1993, 104:69-76.

Tuszynski, M., et al., Spontaneous and Augmented Growth of Axons in the Primate Spinal Cord: Effects of Local Injury and Nerve Growth Factor-Secreting Cell Grafts, *The Journal of Comparative Neurology*, 2002, 449:88-101.

Uysal, A., et al., Comparison of the Biological Activities of High-Density Porous Polyethylene Implants and Oxidized Regenerated Cellulose-Wrapped Diced Cartilage Grafts, *Plastic and Reconstruction Surgery*, 2003, vol. 112, No. 2, pp. 540-546.

Warshamana, G., et al., Dexamethasone Activates Expression of the PDGF-$\chi$ Receptor and Iuduces Lung Fibroblast Proliferation, *The American Physiological Society*, 1998, pp. L499-L507.

Wroemen, M., et al., Adult Neural Progenitor Cell Grafts Survive After Acute Spinal Cord Injury and Integrate Along Axonal Pathways, *European Journal of Neuroscience*, 2003, vol. 18, pp. 743-751.

Ye, Q., et al., Tissue Engineering in Cardiovascular Surgery: New Approach to Develop Completely Human Autologous Tissue, *European Journal of Cardio-Thoracic Surgery*, 2000, 17:449-454.

Yoshii, S., et al., Bridging a Spinal Cord Defect Using Collagen Filament, *SPINE*, vol. 28, No. 20, pp. 2346-2351.

Zhu, Y., et al., Type IIA Procollagen Containing the Cysteine-rich Amino Propeptide is Deposited in the Extracellular Matrix of Prechondrogenic Tissue and Binds to TGF-β1 and BMP-2, *The Journal of Cell Biology*, 1999, vol. 144, No. 5, pp. 1069-1080.

Zoppi, N., et al., Effect of Dexamethasone on the Assembly of the Matrix of Fibronectin and on its Receptors Organization in Ehlers-Danlos Syndrome Skin Fibroblasts, *Cell Biology International*, 1998, vol. 22, No. 7/8, pp. 499-508.

Michel et al. Characterization of a new tissue—engineered human skin equivalent with hair. 1999 In Vitro Cellular & Developmental Biology—Animal, 35:318-328 (1998), Springer, USA.

Paino et al., Induction of axon growth into Schwann celi implants grafted into lesioned adult rat spinal cord. Experimental Neurology, 114(2):254-257 (1991), Elsevier, The Netherlands.

Murakami et al., Transplanted neuronal progenitor cells in a peripheral nerve gap promote nerve repair. Brain Research, 974(1-2)17-24 (Jun. 2003), Elsevier, The Netherlands.

Ahlfors, Jan-Eric, "A Comparative Analysis of the Biomechanics and Biochemistry of Cell—Derived and Cell—Remodeled Matrices: Implications for Wound Healing and Regenerative Medicine," Master's Thesis Defended Apr. 2004, Worcester Polytechnic Institute, USA.

L'Heureux et al., A Completely biological tissue-engineered human blodd vessel. The FASEB Journal, 12(1):47-56 (1996), The Federation of American Societies for Experimental Biology, USA.

\* cited by examiner

US 8,043,614 B2

AUTOGENIC LIVING SCAFFOLDS AND LIVING TISSUE MATRICES: METHODS AND USES THEREOF

CROSS REFERENCE TO RELATED APPLICATIONS

This application is a U.S. regular application from U.S. Provisional Application Ser. No. 60/551,431 filed Mar. 9, 2004, the entire contents of which are hereby incorporated by reference herein.

TECHNICAL FIELD

The present invention relates to "living scaffolds" particularly "autogenic living scaffolds" (ALS), that comprise suitable living cells and the extracellular matrices these living cells produce. The invention also relates to the use of such autogenic living scaffolds as templates and supporting structures for growth of the same cells and tissue or the growth of different cells and different tissue

BACKGROUND ART

In the United States, millions of people are affected by tissue loss every year. Current treatments include tissue transfer from a healthy site in the same or another individual, use of medical devices to support the function of the lost tissue, or pharmacologic supplementation of the metabolic products of the lost tissue. Problems with these current treatments include potential tissue complications and imperfect matches including the possible dependence on immunosuppressants, limited durability of the mechanical devices, and the inconvenience and complexity of pharmacologic supplementation. Current approaches for developing living tissue substitutes make use of a "scaffold" that serves as a physical support and template for cell attachment and tissue development. These scaffolds are ideally designed to resemble, both in structure and composition, the extracellular matrix that the cells are exposed to in vivo, in order to simulate the in vivo conditions. An early and widely used natural scaffold is made of the extracellular matrix protein collagen, while more recently, mechanically stronger artificial scaffolds made of substances such as polyglycolic acid (PGA) and poly-lactic acid (PLA) have been used.

Some cell-scaffold compositions have multiple layers of biocompatible materials including extracellular matrix materials such as collagen, fibril-forming collagen, Matrix Gla protein, osteocalcin, or other biocompatible materials including marine coral, coralline hydroxyapatite ceramic, and mixtures thereof, and some such scaffolds have been seeded with cells, and then placed within a bioreactor having a means for mechanically stimulating the cells at distinct frequencies (see U.S. Patent Application No. 0040005297 to P. R. Connelly et al., filed Jul. 8, 2002, published Jan. 8, 2004).

In addition, living tissue equivalents (LTEs), notably cell-seeded collagen and fibrin gels, have been used extensively as in vitro wound-healing models as well as systems for studying tissue remodeling. More recently, LTEs have begun to gain considerable attention as replacements for lost or damaged connective tissue (e.g., Apligraf™ from Organogenesis, Inc.). LTEs have several advantages over synthetic alternatives including being a natural cell substrate, allowing cellularity to be achieved directly, and being conducive to cell spreading and extracellular matrix (ECM) formation. LTEs are made by mixing cells with a soluble biopolymer solution (e.g., collagen, fibrin, and/or proteoglycans). The cells invade, rearrange and partially degrade the biopolymer scaffold over the next few days as well as synthesize new proteins throughout the culture period. However, LTEs generally lack the physical properties necessary to resist in vivo mechanical forces, and are not true "living tissues".

Over the last two decades, LTEs that are completely cell-derived have been developed. However, to date they have been very thin and taken a long time to grow, generally on the order of months, whereas collagen gels and fibrin gels can be developed in only a few days. There is a need for completely biological cell-derived LTEs, and living scaffolds for use in wound repair and tissue regeneration in vitro and in vivo.

SUMMARY OF THE INVENTION

Embodiments of the presently claimed invention provide a strong, thick, cell-produced living tissue equivalent (LTE), comprising cells and ECM produced by these cells (this ECM is called cell-produced matrix or cell-derived matrix (CDM)), that can be developed in only three weeks for use in creating strong and completely biological soft connective tissue substitutes and for examining wound-healing and tissue development in vitro. The biomechanics and corresponding biochemical composition of cell-produced and cell-remodeled matrices are also provided, as are chemically-defined media permissive to the self-production of extracellular matrix (ECM) by cells.

Other embodiments disclose placing fibroblasts in conditions that are conducive to the rapid production of extracellular matrix without an exogenous scaffold, which results in a significantly stronger and thicker 3-D construct than can be obtained with cell-remodeled matrices, such as fibroblast-populated collagen and fibrin gels.

Thus, embodiments of the presently claimed invention provide the use of autogenic living scaffolds, cell produced matrices (also referred to as cell-derived matrices (CDMs), and living tissue matrices (LTMs) made entirely of living cells and the extracellular matrices they produce in vitro, to promote differentiation, dedifferentiation and/or transdifferentiation of cells and formation of tissue in vitro and in vivo, while at the same time promoting cell growth, proliferation, migration and/or acquisition of in vivo-like morphology, none of which has been reported to date.

Embodiments in accordance with the presently claimed invention provide an autogenic living scaffold (ALS) or living tissue matrix (LTM) that is a cell-produced scaffold which provides mechanical, nutritional and/or developmental support for cells, tissues, organs, or combinations thereof. The cell-produced autogenic living scaffold as herein disclosed is smart, such that it is capable of adjusting to its environment, and it is living, whereby it is biologically active and all components except seeded cells and tissue are naturally formed by the scaffold system itself, making the scaffold autogenic, or self-produced.

The Autogenic Living Scaffolds as disclosed herein are made by and comprise living cells and the extracellular matrix (ECM) that the living cells produce. The living cells may be genetically engineered or otherwise modified. The ALS serves as a blueprint, supporting structure, backbone, or scaffold for the same or other cell lines or types. The ALS may also provide proper or supporting mechanical and chemical environments, signals, or stimuli to other cells, to the cells that produce the ALS, to surrounding tissue at an implantation site, to a wound, or for in vitro generation and regeneration of cells, tissue and organs. The ALS may also provide other cells with nutrients, growth factors, and other necessary or useful components, may take in or serve as buffers for certain substances in the environment, and have the potential to adapt to new environments.

The cells of an Autogenic Living Scaffold may also be used to produce tissue and/or organs such as cardiac muscle, when seeded with cells or tissue of interest. For example, liver tissue may be produced from an ALS that is seeded with hepatocytes; and kidney, pancreas, spinal cord, and other organs and tissues of the body may also be produced by seeding the ALS with the desired cell or tissue type. Autogenic Living Scaffolds seeded with the appropriate cell types may thus be used to grow implantable tissue and organs in vitro, for later implantation into an in vivo site.

Many different types of cells may also be seeded in different parts of the Living Scaffold, or they could be sandwiched on top of each other. For example, a Fibroblast Autogenic Living Scaffold may first be grown in serum-free conditions favorable to the growth of the fibroblasts into tissue or an Autogenic Living Scaffold. This Living Scaffold is then seeded with astrocytes, and the serum-free growth conditions (including the media, pH, osmolarity, temperature, oxygen tension, and anything else required) are adjusted to be favorable to the growth of the astrocytes. If needed, other components are added to keep the Living Scaffold alive and healthy. Also, additional layers, such as skeletal muscle myocytes that might form into skeletal muscle tissue that is innervated by the already seeded nerves, may continue to be added, as desired.

In another embodiment, the Autogenic Living Scaffold may also be grown into specific shapes by molds, and may also be reshaped to some degree. For example, a sheet of the above example of a Fibroblast Autogenic Living Scaffold, seeded first with astrocytes and then nerve cells, may be rolled into a cylinder. This cylinder may then be implanted into a spinal cord in vivo. The Autogenic Living Scaffold also provides mechanical support to the seeded cells. For example, in a particular embodiment, a Fibroblast Autogenic Living Scaffold seeded with neurons may be mechanically stressed and compressed, without major damage to the neurons, even though such a degree of mechanical stress and compression kills most neurons when grown in the absence of an ALS. The Autogenic Living Scaffold of other embodiments may also be introduced to mechanical stress or tension which may change the properties of the Living Scaffold and any cells or tissue that are growing on it.

In one particular embodiment, the fibers of a Fibroblast Autogenic Living Scaffold may also be made to grow in parallel, which helps seeded nerve cells to also grown in parallel along these fibers, especially when Schwann cells are previously seeded onto the scaffolds and first start growing in parallel along these fibers. This may be even more useful when implanted in the spinal cord, since the implanted nerve cells may then be aligned in the same direction as the native nerve cells in the spinal cord. In still another embodiment, a sheet of Autogenic Living Scaffold with the seeded neurons may also be rolled into a cylinder prior to implantation to produce a structure with layers of neurons aligned in the same general direction as the native neurons in the spinal cord. Similar things may be done for implantation into other tissues and organs.

In other particular embodiments, cell to cell, tissue to tissue, and tissue to cell interactions may also be studied in vitro and in vivo with Autogenic Living Scaffolds, including by sandwiching different cells. In yet another embodiment, Autogenic Living Scaffolds may be used as in vitro biological models for studying the growth and development of cells, tissues, organs, systems, diseases, and different responses in organisms. For example, the wound response (in which fibroblasts play an active role) on different types of cells and tissues may be studied in vitro by using this technology.

Fibroblasts (especially foreskin fibroblasts) secrete numerous growth factors including nerve growth factor (NGF), brain-derived neurotrophic factor (BDNF), and neurotrophin-3 (NT-3), as well as fibroblast growth factor (FGF), and platelet-derived growth factor (PDGF), all of which promote neuron regeneration and survival. The embodiments of ALSs described herein more closely mimic the extracellular environment that nerve cells are normally exposed to in vivo than any other currently available scaffolds, and even allow primary nerve cells to form active 3-D neural networks in vitro that can serve as in vitro 3-D models for potential therapeutic agents for neuronal regeneration, as may also be used to functionally replace injured spinal cord neurons in vivo.

In the case of particular embodiments of fALS of the present application, the high density of fibroblasts along with the insoluble ECM proteins collagen and fibronectin of the ALS work in conjunction to promote axon elongation and functional recovery when implanted into chronically injured spinal cord. In addition, the development of a functional neural network in vitro allows the nerve graft to have more utility when implanted, and is important for studying the effect of different pharmacological agents and methods on the in vitro 3-D neural network model disclosed herein.

In other embodiments the effects of different nutritional supplements and growth factors on the development of the functional neural networks in the ALS may also be studied. Thus, in embodiments of the present invention, once the neurons are seeded onto the ALS, the growth media is changed from one that supports ALS growth to one that promotes neuronal growth and differentiation, while at the same time retards the growth of fibroblasts. This prevents the fibroblasts from over-running the neurons and effectively preventing neuronal development. In other embodiments, the fibroblasts may be genetically engineered to secrete more growth factors such as NGF, BDNF, FGF-2, and bFGF to enhance neuron survival and development even further.

In still other embodiments, the ALS nerve graft has the flexibility of taking on almost any non-rigid shape and may be rolled up into a ball or cylinder. Several thin nerve grafts may also be layered on top of each other to form different parallel layers of neural networks, which in turn may again be rolled up into a cylinder or formed into some other shape.

Another embodiment provides an autogenic living scaffold that has been seeded with cells, tissue or combinations thereof, including any of stem cells, progenitor cells, precursor cells; cells or tissue of a connective, epithelial, muscle, nerve and/or glandular origin; and cells of vascular and/or non-vascular organ origin such as neuroblastomas, myoblasts, astrocytes, cardiomyocytes, skeletal muscle myoblasts, hepatocytes, chondrocytes, osteoblasts, fibroblasts, keratinocytes, Schwann cells, nerve cells, glial cells, epithelial cells, endothelial cells, smooth muscle cells, skeletal muscle cells, cardiac muscle cells, stromal cells, mesangial cells, mesenchymal cells, hematopoietic cells, dendritic cells, immune system cells, neural tissue, hepatic tissue, aortic tissue, venous tissue, capillary tissue, cartilage, bone, muscle, glands, and hair follicles.

Another embodiment provides a Living Tissue Matrix (LTM) that closely resembles in vivo generative/regenerative connective tissue since the cells produce the entire 3D matrix by themselves. In fact, LTMs are similar in composition to the type of fibroblast-populated connective tissue that first fills the wound bed in embryonic wound healing (and other non-scar forming tissue wound healing) that regenerates without scarring as opposed to wounds in neonatal or adult mammals that heal with scarring. Furthermore, this method produces a 3-D construct (the LTM) that is significantly thicker and stronger than those obtained using biopolymer gels, such as collagen or fibrin gels. The entire Living Tissue Matrix (cells and ECM) can also be made completely autologous, thus preventing host rejection and making it completely immunocompatible.

In another embodiment, the ECM produced in the LTM system provides an optimal environment for de-differentiated or transdifferentiated autologous adult cells within the LTMs to create a regenerative environment and a virtual blastema. In other words, if the millions of fibroblasts within the LTM (the cells that produced the LTM in the first place) are de-differentiated or transdifferentiated, the LTM can effectively become a structurally sound implantable blastema-like structure for multi-tissue type regeneration.

Another embodiment provides a chemically defined media formulation (called "fALS Media" or "Matrix Media") for growing an ALS or LTM that contains a 3:1 ratio of DMEM (high glucose—4.5 g/L—with L-glutamine and sodium pyruvate) and Ham's F12 medium (or 2:1 ratio of IMEM to Ham's F12 medium), supplemented with $4.2 \times 10^{-10}$M Epidermal Growth Factor (in human serum albumin); $2.8 \times^{-10}$M Basic Fibroblast Growth Factor; $8.6 \times 10^{-5}$M insulin; $1.0 \times 10^{-7}$M dexamethasone; $3.2 \times 10^{-4}$M L-ascorbic acid phosphate magnesium salt n-hydrate; $2 \times 10^{-10}$M L-3,3',5-triiodothyronine; $4 \times 10^{-10}$M ethanolamine or other lipid precursor; $3.9 \times 10^{-8}$M selenious acid; $4 \times 10^{-3}$M L-analyl-L-glutamine; $3.3 \times 10^{-6}$M glutathione (reduced); and 1% penicillin/streptomycin/amphotericin B. In addition, other embodiments and variations of the above-listed medium may contain additional components, such as any one or more of: Platelet Derived Growth factor (PDGF); 100:68 ratio of glycine:L-proline; L-cysteine; and 6-hydroxy-2,5,7,8-tetramethychroman-2-coarboxylic acid ("TROLOX™"). Concentrations may vary as required, as long as the total osmolarity in the medium is kept at acceptable levels for growth of the ALS.

Other embodiments provide methods for growing tissue and/or organs using an ALS or LTM, and methods for using an ALS or LTM to model a human biological cellular system or tissue system of a combination thereof. In addition, methods are provided for using an ALS or LTM to assess the effect of one or more agents on a biological system being modeled, wherein one or more agents includes pharmaceutical agents, enzymes, hormones, small molecules, peptides, polypeptides, natural products, natural products extracts, inorganic salts, other cells, growth factors, clotting factors, toxins, poisons, nucleic acids, mechanical stress inducers, electrical current generators, electromagnetic field and pulse generators, and sonic wave inducers.

Still other embodiments provide methods for using an ALS or LTM to treat tissue or organ damage or tissue or organ degeneration in a subject suffering from Crohn's disease; cancer, including lung, colon, stomach, liver, kidney, pancreas, bone, brain; muscular dystrophy; ocular degeneration, diabetes, cardiac ischemia; heart valve damage or heart valve congenital defect comprising producing an ALS or LTM, and any one of a) regenerating a new organ or tissue of the tissue in vitro using the scaffold and cells or tissue of the type or class of the damaged or degenerated tissue or organ and then implanting such scaffold with regenerated tissue or tissue of the organ in the subject at the site of tissue or organ damage or degeneration; or b) implanting the scaffold and cells or tissue of the type or class of the damaged or degenerated tissue or organ in the subject at the site of tissue or organ damage or degeneration and then regenerating a new organ or tissue of the organ in vivo using the scaffold having cells or tissue of the type or class of the damaged or degenerated tissue or organ; or c) regenerating a new organ or tissue of the organ as in a) or b) using the scaffold alone.

Other embodiments provide methods for using an ALS to generate viable vertebrate neuronal tissue in vitro comprising seeding an ALS with vertebrate primary neural cells or neuronal tissue and maintaining the seed scaffold in culture under conditions where viable vertebrate neuronal tissue is generated. Such viable vertebrate neuronal tissue is then used in other embodiments to treat paralysis in a subject by contacting at least one site of spinal cord in the subject with an effect amount of the ALS with viable neuronal tissue so as to treat the paralysis.

Similarly, other embodiments provide methods for treating a neurodegenerative disease in a subject, wherein the neurodegenerative disease is any one of Parkinson's disease, Huntington's disease, Alzheimer's disease, schizophrenia, dementia, multiple sclerosis, cerebral palsy, muscular dystrophy, Tay Sach's disease, Mad Cow disease, or Creutzfield-Jacob's disease, by contacting at least one site in the subject with an effective amount of an ALS or LTM with viable neuronal tissue so as to treat the neurodegenerative disease.

DETAILED DESCRIPTION OF SPECIFIC EMBODIMENTS

Figure 1:
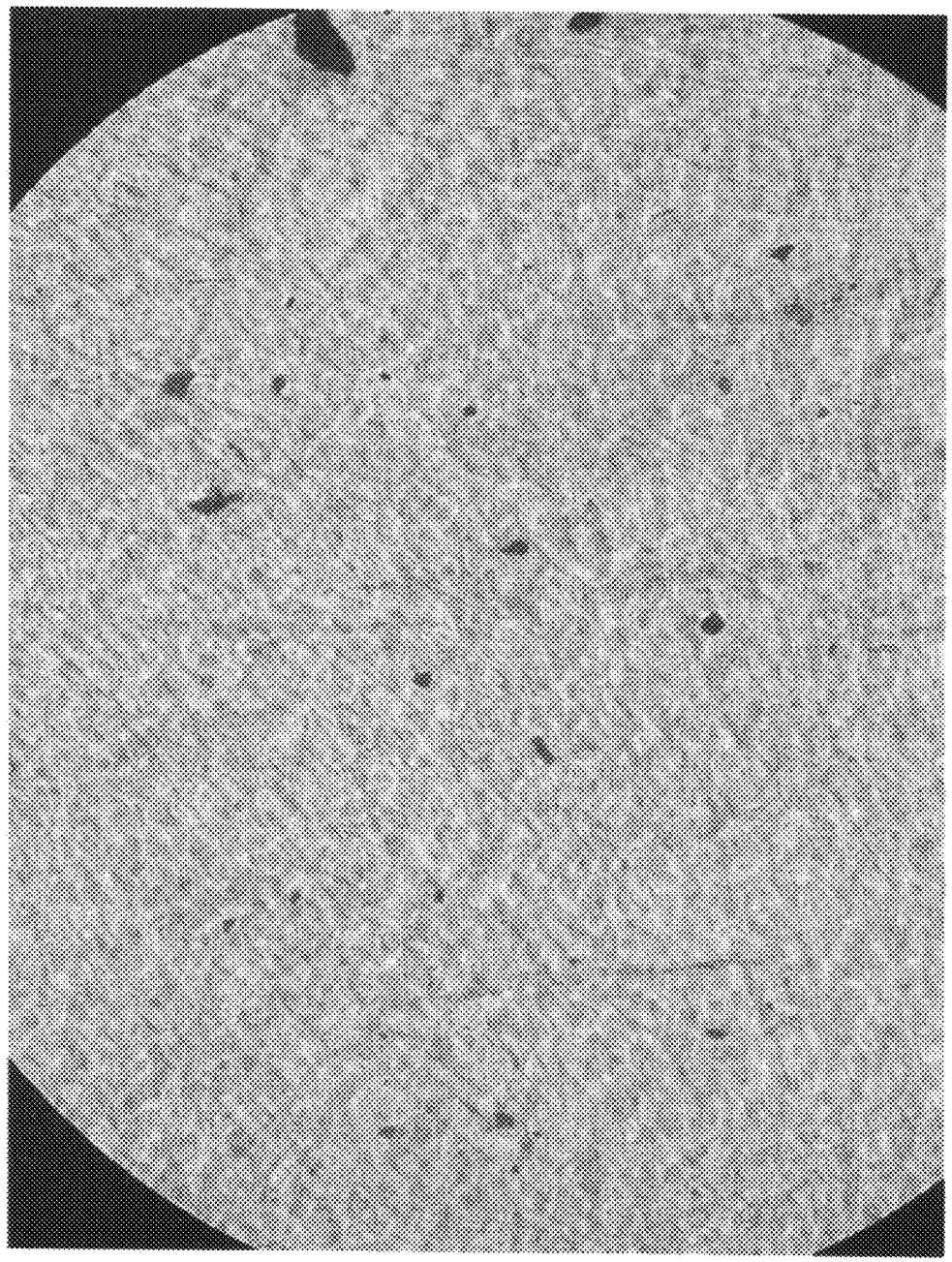
FIG. 1 shows methylene blue staining of neurons that have differentiated from neural progenitor cells grown on a fibroblast ALS.

Definitions. As used in this description and the accompanying claims, the following terms shall have the meanings indicated, unless the context otherwise requires:

"Autogenic Living Scaffold", or "ALS" as used herein means a 3-dimensional structure comprising cells (or entities) and the ECM (or matrix) that has been completely produced and arranged by these cells (or entities) that supports the growth of cells, tissue, organs, or combinations thereof. "Autogenic" means it is a self-produced scaffold, providing mechanical and nutritional and developmental support for the cells, tissues, organs, or combinations thereof. "Living" means that the scaffold is smart—it adjusts to its environment. "Living" also means it is biologically active and all components except seeded cells and tissue are naturally formed, produced, and synthesized by the scaffold system itself—i.e., the scaffold is autogenic. "Scaffold" means that it provides a structural framework for cells that guide their direction of growth, enables them to be correctly spaced, prevents overcrowding and enables cells to communicate between each other, transmit subtle biological signals, receive signals from their environment, and form bonds and contacts that are required for proper functioning of all cells within a unit such as a tissue.

"Resembles" as used herein means there is physical, functional, compositional, structural, phenotypic or other similarities between the materials or systems being compared, such that the objects are substantially equivalent. "Substantially equivalent" means that visible, microscopic, physical, functional, and other observations and assays do not easily or significantly distinguish the materials or systems. An easy or significant distinction would, for example, be a functional difference, a physical difference, a compositional difference, a structural difference immediately apparent, or easily detectable with standard assays and observational techniques such as staining, microscopy, antibodies, etc.

"Extracellular Matrix" (ECM) or "Cell Derived Matrix" (CDM) or Cell-produced Matrix as used interchangeably herein means a cell-derived secreted structural substance produced by and/or secreted from cells into the extracellular space. The ECM/CDM provides a growth template for any cell type to grow, differentiate, and produce tissue. Any cell type, as used herein, includes stem cells, progenitor cells, differentiated cells, and any other type of cell or entity. The ECM allows cell attachment and cell migration, and promotes cell differentiation. The ECM also aids the formation of new tissue of a desired or existing cell type As used herein means, "Cell-Produced Matrix, also called Cell-Derived Matrix (CDM)" also means a 3-dimensional ECM (or matrix) structure that has been completely produced and arranged by cells (or entities) in vitro.

"Construct" as used herein means a physical structure with mechanical properties such as a matrix of scaffold. Construct encompasses both autogenic living scaffolds and living tissue matrices, ex-vivo cell-produced tissue and cell-derived matrix.

"Cell-derived" as used herein means that the source for the material, body, or component is a cell or a collection of cells.

"Ex-vivo Cell-produced Tissue (ECT)" as used herein means, a functional tissue comprising one or more types of cells (or entities) and the ECM (or matrix) that has been completely produced and arranged by some of these cells (or entities). For example, an ex-vivo cell-produced neural graft consisting of an ALS that has been seeded with neuroprogenitor cells that differentiated in the ALS and formed neural tissue.

"Living Tissue Matrix (LTM)" as used herein means, a 3-dimensional tissue (or matrix) that is capable of being transformed into a more complex tissue (or matrix) or a completely different type of tissue (or matrix) that consists of cells (or entities) and the ECM (or matrix) that has been completely produced and arranged by these cells (or entities).

"Living Tissue Equivalent (LTE)" as used herein means, a construct containing living cells that intends to mimic a certain type of native tissue. This construct can be produced by any means in vitro, including by the use of artificial scaffolds.

"Superconfluent conditions" or "Superconfluency" means, within the context of the present application, that cells are grown and maintained in high-density growth conditions such that cells are packed almost directly next to and top of each other.

"Hyperconfluent conditions" as used herein means conditions for in vitro cell culture/growth such that cells and their associated ECM take up all the space at the bottom of the culture dish and have started to grow in the third dimension (on top of each other).

"Base media" as used herein means any cell culture medium that supports in vitro cultures of eukaryotic cells, including Dulbecco's Modification of Eagle's Medium (DMEM); Ham's F-12 (F12); Ham's F-10 (F10); Iscove's Modification of DMEM (IDMEM); MEDIUM 199; Alpha MEM; Basal Medium Eagle with Earle's BSS; Cyroprotective Medium (Freezing Medium); DMEM:F12 1:1; with L-Glutamine; Glasgow's MEM with L-glutamine (GMEM);

IMDM with HEPES, with or without L-Glutamine; L-15 (Leibovitz), without L-Glutamine; McCoy's 5A Modified Medium; Medium 199; MEM Eagle; MEM Eagle-Earle's BSS, with or without L-Glutamine; MEM Eagle-Hanks BSS; NCTC-109; Richter's CM Medium; RPMI 1640 with HEPES; RPMI 1640; or a combination of any of these.

"Glucocorticoid" as used herein, means dexamethasone, hydrocortisone, corticosterone, cortisol, cortisone, prednisone, prednilisone, methylprednisone, budesonide, beclometasone or any other compound classified as, or commonly referred to as, a glucocorticoid, or which interacts with the glucocorticoid receptor.

"Growing a large number of fibroblasts" as used herein means growing a plurality of cultures of fibroblasts to obtain at least about 1,000 cells/mm$^3$ to greater than 200,000 cells/mm$^3$, or growing a single culture to obtain at least about 1,000 cells/mm$^3$ to greater than 200,000 cells/mm$^3$.

"Growth and development" as used herein, means ability to reproduce and be viable, and includes proliferation and differentiation and/or tissue development.

"Fragility" as used herein, means a cell's tendency to be easily broken or damaged, and refers to a cell's physical frailty and weakness, lack of structural hardiness, and inability to remain intact if subjected to physical stress.

"Conditions that promote three-dimensional tissue growth" as used herein, means in vitro or in vivo conditions that facilitate, aid, further or in any way allow the development of three-dimensional tissue growth. Conditions may include use of specific media, growth factors, minerals, incubation temperature, cell density, aeration, agitation, use of ALS "molds" to shape and contain growth of desired tissue, use of sub-atmospheric pressure chambers such as SYNTHECON™ near-zero-gravity incubator systems (such as HARVs and STLVs) for growth of desired tissue, use of microcarrier beads, use of natural or biodegradable scaffolds, implanting a non-fibroblast-seeded autogenic living scaffold within an in vivo site such as in an organ or tissue such as connective, epithelial, muscle, and/or nerve tissue.

An "equivalent growth factor" as used herein means any growth factor that can replace a specific growth factor in a fibroblast cell culture without rendering the fibroblast cells non-viable. For epidermal growth factor (EGF), such equivalent growth factors include, but are not limited to, basic fibroblast growth factor (bFGF), fibroblast growth factor 2 (FGF-2), and transforming growth factor-α (TGF-α)

"Concentrations supportive of fibroblast growth and production of extracellular matrix" as used herein, means concentrations of growth media components, whether determined by molarity, weight/volume percent, weight/weight percent, volume/volume percent or any other standard means for measuring concentration, which allow fibroblast cells to grow, reproduce, proliferate, differentiate, or in any other way remain viable and produce extracellular matrix material.

"Regenerate tissue" as used herein means that autogenic living scaffolds with or without seeded cells and/or tissue, form, create, construct or otherwise generate tissue anew where previously there was none, or where previously the tissue was partially or completely non-functional.

"Supports the growth" as used herein means that growth is compatible with, and/or promoted by, the system of interest. For example, the phrase "the scaffold supports the growth of cells" or "supports the growth of tissue" or "supports the growth of organs" means that the ALS is compatible with, and/or promotes, the growth of cells, tissue or organs within or on or throughout the scaffold.

"Genetically engineered" as used herein means that a cell or entity, by human manipulation such as chemical, physical, stress-induced, or other means, has undergone mutation and selection; or that an exogenous nucleic acid has actually been introduced to the cell or entity through any standard means, such as transfection; such that the cell or entity has acquired a new characteristic, phenotype, genotype, and/or gene expression product, including but not limited to a gene marker, a gene product, and/or a mRNA, to endow the original cell or entity, at a genetic level, with a function, characteristic, or genetic element not present in non-genetically engineered, non-selected counterpart cells or entities.

"Smart" as used herein in regards to the autogenic living scaffold means that the living scaffold adapts to its environment, changes relative to its situation and surroundings, in both a reactive and active manner, interacting with and reacting to surrounding factors, cells, entities and structures through physical, biochemical, cell-signaling, enzymatic and/or genetic means. Being smart may also include morphing into a more complex, biochemically-, physically- and/or genetically-evolved material, system, scaffold or matrix; evolving functionally, physically, biochemically and/or genetically; and integrating functionally, physically, biochemically and/or genetically with surround cells, entities and materials.

"Cell or cell type suitable for production of extracellular growth matrix" or "produced by any suitable cell type" as used herein means any cell, cell type, or cell entity that can be manipulated to produce extracellular matrix in vitro. "Manipulated to produce extracellular matrix in vitro" means that growth conditions, growth media, supplemental factors, and appropriate stimuli exist and may be applied to these cells and entities to stimulate production of extracellular matrix material, in contrast to non-suitable cell types and cell entities wherein conditions, media, factors and stimuli do not exist and cannot be applied to stimulate production of extracellular matrix material.

"Lipid precursor" as used herein means a small molecular precursor in lipid synthesis or biosynthesis that forms the structural backbone for connection of the fatty acid chains. Examples include ethanolamine or equivalents such as o-phosphorylethanolamine, and also include any others that are interchangeable with ethanolamine in a serum-free medium for growing the ALS as herein disclosed.

The "Autogenic Living Scaffolds" (ALS) as disclosed herein are made and composed of living cells and the extracellular matrix (ECM) that these living cells produce. The living cells that these Autogenic Living Scaffolds contain may be genetically engineered or otherwise modified. They serve as blueprints, supporting structures, backbones, or scaffolds for the same or other cell lines or types. The ALS may also provide proper or supporting mechanical and chemical environments, signals, or stimuli to other cells, to the cells that produce the ALS, to surrounding tissue at an implantation site, to a wound, or for in vitro generation and regeneration of cells, tissue and organs. They may also provide other cells with nutrients, growth factors, and other necessary or useful components. They may also take in or serve as buffers for certain substances in the environment, and have also some potential at adapting to new environments.

The fibroblast produced matrix of the ALS, or "cell-derived matrix" (CDM), is composed of a number of insoluble extracellular matrix (ECM) molecules including fibronectin, collagen-1 and collagen-3, possibly in ratios resembling those in vivo. ALS could thus provide a more "natural" environment, or an environment more closely resembling that of native tissue in vivo, for both fibroblasts and other cells seeded onto them in vitro, than artificial scaffolds and reconstituted extracellular matrices such as collagen gels provide.

The ALS would thus potentially allow more accurate in vitro simulation of in vivo conditions to aid in better design of medical treatments and in vitro model systems.

In one embodiment, ALS is composed of slowly proliferating multilayered fibroblasts surrounded by dense extracellular matrices produced by the fibroblasts, a large proportion of which consists of supermolecularly organized collagen. The fibroblasts in this self-produced mechanically stressed environment assume a synthetic phenotype. The synthetic phenotype of fibroblasts is the phenotype most commonly found in connective tissue in vivo, and is an activated cell phenotype characterized by low cell proliferation, high collagen accumulation, fibrillar fibronectin organization, and the formation of actin stress fibers and focal adhesions (Kessler et al., 2001). This allows the ALS to be strong enough to provide structural support for other cell types seeded onto the matrix (and thus serve as a scaffold). The slow proliferation rate of the fibroblasts in the ALS keeps the fibroblasts from overgrowing other cell types. Changing the culture media from one that promotes fibroblast growth to one that promotes the growth and development of subsequently seeded cells (while at the same time possibly retarding the growth of the fibroblasts), also helps to ensure that the fibroblasts do not overgrow the seeded cells and/or tissue.

A chemically defined media allows more control of the ALS growth parameters (and thus its mechanical and chemical properties), and allows the elimination of non-human components in the in vitro biological model and scaffold for cell differentiation. Several chemically defined media for fibroblast have been formulated over the years (Bettger et al., 1981; Shipley and Ham, 1983; Parenteau, 1994; Vaccariello et al., 1999). None allows the efficient production of high-strength, high density, fast-growing ECM, while simultaneously keeping the growth of the fibroblast cells themselves sufficiently slow so that the fibroblasts do not over-run other cells seeded into the system. The ALS Medium allows the proper production of an autogenic "living" scaffold (ALS) system for producing cells and tissue of interest in vitro, for later implantation in vivo, wherein all components of the system are entirely defined, free from non-human components, and the ALS thus-formed is of sufficient strength, adaptability, and thickness to facilitate the growth of cells and tissue of interest in an efficient and economical manner.

Autogenic Living Scaffolds made up of fibroblasts (these may be only a few cells thick, or over 1 mm in thickness) and other similar classes of cells (most of the anchorage-dependent class of cells) such as stromal cells, especially those grown in serum-free conditions and whose growth rate and other characteristics may be controlled, may also serve another important role when implanted in vivo. For example, Fibroblast Autogenic Living Scaffolds (fALS) can grow and attach themselves to the site of implantation within a period of hours to days, and thus help to keep the implanted cells stationary with respect to the implantation site. This is very important, for example, in nerve grafts where a fraction of a degree change in the direction of a growing axon could/may prevent the nerves from making efficient connections with the existing nerves adjacent to the site of implantation. Fibroblast ALSs also have the capacity to adjust to their environments, making them "smart". For example, when a damaged portion of a heart is cut out and a fibroblast- or myofibroblast-ALS seeded with cardiomyocytes and/or skeletal muscle myocytes is implanted into this site, the fibroblasts or myofibroblasts grow and attach themselves to the remaining portions of cardiac muscle around the site of the incision in a relatively short period of time and keep the scaffold almost completely stationary relative to the surrounding cardiac muscle. The cardiomyocytes or skeletal muscle myocytes (or other seeded cells) then grow and develop into new cardiac muscle or into comparable cardiac muscle replacements that attach and join to the existing cardiac muscle. Using fibroblast- or myofibroblast-ALSs that are high in Collagen III relative to Collagen I (as is the case with the secreted ECMs from most foreskin fibroblasts), then scarring at the site of incision and implantation may be diminished.

The cells of an Autogenic Living Scaffold may also produce other useful and beneficial components at ratios that more closely simulate or resemble the natural environments that cells are exposed to in vivo. This helps the seeded cells to grow and develop into tissue and organs that more closely resemble native tissue and organs. When implanted in vivo, the Autogenic Living Scaffold is expected to disappear over time, at least partially, especially if the cells composing the Autogenic Living Scaffold are from a different host. However, the tissue or organ that develops from the cells seeded onto the Autogenic Living Scaffold is expected to remain. Apart from cardiac muscle and the heart, other organs or tissue may be produced using an ALS seeded with cells or tissue of interest. For example, liver tissue may be produced from an ALS that is seeded with hepatocytes; and kidney, pancreas, spinal cord, and other organs and tissues of the body may also be produced by seeding the ALS with the desired cell or tissue type. Autogenic Living Scaffolds seeded with the appropriate cell types may thus be used to grow implantable tissue and organs in vitro, for later implantation into an in vivo site. In general, when embodiments of the invention comprise the cells and scaffold they produce, the material is referred to as a Living Scaffold or an "Autologous Living Scaffold (ALS)". When the scaffold is seeded with cells to produce a tissue or organ, and used as such, the material is referred to as "ex-vivo cell-produced tissue (ECT) or organ (ECO)". Embodiments of this invention demonstrate that certain cells such as human skin fibroblasts can be induced to produce an extensive 3-D structural filamentous material, referred to herein as cell-produced matrix or cell-derived matrix (CDM), that forms a grid-like or mesh-like matrix which serves to facilitate and aid in the formation of new cell growth and tissue. The resulting Living Tissue Matrix (CDM+the fibroblasts that produced the CDM) is analogous to early connective tissue that forms prior to the migration and population of other cells to form tissues and organs composed of those particular cells. For example, during amphibian embryogenesis, the formation of the heart begins with the formation of this type of fibroblast-populated connective tissue followed by the transdifferentiation of these fibroblasts into cardiac cells to ultimately form the amphibian heart. In embryonic wound healing (and non-scar forming tissue wound healing), the wound bed is first filled with a type of fibroblast-populated connective tissue that is analogous to the Living Tissue Matrix followed by migration and repopulation of the wound site with cells of the damaged tissue. Preliminary experiments have indicated that LTMs provide the scaffolding and/or template for new cell growth for cells of any type (thus serving as "Living Scaffolds"), and serve to aid in cell attachment, migration, proliferation and differentiation, especially tissue generation and regeneration, at sites of tissue damage. Furthermore, the LTM can be transformed into an "implantable blastema" for multi-tissue regeneration in vitro by transdifferentiation and dedifferentiation of the fibroblasts within the LTM.

The Living Tissue Matrix is produced by the culturing suitable cells such as skin fibroblasts at hyperconfluent density in a completely chemically defined medium (no serum added) such as Matrix Media which causes them to enter a synthetic phase without significant proliferation (prior to being placed under these special conditions, the fibroblasts are induced to proliferate rapidly and are passaged without ever being allowed to attain confluence). In this phase, the secreted extracellular matrix (ECM) differs markedly from that of typical fibroblast cultures and more closely resembles the extracellular matrix found in generating/regenerating environments in vivo. There is a high ratio of type III collagen compared to type I along with high concentrations of hyaluronic acid and decorin.

Since the cells produce the entire 3D matrix by themselves, the LTMs appear to more closely resemble in vivo generative/regenerative connective tissue than any other matrix, scaffold or structure currently in existence. In fact, LTMs are similar in composition to the type of fibroblast-populated connective tissue that first fills the wound bed in embryonic wound healing (and other non-scar forming tissue wound healing) that regenerates without scarring as opposed to wounds in neonatal or adult mammals that heal with scarring. Furthermore, this method produces a 3-D construct (the LTM) that is significantly thicker and stronger than those obtained using biopolymer gels, such as collagen or fibrin gels. The entire Living Tissue Matrix (cells and ECM) can also be made completely autologous, thus preventing host rejection and making it completely immunocompatible.

The ECM produced in this system provides an optimal environment for de-differentiated or transdifferentiated autologous adult cells within the LTMs to create a regenerative environment and a virtual blastema. In other words, if the millions of fibroblasts within the LTM (the cells that produced the LTM in the first place) are de-differentiated or transdifferentiated, the LTM effectively becomes a structurally sound implantable blastema for multi-tissue type regeneration.

Living Tissue Matrices (LTMs) have potential for being used as soft tissue substitutes since they are produced solely from cells fed with a chemically-defined medium that does not contain animal components. The rapid growth and lack of expensive and inherently variable serum makes the development of LTMs as soft tissue substitutes commercially viable. Due to the relative simplicity of the chemically-defined medium, these cell-produced Living Tissue Matrices can also serve as in vitro biological models for the effects of nutritional components and pharmaceutical products on the growth and development of soft tissues. They may also be useful for studying numerous in vivo conditions and processes such as wound healing, soft connective tissue formation, fibrosis, and the development and interaction of different cells in a generating/regenerating tissue environment. The greater stability and mechanical integrity of LTMs over both collagen and fibrin gels allows them to retain their structural integrity longer in in vivo conditions than reconstituted ECM. The ability to grow LTMs thick and strong in a relatively short period of time in chemically-defined conditions enables the development of an attractive alternative to fibrin gels, collagen gels and even native tissues for tissue replacement.

Many different types of cells may also be seeded in different parts of the Living Scaffold, or they could be sandwiched on top of each other, to produce a variety of ex-vivo cell-produced tissues (ECTs) or organs (ECOs). For example, fibroblasts may first be grown in serum-free conditions favorable to promote a fibroblast ALS. The fibroblast ALS is then seeded with astrocytes, and the serum-free growth conditions (including the media, pH, osmolarity, temperature, oxygen tension, and anything else required) are adjusted to be favorable to the growth of the astrocytes. If needed, other components are added to keep the ALS alive and healthy. This entire structure or system may also be grown on porous membranes, such as TRANSWELLS™ or BD FALCON™/BIOCOAT™ Cell Culture Inserts, which allows media to be added to both the basolateral and apical sides of the ECT complex. Thus, media components more favorable to the growth and survival of the original cells (for example, fibroblasts) of the ALS may be added to the basolateral side of the entire ECT system or complex, while media components more favorable to the growth of the cells and tissue that are seeded onto the ALS may be added to the apical side of the entire system. Another option is to use cell culture systems such as OPTICELL™ that allows gas exchange to occur across the walls of the cell culture vessel where the cells can attach and grow, thus allowing an ALS or LTM grown up to a thickness of about 2 mm to be developed in vitro. Once a favorable layer of astrocytes has grown on the layer of fibroblasts, they may both be referred to as together making up the ECT, or the fibroblasts alone may be referred to as the LTM. Nerve cells may then be seeded on top of the layer of astrocytes, and the serum-free growth conditions again adjusted to be favorable to the growth and development of the nerve cells. If needed, other components are again added to keep the ALS and astrocytes alive and healthy, and the entire system may also be grown on a porous membrane to allow different media components to be added to the apical and basolateral sides of the entire system or ECT complex, as described above. Additional layers, such as skeletal muscle myocytes that might form into skeletal muscle tissue that is innervated by the already seeded nerves, may continue to be added in this or a similar fashion, as desired.

In another embodiment, the ALS or LTM may also be grown into specific shapes by molds, and may also be reshaped to some degree. For example, a sheet of the above example of an ALS, seeded first with astrocytes and then nerve cells, may be rolled into a cylinder. This cylinder may then be implanted into a spinal cord in vivo. The ALS also provides mechanical support to the seeded cells. For example, in a particular embodiment, an ALS seeded with neurons may be mechanically stressed and compressed, without major damage to the neurons, even though such a degree of mechanical stress and compression kills most neurons when grown in the absence of an ALS or without formation of the ECT. The ALS of other embodiments may also be introduced to mechanical stress or tension which may change the properties of the ALS and any cells or tissue that are growing on it.

In one particular embodiment, the fibers of a Fibroblast Autogenic Living Scaffold may also be made to grow in parallel, which helps seeded nerve cells to also grow in parallel along these fibers, especially when Schwann cells are previously seeded onto the scaffolds and first start growing in parallel along these fibers. This may be even more useful when implanted in the spinal cord, since the implanted nerve cells may then be aligned in the same direction as the native nerve cells in the spinal cord. In still another embodiment, a sheet of ALS with the seeded neurons may also be rolled into a cylinder prior to implantation to produce a structure with layers of neurons aligned in the same general direction as the native neurons in the spinal cord. Similar things may be done for implantation into other tissues and organs.

In other particular embodiments, cell to cell, tissue to tissue, and tissue to cell interactions may also be studied in vitro and in vivo with Autogenic Living Scaffolds and LTMs, such as by sandwiching different cells. In yet another embodiment, Autogenic Living Scaffolds and LTMs may be used as in vitro biological models for studying the growth and development of cells, tissues, organs, systems, diseases, and different responses in organisms. For example, the wound response (in which fibroblasts play an active role) on different types of cells and tissues may be studied in vitro by using this technology.

A current shortage of load-bearing tissue has created a demand for human-made tissues that can withstand in vivo mechanical forces Most of the strength of connective tissues is due to the collagen content per unit mass of tissue. The high tensile strength of collagen is largely attributable to the presence of intermolecular covalent cross-links between the collagen fibrils Strength increases with increasing collagen fibril diameter (which are typically in the order of up to 100 nm in diameter in native tissue, and 40-60 nm in developing native connective tissue), as well as with increasing density and cross-linking of collagen fibrils. For the collagen in fibroblast based ALSs (fALS) and LTMs, a density of over 100 collagen fibrils/$\mu m^2$ can be achieved with a high degree of cross-linking between the fibrils. The collagen fibril diameters in ALSs where the fibroblasts are derived from the dermis of neonatal human foreskin, have so far been in the order of 40-50 nm, indicating similarity to young connective tissue in vivo that has greater regenerative potential than mature connective tissue. Mechanical strength of collagen can also be increased through magnetic alignment of the collagen fibrils and by the addition of lysyl oxidase that induces additional cross-links between the collagen fibrils Strength also increases with the addition of fibronectin, which in turn increases actin organization and regulates the composition of the ECM. For example, fibronectin induces a 5-fold increase in the ultimate tensile strength of fibroblast populated collagen lattices In particular embodiments, fibronectin is generally the second most abundant ECM protein after collagen in ALSs fed with the Matrix Media.

Fibroblasts (especially foreskin fibroblasts) secrete numerous growth factors including nerve growth factor (NGF), brain-derived neurotrophic factor (BDNF), and neurotrophin-3 (NT-3), as well as fibroblast growth factor (FGF), and platelet-derived growth factor (PDGF), all of which promote neuron regeneration and survival. The embodiments of ALSs and LTMs described herein more closely mimic the extracellular environment that nerve cells are normally exposed to in vivo than any other currently available scaffolds, and even allow primary nerve cells to form active 3-D neural networks in vitro that can serve as in vitro 3-D models for potential therapeutic agents for neuronal regeneration, as may also be used to functionally replace injured spinal cord neurons in vivo.

Previous experiments show that fibroblasts grafts obtained from an in vivo site have allowed axons to elongate ~0.5 nm/month at a density of ~28 axons/$\mu m^2$, and have provided functional recovery within 3 months of up to ~10 on the BBB scale (Basso, Beattie and Bresnahan locomotor rating scale—scale range: 0-21, with 0 representing no function, and 21 representing complete locomotor functionality—in animals; (Lu et al., (2002) *Brain* 125(Pt 1):14-21), when implanted into chronically injured spinal cord in rats and monkeys. When the fibroblasts are genetically modified to express 10× more BDNF and NGF, these numbers jump to ~2.1 mm/month at a density of ~70 axons/$\mu m^2$, and functional recovery is further slightly improved. The fibroblasts stopped proliferating after they were implanted at high density, and the grafts also prevented the formation of fibrosis at the site of injury and implantation. Furthermore, the fibroblast grafts promoted rapid and extensive migration of Schwann cells into the grafts from the peripheral nervous system, which is considered to be a major and necessary factor of functional spinal cord regeneration.

Other research showed that collagen gels and collagen filament implants allowed axons to elongate up to 5 mm within a month, and provided functional recovery within 3 months of up to ~12 on the BBB scale when implanted into injured spinal cords in rats. Still others have shown that fibronectin mats have allowed axons to elongate up to 4-5 mm and reach diameters of up to 3.5 $\mu m$ within a month, and provided functional recovery within 3 months of up to ~10 on the BBB scale when implanted into injured spinal cords in rats. Implanted fibronectin has also been found to aid in the proper orientation of elongating neuronal axons at the site of implantation in the damaged spinal cord, as well as in attracting Schwann cells from the peripheral nervous system.

In the case of particular embodiments of fALS of the present application, the high density of fibroblasts along with the insoluble ECM proteins collagen and fibronectin of the ALS work in conjunction to promote axon elongation and functional recovery when implanted into chronically injured spinal cord. It is within the realm of the presently disclosed ALS systems that a particular ALS seeded with primary neuronal cells that produces differentiated nerve cells and/or tissue may allow axons to elongate up to as much as ~10 mm/month and may promote the beginnings of functional recovery within 1 month, ideally increasing to a value approaching 20 on the BBB scale after 3 months. It is also within the realm of embodiments of the presently disclosed ALS systems that a particular ALS seeded with primary neuronal cells that produces differentiated nerve cells and/or tissue may allow between ~0.5 mm/month axon elongation and about 10 on the BBB scale within 3 months, and up to about 10 mm/month axon elongation and preliminary functional recovery within 1 month, increasing to a value approaching 20 on the BBB scale after 3 months. Other particular embodiments of fALS systems seeded with primary neuronal cells are envisioned to allow intermediate axon elongation, anywhere from about 3-8 mm/month of axon elongation, with functional recovery again approaching about 20 on the BBB scale after 3 months.

It is known that implanted neural progenitor cells survive for long periods of time at the site of implantation in injured spinal cord and support axonal elongation and limited functional recovery, and that neural progenitor cells differentiate into nerve and glial lineages and survive for much longer than neuroblastomas (which usually die before making any active synaptic connections—a requirement for survival and nutritional support from the glial cells). Neural progenitor cells are also deemed far more safe and predictive than stem cells, which are difficult to control and are thought to be one of the main promoters of cancer in the central nervous system. Unfortunately, neural progenitor cells differentiate only into astro- and oligodendro-glial lineages when implanted into injured spinal cord, or when cultured in vitro in the absence of ALS systems according to the present invention. When neural progenitor cells are seeded in vitro onto an ALS in accordance with embodiments of the present invention, however, the neural progenitor cells differentiate into nerve and glial lineages, as shown in FIGS. 1 through 7.

Furthermore, neuroblastomas seeded in vitro together with neural progenitor cells or astrocytes onto ALS according to embodiments herein, are envisioned to allow the long-term differentiation and survival of the neuroblastomas on the ALS and also at the site of in vivo implantation in injured spinal cord. Also, basic fibroblast growth factor, which is secreted by the fibroblasts of particular embodiments of the ALS systems described herein, induces the secretion of neural growth factor (NGF) by astrocytes grown on the ALS in serum-free culture conditions.

Research Design and Methods

Example: Using the ALS as a Scaffold for Creating a Nerve Graft:

There is currently no proper treatment for spinal cord injury. Limited spinal cord regeneration has been achieved in a small number of patients through physical rehabilitation and training, peripheral nerve grafts, and by transplanting fetal spinal cord tissue. Most patients are limited to being dependent on the use of a wheelchair and even on devices that sustain/replace lost autonomic function.

There are a number of approaches in current research into treatments for spinal cord injury. The current limitation of all these approaches is that they restore only partial and generally minimal functionality to the injured spinal cord. The first clinical trials for the treatment of spinal cord injury began on Jul. 11, 2002, in Australia by transplanting olfactory ensheathing glia into patients' spinal cords. The limitation of this approach is that it takes several years to restore some of the functions lost due to the spinal cord injury, and the restoration of these functions is limited (from a 1 to 4.3 on the Basso, Beattie and Bresnahan (BBB) locomotor rating scale (scale range: 1-20, with 1 representing no function, and 20 representing complete locomotor functionality) in animals). Another clinical trial involving the vaccination of Copolymer-1 into patients with recent (<14 days) spinal cord injury is about to start in Israel and the United States, but this treatment is designed more to slow down and possibly reverse the degeneration of nerve cells in diseases such as Parkinson's disease rather than being designed as a means for regenerating injured spinal cord nerve cells.

There is somewhat of a consensus in the field of neuroregeneration that the necessary elements for potential tissue engineered nerve constructs include: 1) a scaffold for nerve growth and axonal migration; 2) support cells; 3) growth factors; and 4) extracellular matrix. To date, no system that includes all the elements has been described or disclosed that successfully generates nerve cells in vitro, for later in vivo implantation. In addition, there are no in vitro 3-D models of neuronal growth or regeneration. Since the ALS provides an environment that closely resembles the extracellular environment that neurons are normally exposed to in vivo, the proposed tissue engineered nerve grafts created using the ALS could be used for a variety of in vitro applications, such as studying the effects of potential therapeutic agents on neuronal regeneration. In terms of serving as a nerve graft for replacing damaged spinal cord, this system uses only human components and has the potential to replace/regenerate spinal cord that is extensively damaged over large areas and distances since it contains its own nerve cells/neural tissue.

Preliminary studies have indicated that the majority of neurons grown within an ALS in accordance with the present invention are still alive after a ~200-μm thick graft has been gently folded into itself and then gently unfolded, as determined by a neuronal viability assay (Molecular Probes LIVE/DEAD Viability/Cytotoxicity kit # L-3224) before and after handling of the nerve graft (data not shown). However, in such an ALS, the neurons represent only a small fraction of the ~200-μm thick graft. Thus, in particular embodiments, neurons may be seeded onto thinner supportive ALSs wherein the ultimate tensile strength (UTS) of the ALS is increased by small modification to the ALS Medium. Alternatively, in other embodiments the porosity of the ALS may also be increased, to allow neurons to migrate throughout thicker ALSs. The fALSs in accordance with particular embodiments of the present invention are prepared by seeding human foreskin fibroblasts at high density onto wells or TRANSWELL™ polymer-based, permeable membrane, culture well support inserts, and allowing the fibroblasts to develop a 3-D matrix having a thickness of between 50 to several hundred micrometers over a period of several weeks. The fibroblasts are fed with a defined "chemical" media that does not contain any serum or animal components, referred to herein as Fibroblast Autogenic Living Scaffold Medium (fALS Medium), an example of which is Matrix Media, and described in Example 1. In a particular embodiment, after the 3-D matrix (ALS) is produced, the ALS is seeded with primary neuronal cells. The ALS with the seeded neuronal cells is then fed with another defined "chemical" medium (again, a medium with no serum or animal components) that supports the growth of the neurons and retards the growth of the fibroblasts. In one embodiment, the ALS seeded with primary neuronal cells is maintained in a TRANSWELL™ polymer-based, permeable membrane, culture well support insert, allowing the basal side of the ALS to continue being fed with the first media (fALS Media) while the apical side of the ALS is fed with the second media.

The development of a functional neural network in vitro allows the nerve graft to have more utility when implanted, and is important for studying the effect of different pharmacological agents and methods on the in vitro 3-D neural network model disclosed herein. To date, no functional neural networks grown in vitro have been able to be transferred and implanted into a host due to the frailty of these neural networks—nerves are so frail that they cannot even support their own weight, and no scaffolds (apart from the fALS disclosed herein) have yet been developed that provide adequate structural support to these nerves. To optimize the production of functional neural networks, the nerve graft in one embodiment may be grown on a 64-microelectrode array, or alternatively, voltage-sensitive dyes may be used to determine the functionality (presence of action potentials) and connectivity (presence of phasic bursting patterns) of the neurons (see Mistry et al., (2002) *Proc Natl Acad Sci USA* 99(3):1621-6 and Segev et al., (2003) *Phys Rev Lett* 90(16): 168101, both of which are incorporated by reference herein) in the ALS. In this way different types of primary neurons (such as neural progenitor cells and neuroblastomas) may be tested to determine which types differentiate and produce the most favorable functional neural networks in the particular embodiments of ALS as described herein.

In other embodiments the effects of different nutritional supplements and growth factors on the development of the functional neural networks in the ALS may also be studied in this way. For example, FGF-2 and BDNF have been shown to support the development of extensive and spontaneously active neural networks from primary neurons within 3 weeks (see Mistry et al., 2002). Preliminary results with ALSs seeded with primary neuronal cells in accordance with the present invention show that the carbohydrate source galactose is favored over glucose by neurons, and that galactose also significantly retards the growth of the fibroblasts in the ALS. Thus, in embodiments of the present invention, once the neurons are seeded onto the ALS, the growth media is changed from one that supports ALS growth to one that promotes neuronal growth and differentiation, while at the same time retards the growth of fibroblasts. This prevents the fibroblasts from over-running the neurons and effectively preventing neuronal development. In other embodiments, the fibroblasts may be genetically engineered to secrete more growth factors such as NGF, BDNF, FGF-2, and bFGF to enhance neuron survival and development even further.

Specific neuronal markers such as Anti-Hu MAb 16A11 (Marusich et al., (1994) *J. Neurobiol* 25(2): 143-155, incorporated by reference herein) may be used to differentiate neurons from fibroblasts (see FIGS. 3 through 7, and 12 through 13). The degree of attachment and differentiation of neurons on ALS can be determined (no. of differentiated neurons/no. of primary neurons seeded), along with how far the axons elongate through the ALS (average length of axons in 4-10 fields of view (see Segev et al., 2003)) and the length of time that the neurons are viable on the ALS (from the time of seeding). Determining the length of time that the neurons are viable on the ALS allows the graft to be implanted days prior to the degeneration of the nerves, thereby ensuring that the nerves remain alive and functional in the host/patient to better the chances for neurogenesis. In addition, histology and transmission electron microscopy (tEM) may be used to observe the arrangement and connectivity of the neurons (Jin et al., (2002) *Exp Neurol* 177(1):265-75 and Tuszynski et al., (2002) *J Comp Neurol* 449(1):88-101, both of which are incorporated by reference herein) in the ALS.

It is expected that superior results may be achieved when a particular embodiment of an ALS nerve graft is implanted 2 weeks after spinal cord injury, since this is when BDNF-expressing and supporting microglia, as well as peri-wound sprouting around the site of injury, begin to reach significant levels. However, in particular embodiments, the ALS nerve graft contains active neurons, including primary neurons that have begun to differentiate and form active neural connections (see FIGS. 2-4, for example), so positive results are expected regardless of when the ALS nerve graft is implanted.

In other embodiments, the ALS nerve graft has the flexibility of taking on almost any non-rigid shape and may be rolled up into a ball or cylinder. Several thin nerve grafts may also be layered on top of each other to form different parallel layers of neural networks, which in turn may again be rolled up into a cylinder or formed into some other shape. Alternative forms and structures of ALS nerve grafts are expected to give better results in terms of functional recovery for each type of spinal cord injury (longitudinal, transverse, shear, etc.). The requirement for immune-suppressants may also be determined, although such agents are not expected to be required since nerve cells are not attacked by the immune system in humans and fibroblasts do not elicit much of an immune response. Alternatively, in other particular embodiments nude rats may be used as models for implanting human nerve grafts, to study functional recovery promoted by the ALS nerve grafts in accordance with embodiments of the present invention.

In still other embodiments, the ALS nerve grafts as herein described, may be benchmarked against other current approaches, e.g., according to the extent of functional recovery in spinal cord injury-induced animals (using the BBB scale as a standard), or according to the extent of active functionality of implanted/regenerated nerve cells (as determined electrophysiologically), or according to the extent of complications, the time to functional recovery from the date when the procedure is started, and from a cost/feasibility perspective.

EXAMPLES

Example 1a

Serum-Free Chemically-Defined Medium for Growing Fibroblast ALS—"fALS Medium" or "Matrix Media"

One embodiment of a chemically defined media formulation in accordance with the present invention contains:

A 3:1 ratio of DMEM (high glucose (4.5 g/L); with L-glutamine and sodium pyruvate) and Ham's F12 medium supplemented with the following components:

$4.2 \times 10^{-10}$M Epidermal Growth Factor (in human serum albumin)
$2.8 \times 10^{-10}$M Basic Fibroblast Growth Factor
$8.6 \times 10^{-5}$M insulin
$1.0 \times 10^{-7}$M dexamethasone
$3.2 \times 10^{-4}$M L-ascorbic acid phosphate magnesium salt n-hydrate
$2 \times 10^{-10}$M L-3,3',5-triiodothyronine
$10^{-4}$M ethanolamine
$3.9 \times 10^{-8}$M selenious acid
$4 \times 10^{-3}$ M L-analyl-L-glutamine (GLUTAMAX™)
$3.3 \times 10^{-6}$M glutathione (reduced)
1% penicillin/streptomycin/amphotericin B In addition, other embodiments and variations of the above-listed medium may contain additional components, such as any one or more of the following components:

Platelet derived growth factor (PDGF)
100:68 ratio of glycine:L-proline
L-cysteine
6-hydroxy-2,5,7,8-tetramethychroman-2-coarboxylic acid ("TROLOX™").

Concentrations may vary as required, as long as the total osmolarity in the medium is kept at acceptable levels for growth of the ALS. For example, L-ascorbic acid phosphate magnesium salt n-hydrate may range in concentration from 0.1 mM to 3 mM; EGF may range in concentration from 0.002 nM to 2 nM; bFGF may range in concentration from 0.03 nM to over 3 nM; insulin may range in concentration from 10 pM to 1000 pM; PDGF may range in concentration from 0.1 ngiml to 10 nglml; L-3,3',5-triiodothyronine may range in concentration from 0.1 nM to 10 nM; ethanolamine may range in concentration from 1 pM to 10,000 pM; selenious acid may range in concentration from 10 nM to 1000 nM; L-analyl-L-glutamine (GLUTAMAX™) may range in concentration from 0 mM to 10 mM; glycine:L-proline concentrations (still at a 100:68 ratio) may be supplemented with from 0 mM glycine:146 mM L-proline; to 2.675 mM glycine: 1.965 mM L-proline; dexamethasone concentrations may vary from 1 nM to 1000 nM; L-cysteine concentrations may be supplemented with additional 0.1 mM to 1 mM.

Example 1b

Serum-Free Chemically-Defined Medium for Growing Neuronal Cells/Tissue—"Neural Medium"

One embodiment of a chemically defined media formulation in accordance with the present invention contains:

A 2:3 ratio of DMEMF12 and NEUROBASAL MEDIUM™ (Gibco-Invitrogen Corporation) supplemented with the following components:

$3 \times 10^{-10}$M Fibroblast Growth Factor 2
$8.5 \times 10^{-6}$ M D(+)galactose
$6.0 \times 10^{-8}$M progesterone
$6.0 \times 10^{-7}$M retinyl acetate
$9.0 \times 10^{-8}$M corticosterone
$1.0 \times 10^{-4}$M putrescine
$1.0 \times 10^{-5}$M carnitine
$1.3 \times 10^{-5}$M linoleic Acid
$4.3 \times 10^{-6}$M linolenic Acid
$4.0 \times 10^{-6}$M biotin
$4.0 \times 10^{-6}$M 6-hydroxy-2,5,7,8-tetramethychroman-2-coarboxylic acid ("TROLOX™").
1% penicillin/streptomycin/amphotericin B In addition, other embodiments and variations of the above-listed medium may contain additional components, and concentrations may vary as required.

Example 2

Production of Extracellular Matrix by Fibroblast Cells Isolated from the Dermis of Newborn Human Foreskin Large numbers of fibroblast cells were isolated from the dermis of newborn human foreskin. Cells were proliferated in cell culture flasks fed with DMEM Medium with 10% Nu-Serum (or FBS or BCS) for several weeks. After a few passages, the fibroblast cells were centrifuged at 1000 RPMs, the supernatant decanted, and the cells pooled. These pooled fibroblast cells were resuspended in ALS Medium as described above in Example 1, then seeded into TRANSWELLS™ or BD FALCON™/BIOCOAT™ Cell Culture Inserts or 6- or 12-well plates or other small containers suitable for in vitro cell culture, at superconfluent conditions, whereby cell density was between about 200,000 to greater than about 1,000,000 cells/cm2. The fibroblast cells were maintained at hyperconfluent conditions for about 3 weeks (or optionally about 1 week or longer than 10 weeks), during which time they were observed to produce Extracellular Matrix, thus creating a Fibroblast ALS about 300 pm thick. See FIGS. 3-9, and FIGS. 12-13, for example, showing clearly visible extracellular matrices. Other embodiments may include Extracellular Matrices that have been produced by the fibroblasts resulting in ALSs that are 50 pm to 500 pm thick, or even up to or greater than 1 mm thick.

In one embodiment, the fibroblast ALS is grown on a circular porous polyethylene (Huang et al., (1993) *Annal Biomed Eng* 21(3): 2890305 and Uysal et al., (2003) *Plast Reconstr Surg* 112(2):540-6, both of which are incorporated by reference herein) or ceramic support that exposes both sides of the ALS to media. This allows the ALS to grow faster and thicker due to the shorter diffusion distance for gases and nutrients than when the ALS is exposed to media on only one side at the bottom of a culture well. Alternatively, the ALS is grown on 0.4 pm TRANSWELLS™ (Corning, 2003), although this limits the subsequent seeding of other cell types to just one side of the CDM. The use of OPTICELL™ allows the ALS to grow up to about 2 mm thick in vitro due to the efficient gas exchange from both sides of the ALS. Another alternative is to use an advanced cell and tissue culture apparatus that allows the constant perfusion of media and oxygen to the cell and tissue of an ALS (e.g. MINUCELLS™ and MINUTISSUE™) since they allow the constant perfusion of media and oxygen to the cells and tissue of ion the ALS. Using 0.4 pm TRANSWELLS™ or center-well organ culture dishes (BD Biosciences # 353037) also allows more nutrient media to be used and permits the cells to be closer to an 0, source. The availability of 0, may be further enhanced by increasing the partial pressure of 0, (PO,) that the cells and inside of the culture vessel are exposed to. The pores in the porous polyethylene or ceramic support provide adequate sites of ECM attachment for the ALS. Cells are prevented from growing on the wells and the outside circle of the porous polyethylene or ceramic supports by treating these areas with a non-binding substance such as SIGMACOTE (Sigma # SL-2), once the ALS is grown in a suspended or floating state. Suspended ALSs may be induced to have more dendritic fibroblast morphology, thereby allowing more flexibility in modifying the characteristics of the ALS, for example, through the use of mechanical stimulation.

Example 3

In Vitro Protocol for Generating Neuronal Cells/Tissue

In one embodiment, a large number fibroblast cells (Cambrex CC-2509) were centrifuged, at approximately 1000 rpm for about 8 min, followed by removal of the supernatant. The resulting fibroblasts were then resuspended in ALS Medium and seeded into TRANSWELLS™ or BD FALCON™/BIOCOAT™ Cell Culture Inserts at superconfluency (between about 1,000 cells/mm3 to greater than 200,000 cells/mm3), and fed with ALS Medium every 2-3 days for about 2-3 weeks or longer at hyperconfluent conditions until the desired amount and thickness of ALS had formed. At this point, the ALS containing fibroblasts and extensive CDM was seeded with neural progenitor cells (Cambrex CC-2599), and the basolateral side of the TRANSWELLS™ continued to be fed with fALS Medium while the apical side was fed with Neural Medium every 2-3 days for another 2-4 weeks or longer.

Figure 2:
FIG. 2 shows a fluorescent live/dead assay performed on neural progenitor cells grown on a fibroblast ALS, where the fibroblasts had been killed prior to seeding with human neural progenitor cells. Live neurons (nerve and glial cells) fluoresce as green; the nuclei of dead cells (mostly fibroblasts) fluoresce as red.
Figure 3:
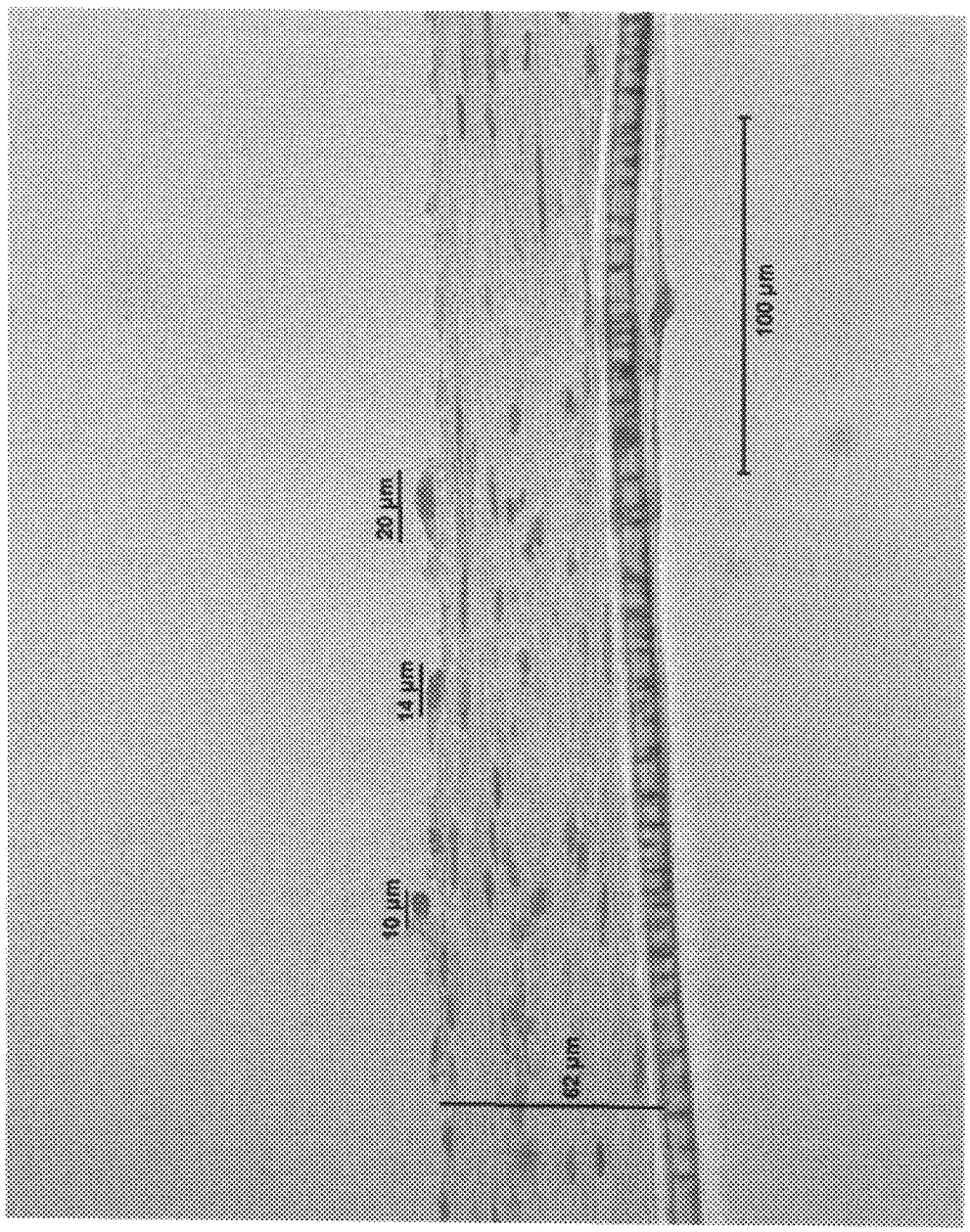
FIG. 3 shows a cross-section of a 17-day fibroblast ALS system about 50-60 µm thick containing neuronal cells/tissue that are expressing anti-Hu MAb 16A11, an early marker of vertebrate neurogenesis that is expressed shortly after neuronal terminal mitosis (Marusich, M. F. et al (1994) *J. Neurobiol.* 25: 143-155). The marker is observed in nerve cell bodies as reddish brown spots; cell nuclei are blue. The ALS was allowed to grow for 4 weeks prior to seeding with human neuroprogenitor cells.
Figure 4:
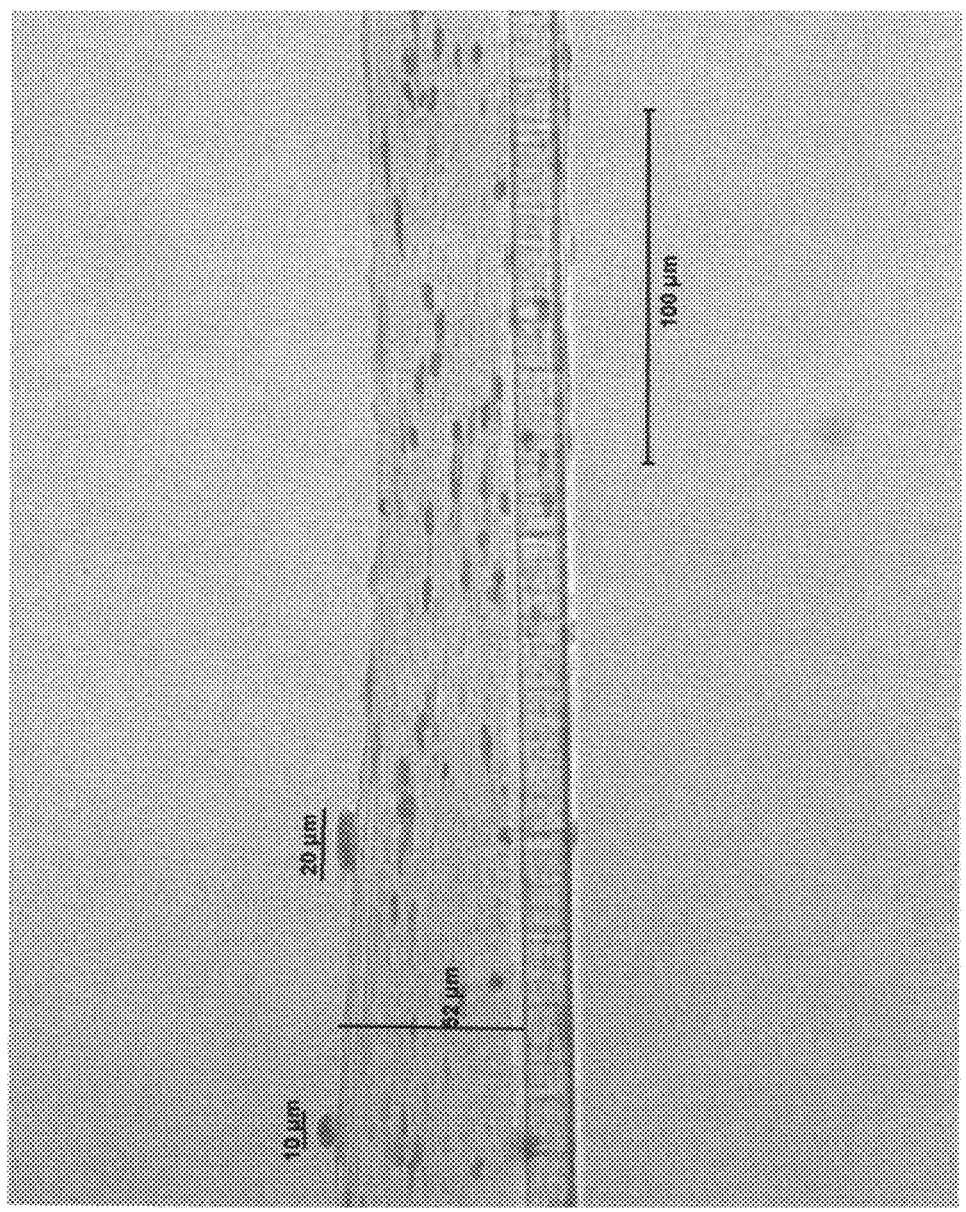
FIG. 4 shows another cross-sections of a 17-day fibroblast ALS system about 50-60 µm thick containing neuronal cells/tissue that are expressing anti-Hu MAb 16A11, an early marker of vertebrate neurogenesis that is expressed shortly after neuronal terminal mitosis (Marusich, M. F. et al (1994) *J. Neurobiol.* 25: 143-155). The marker is observed in nerve cell bodies as reddish brown spots; cell nuclei are blue. The ALS was allowed to grow for 4 weeks prior to seeding with human neuroprogenitor cells.
Figure 5:
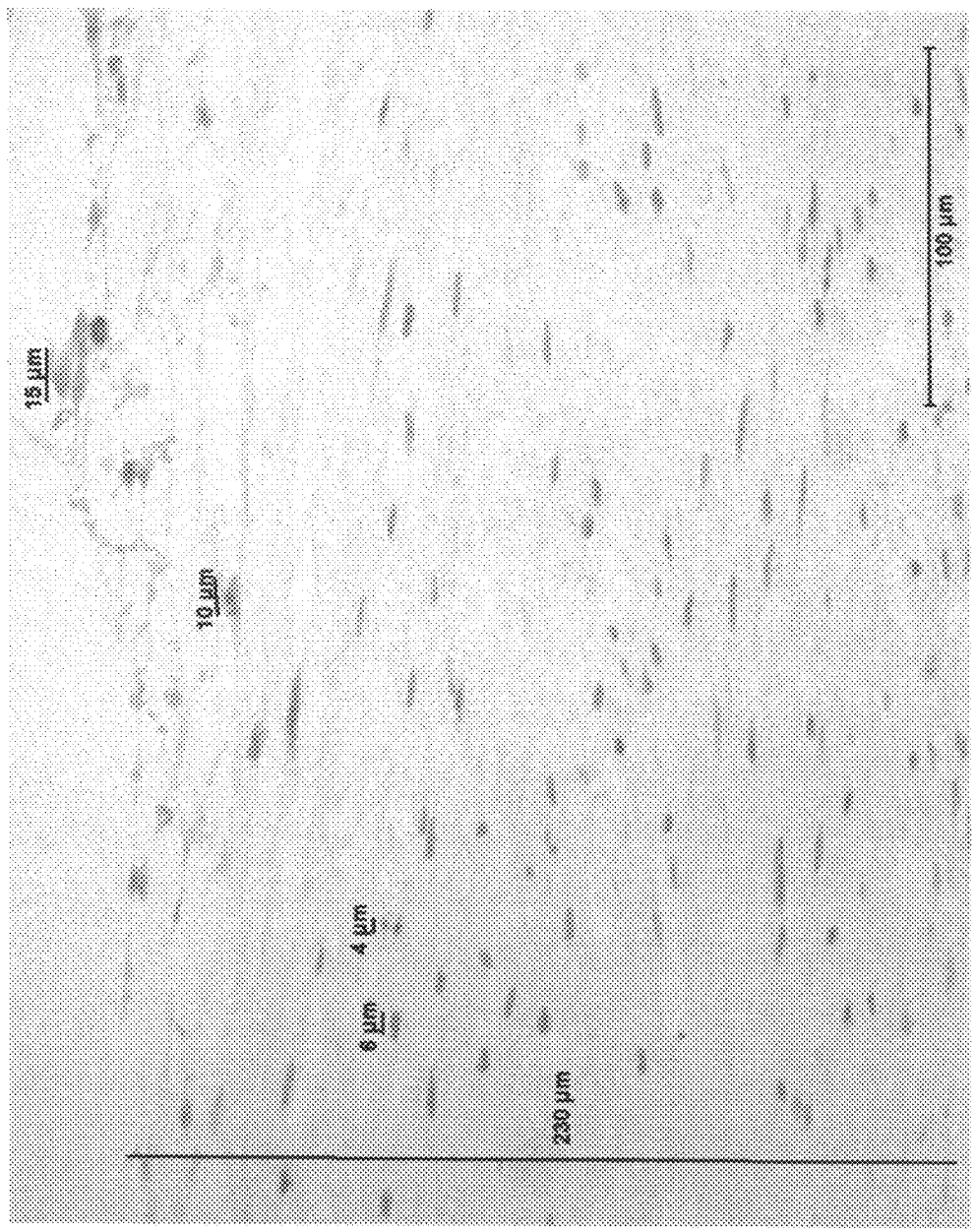
FIG. 5 shows cross-sections of a 31-day fibroblast ALS system about 216-230 µm thick containing neuronal cells/tissue that are expressing anti-Hu MAb 16A11. The ALS was allowed to grow for 3 weeks prior to seeding with human neuroprogenitor cells. As can be seen, varying-sized regions (different cross-sections of nerve cell bodies) expressing the anti-Hu MAb 16A11 marker are indicated, ranging in size to over 20 µm.
Figure 6:
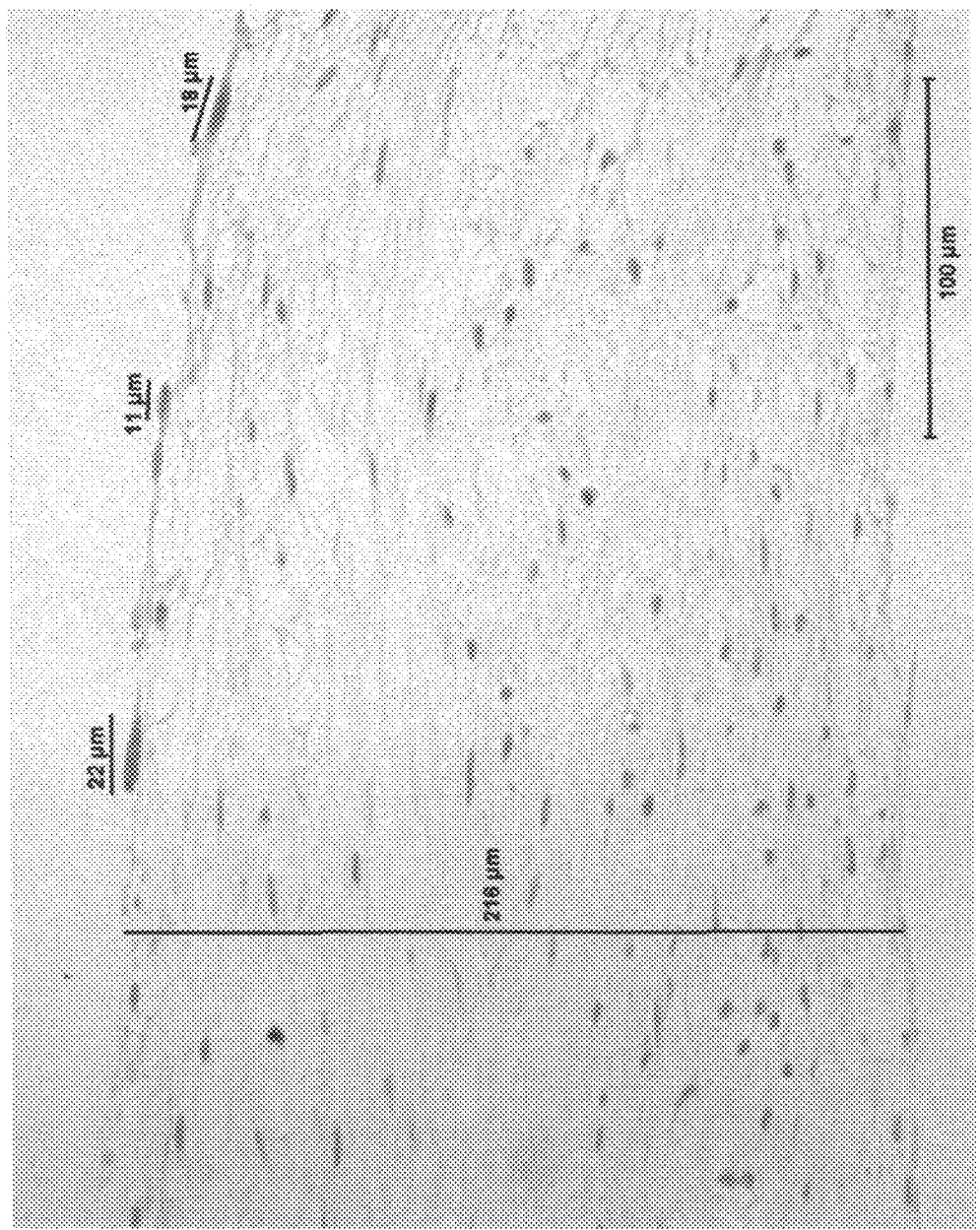
FIG. 6 shows another cross-sections of a 31-day fibroblast ALS system about 216-230 µm thick containing neuronal cells/tissue that are expressing anti-Hu MAb 16A11. The ALS was allowed to grow for 3 weeks prior to seeding with human neuroprogenitor cells. As can be seen, varying-sized regions (different cross-sections of nerve cell bodies) expressing the anti-Hu MAb 16A11 marker are indicated, ranging in size to over 20 µm.
Figure 7:
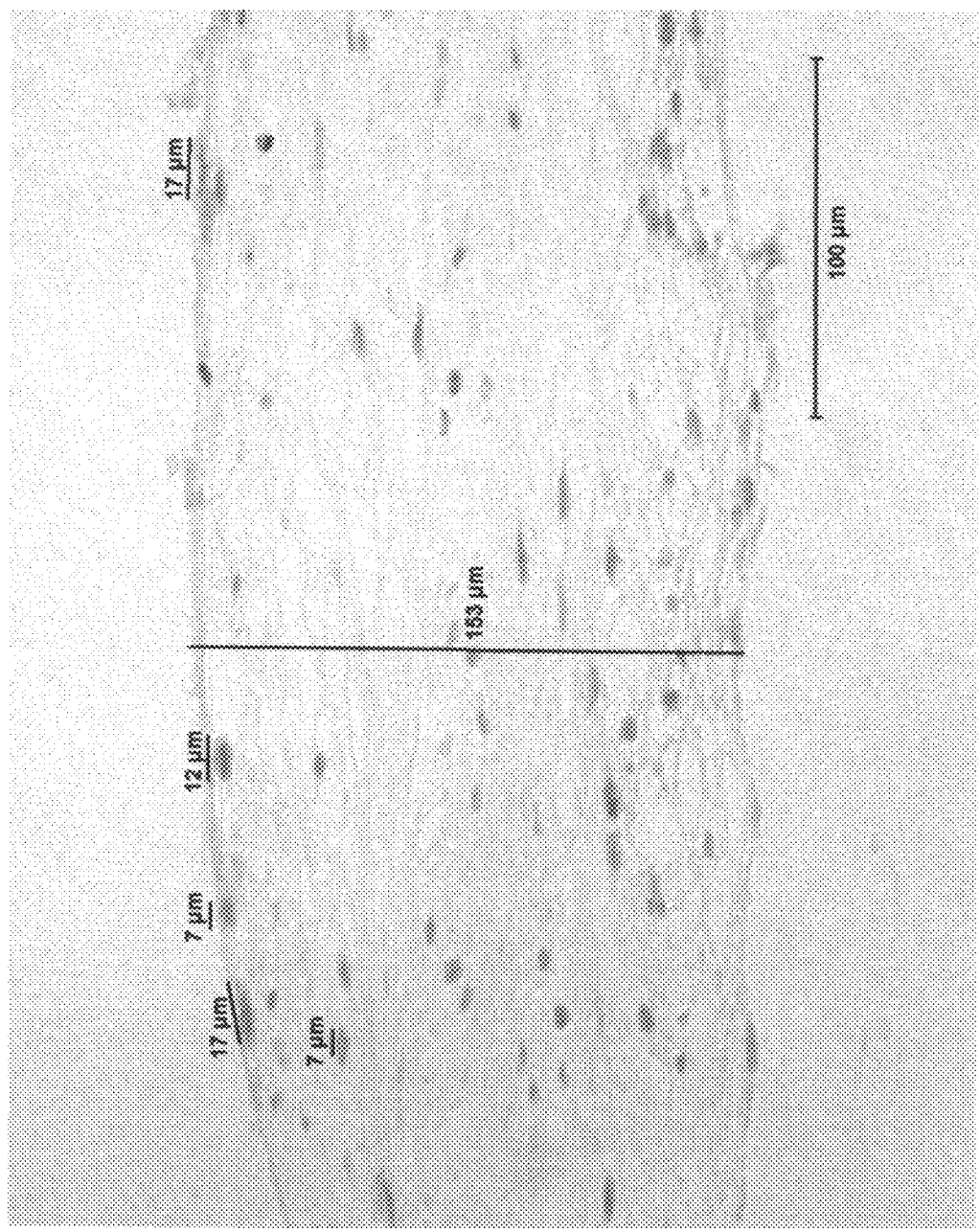
FIG. 7 shows cross-sections of a 24-day fibroblast ALS system about 153 µm thick containing neuronal cells/tissue that are expressing anti-Hu MAb 16A11. The ALS was allowed to grow for 2 weeks prior to seeding with human neuroprogenitor cells. As can be seen, varying-sized regions (different cross-sections of nerve cell bodies) expressing the anti-Hu MAb 16A11 marker are indicated, ranging in size to almost 20 µm.
Figure 8:
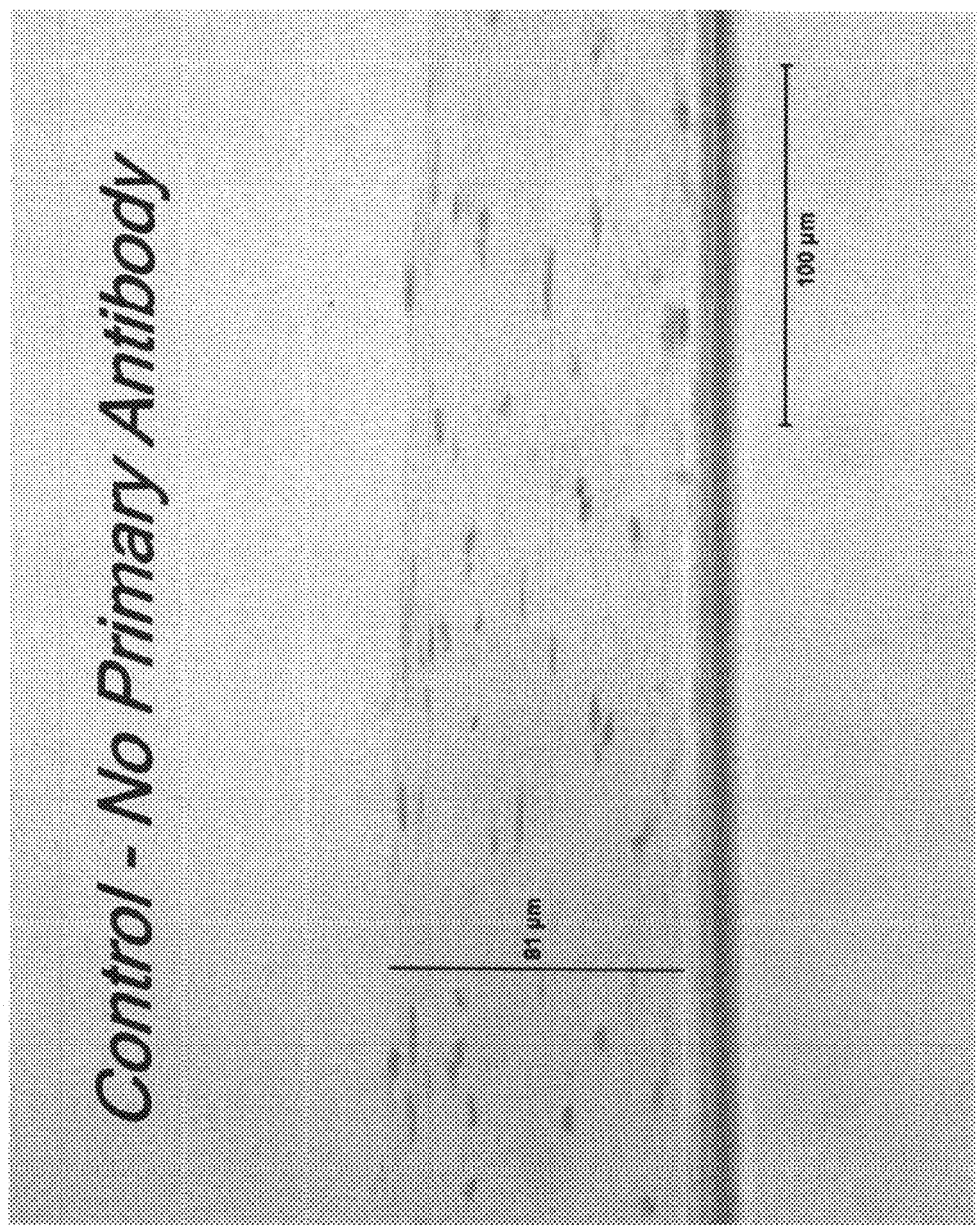
FIG. 8 shows a section view of a negative control system for the neurogenesis marker experiments of FIGS. 3 through 7, where no primary Hu MAb 16A11 antibody was present in the system. Thus, only the nuclei (in blue) of the cells are visible, and no expressed neurogenesis markers are visible.
Figure 9:
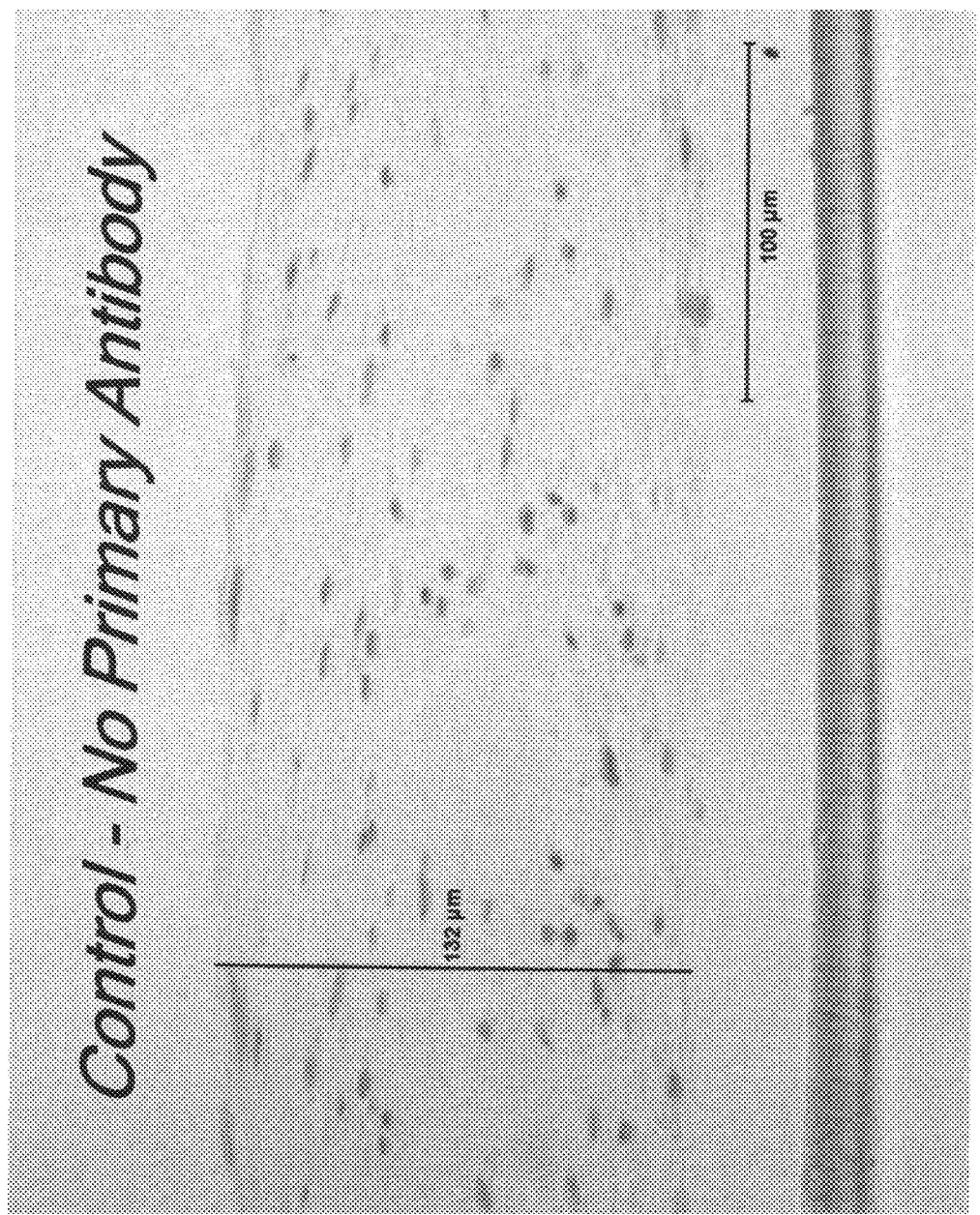
FIG. 9 shows a different section view of a negative control system for the neurogenesis marker experiments of FIGS. 3 through 7, where no primary Hu MAb 16A11 antibody was present in the system. Thus, only the nuclei (in blue) of the cells are visible, and no expressed neurogenesis markers are visible.
Figure 10:
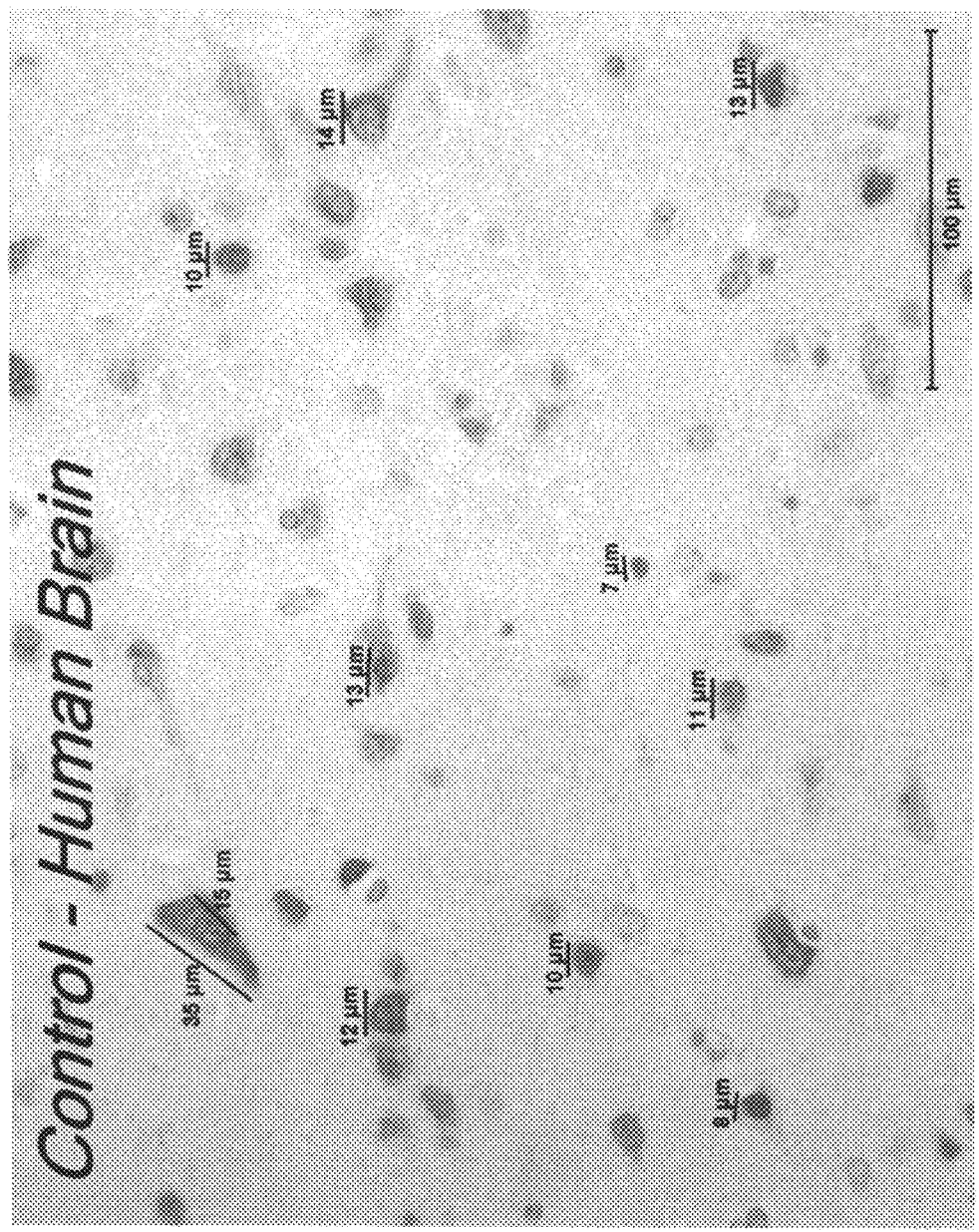
FIG. 10 shows a cross-sectional view of a positive control system for the neurogenesis marker experiments of FIGS. 3 through 7, using human brain sections. Positive indication that the marker anti-Hu MAb 16A11 attaches to nerve cell bodies is indicated by the large and numerous brown dye spots visible throughout the images. Most of the cells that did not stain for anti-Hu MAb 16A11 are glial cells.
Figure 11:
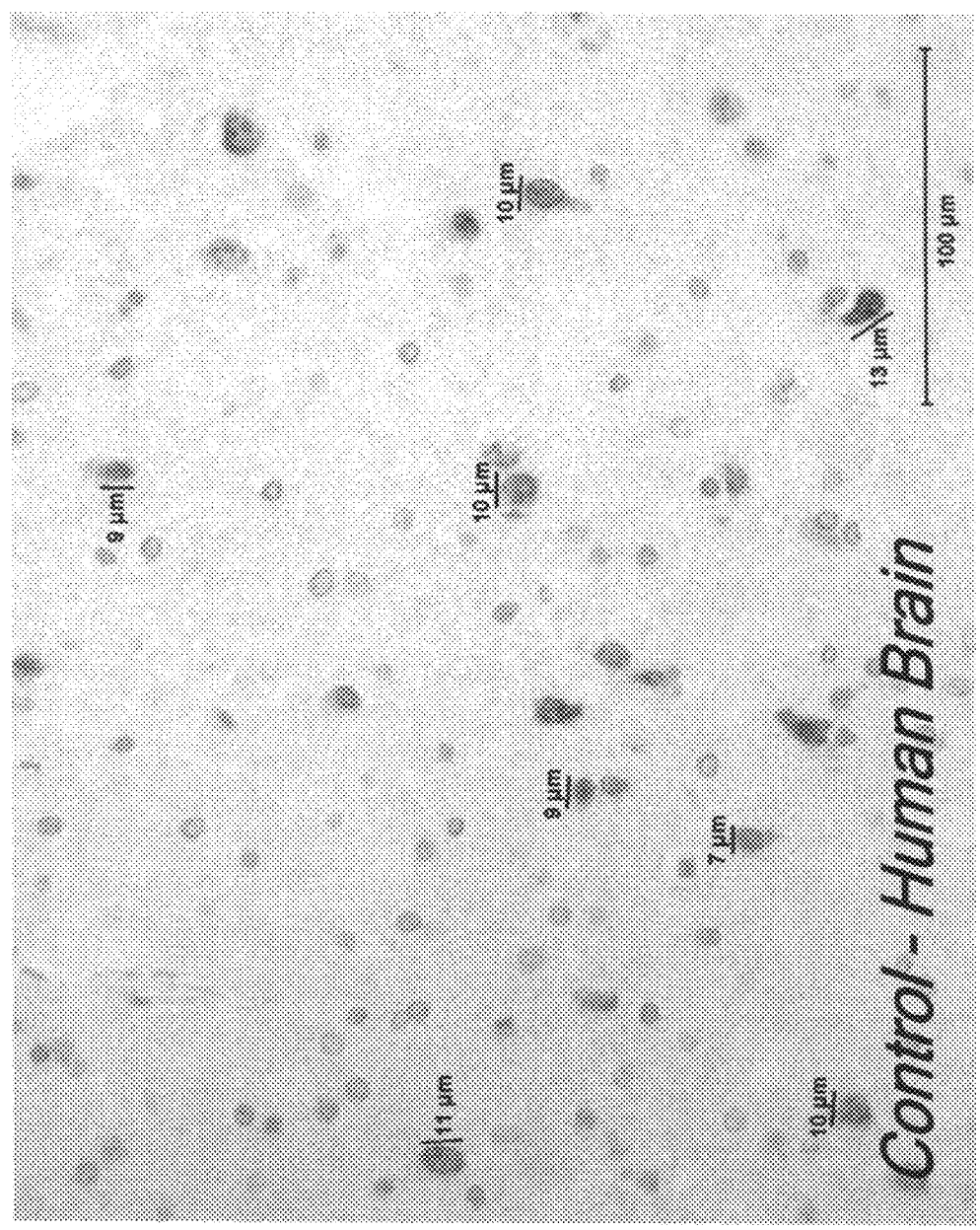
FIG. 11 shows a different cross-sectional view of a positive control system for the neurogenesis marker experiments of FIGS. 3 through 7, using human brain sections. Positive indication that the marker anti-Hu MAb 16A11 attaches to nerve cell bodies is indicated by the large and numerous brown dye spots visible throughout the images. Most of the cells that did not stain for anti-Hu MAb 16A11 are glial cells.

With time and appropriate growth factors, secreted by the fibroblasts in response to the presence of the seeded neural progenitor cells and so present in the ALS (but they may also be added as a supplement), the neural progenitor cells began to differentiate into both nerve cells, as evidenced by formation of nerve axons, and glial cells. Neural progenitor cells implanted into mammalian spinal cord and grown in the absence of an ALS system do not differentiate into both nerve cells and glial cells; they only differentiate into glial cells. But as can be seen in FIG. 2, neural progenitor cells, grown on a fibroblast ALS, have differentiated into both nerve axons and glial cells. Additionally, FIG. 1 shows methylene blue staining of neurons that have differentiated from neural progenitor cells grown on a fibroblast ALS.

FIGS. 3 through 7 show sections of fibroblast ALS systems containing neuronal cells/tissue that are expressing anti-Hu MAb 16A11, an early marker of vertebrate neurogenesis that is expressed shortly after neuronal terminal mitosis. The marker is observed in nerve cell bodies as reddish brown spots; the cell nuclei are blue. As can be seen, varying-sized regions (different cross-sections of nerve cell bodies) expressing the anti-Hu MAb 16A11 marker are indicated, ranging in size from 4 μm to over 20 μm.

Example 4

In Vitro Protocol for Generating Muscle Cells/Tissue

In one embodiment, a large number fibroblast cells (Cambrex CC-2509) were centrifuged, at approximately 1000 rpm for about 8 min, followed by removal of the supernatant. The resulting fibroblasts were then resuspended in fALS Medium and seeded into TRANSWELLS™ or BD FALCON™/BIOCOAT™ Cell Culture Inserts at superconfluency (between about 1,000 cells/mm3 to greater than 200,000 cells/mm3), and fed with fALS Medium every 2-3 days for about 2-3 weeks or longer at hyperconfluent conditions until the desired amount and thickness of ALS had formed.

Figure 12:
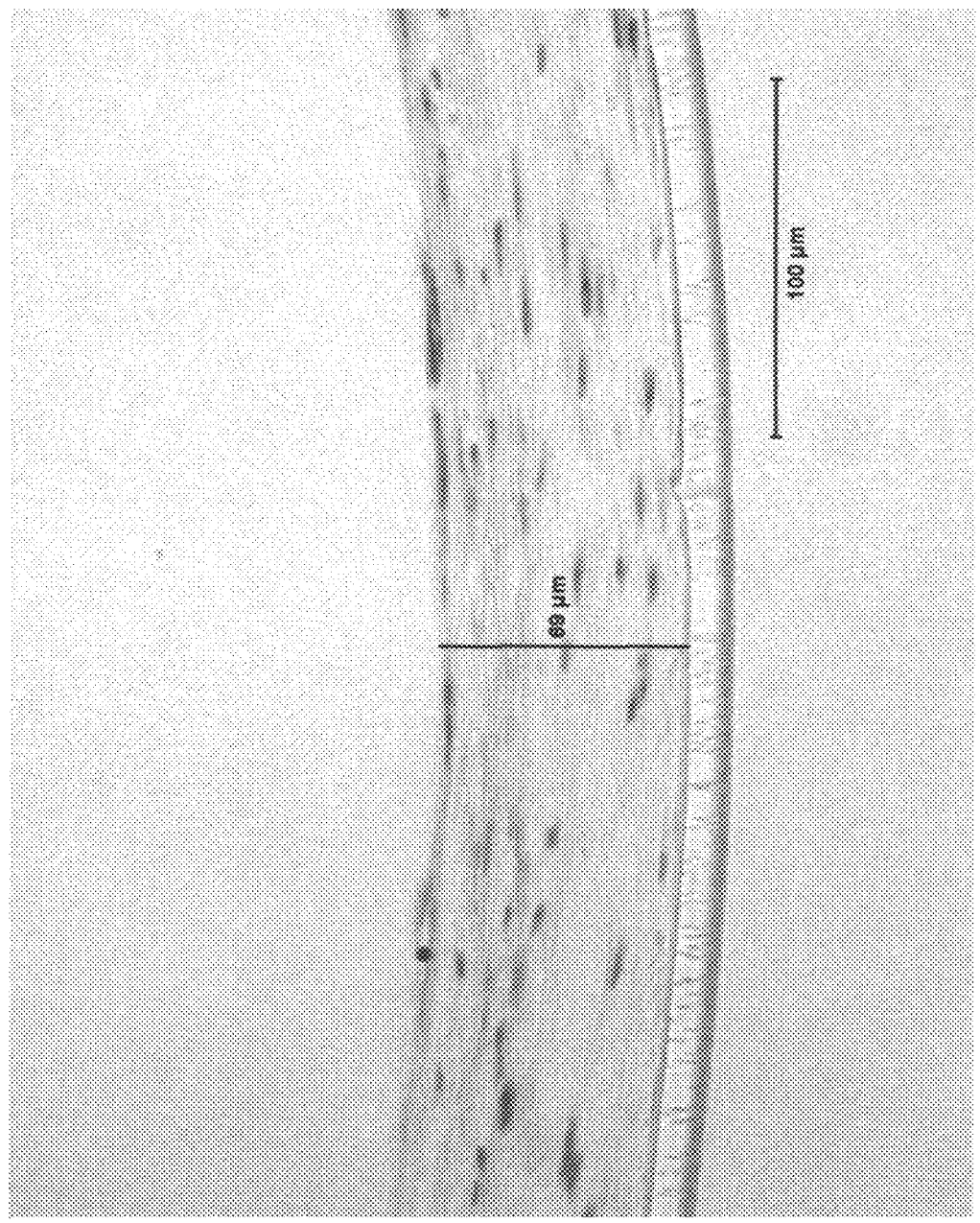
FIG. 12 shows trichrome staining of a cross-section of a 24-day fibroblast ALS system containing muscle cells/tissue about 70 µm thick. The collagen fibers of the ALS are blue; the nuclei of cells are (bluish) black; and muscle cells (differentiated from human skeletal muscle myoblasts seeded onto the ALS 2 weeks earlier) within the ALS are observed as reddish spots within the ALS sections. The ALS was allowed to grow for 1 week prior to seeding with human skeletal muscle myoblasts.
Figure 13:
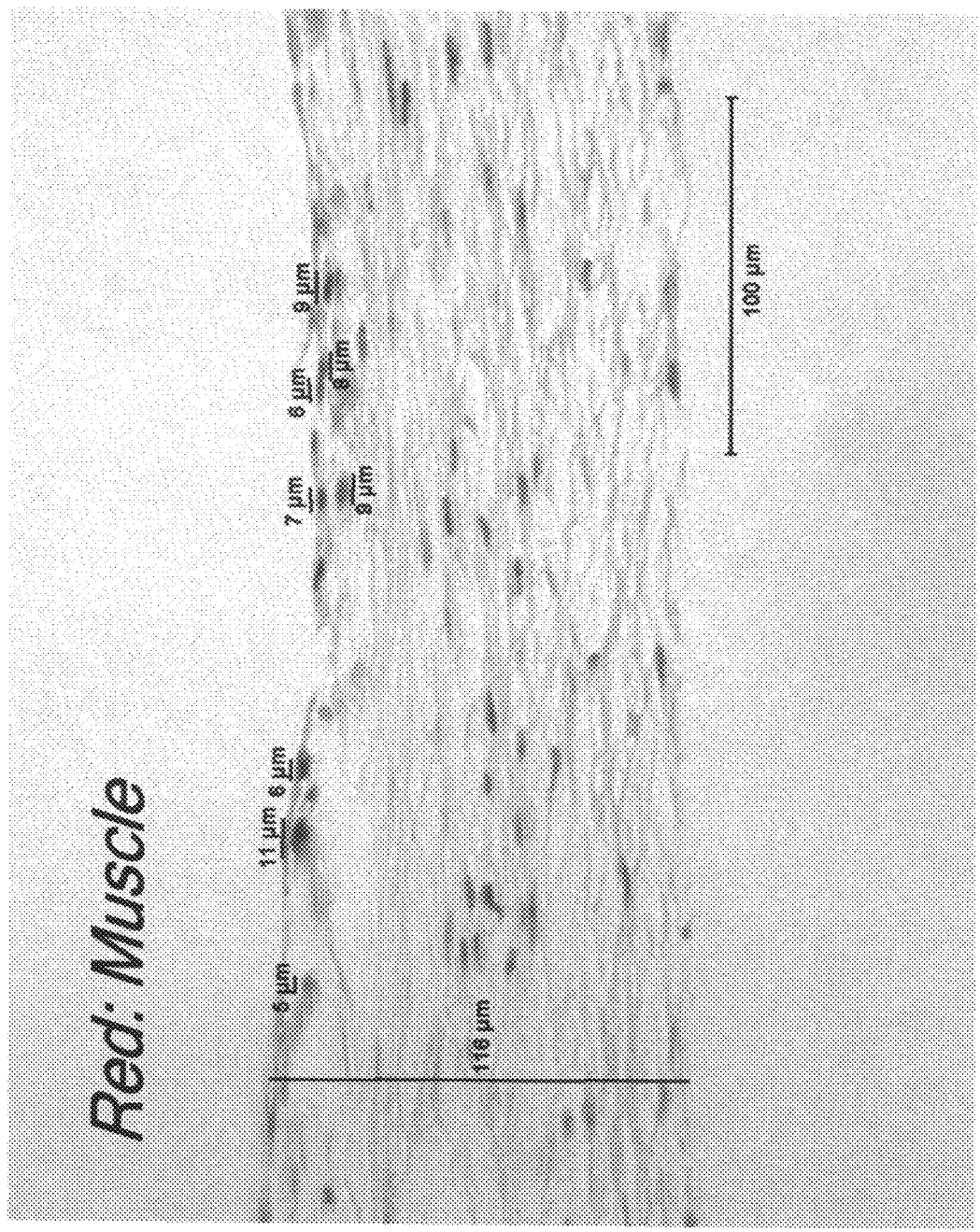
FIG. 13 shows trichrome staining of a different cross-section of a 24-day fibroblast ALS system containing muscle cells/tissue about 115 µm thick. The collagen fibers of the ALS are blue; the nuclei of cells are (bluish) black; and muscle cells (differentiated from human skeletal muscle myoblasts seeded onto the ALS 2 weeks earlier) within the ALS are observed as reddish spots within the ALS sections. The ALS was allowed to grow for 1 week prior to seeding with human skeletal muscle myoblasts.

At this point, the ALS containing fibroblasts and extensive CDM was seeded with human skeletal muscle myoblasts (Cambrex CC-2580), and the basolateral side of the TRANSWELLS™ continued to be fed with ALS Medium while the apical side was fed with Skeletal Muscle Medium (Cambrex CC-3160) every 2-3 days for another 2-4 weeks or longer. With time and appropriate growth factors, secreted by the fibroblasts in response to the presence of the seeded skeletal muscle myoblasts and so present in the ALS (but they may also be added as a supplement), the skeletal muscle myoblasts began to differentiate into skeletal muscle cells. FIGS. 12 and 13 show trichrome staining of two different sections of a fibroblast ALS system containing muscle cells/tissue, one about 70 pm thick (FIG. 12) and the other section about 115 pm thick (FIG. 13). The fibroblast extracellular matrix of collagen fibers are blue; the nuclei of the ALS fibroblast cells are (bluish) black; and the young skeletal muscle cells within the ALS are observed as reddish spots within the ALS sections.

Example 5

In Vitro Protocol for Generating Liver Tissue

In one embodiment, a large number fibroblast cells (Cambrex CC-2509) were centrifuged, at approximately 1000 rpm for about 8 min, followed by removal of the supernatant. The resulting fibroblasts were then resuspended in fALS Medium and seeded into TRANSWELLS™ or BD FALCON™/BIO-COAT™ Cell Culture Inserts at superconfluency (between about 1,000 cells/mm3 to greater than 200,000 cells/mm3), and fed with fALS Medium every 2-3 days for about 2-3 weeks or longer at hyperconfluent conditions until the desired amount and thickness of ALS had formed.

At this point, the ALS containing fibroblasts and extensive CDM was seeded with human hepatocytes (Cambrex CC-2591), and the basolateral side of the TRANSWELLS™ continued to be fed with fALS Medium while the apical side was fed with Hepatocyte Medium (Cambrex CC-3198) every 2-3 days for another 2-4 weeks or longer. With time and appropriate growth factors, secreted by the fibroblasts in response to the presence of the seeded hepatocytes and so present in the ALS (but they can also be added as a supplement), the hepatocytes began to differentiate into albumin-secreting liver cells and tissue.

Example 6a

In Vivo Protocol for Generating/Regenerating Neuronal Tissue Using In Vitro ALS Systems Seeded with Neural Progenitor Cells Rat/Rodent Spinal Cord In one embodiment of the present invention, the lower spinal cord of an adult nude Fisher rat is partially severed under general anesthesia (a complete and full 5 mm long spinal cord transection) such that the rat is paralyzed from below the point of injury (the site of injury is chosen such that the lower limbs are non-functional after excision—generally T9-T10). Neuronal cells/tissue generated in vitro within a fibroblast ALS system seeded with human neural progenitor cells or neuroblastomas or neuronal stem cells or other primary neural cell line, such as detailed in Example 3, are next implanted into the rat spinal cord at the site of injury.

The fibroblasts within the ALS begin attaching to the site of implantation immediately, and continue attaching for days and weeks, as the neuronal cells grow and form active neural connections with existing nerves on each side of the implantation site. Any remaining primary neurons at the time of implantation appear to differentiate into functional nerve cells and tissue. The rat is maintained and observed for 8 weeks or longer, and observed for indications of neurogenesis, such as the ability to move its hind legs, or even the ability to walk with erratic use of its hind legs, or the ability to walk using its hind legs for a short a distance. Experiments have so far resulted in experimental animals regaining sensation and movement corresponding to up to 14 on the BBB scale, as compared to an average of 2 on the BBB scale for control animals.

6b

In Vivo Protocol for Generating/Regenerating Neuronal Tissue Using In Vitro LTM Systems where the Fibroblasts within the LTM are Transdifferentiated into Neurons Rat/Rodent Spinal Cord In one embodiment of the present invention, the lower spinal cord of an adult nude Fisher rat is partially severed under general anesthesia (a complete and full 5 mm long spinal cord transection) such that the rat is paralyzed from below the point of injury (the site of injury is chosen such that the lower limbs are non-functional after excision—generally T9-T10). Neuronal cells/tissue generated in vitro within an LTM by transdifferentiating the fibroblasts within the LTM into neurons (by placing the LTM in Neurogen media with cytochalasin B for 60 h, followed by replacing the media with fresh Neurogen media for 2-3 days) are next implanted into the rat spinal cord at the site of injury.

The neuronal cells within the LTM grow and form active neural connections with existing nerves on each side of the implantation site over several weeks. Remaining neurons on each side of the transection site appear to also start growing into the LTM over several weeks. The rat is maintained and observed for 8 weeks or longer, and observed for indications of neurogenesis, such as the ability to move its hind legs, or even the ability to walk with erratic use of its hind legs, or the ability to walk using its hind legs for a short a distance. Experiments have so far resulted in experimental animals regaining sensation and movement corresponding to up to 16 on the BBB scale, as compared to an average of 2 on the BBB scale for control animals.

6c

In Vivo Protocol for Treating Spinal Cord Degeneration in an Animal

Fibroblast cells from human foreskin are cultured to produce an ALS or LTM system having an extensive ECM, as detailed in Example 2. The ALS is then seeded with neural progenitor cells or neuroblastomas or neuronal stem cells or other primary neural cell line as described in Example 3, or the fibroblasts within the LTM are transdifferentiated into neurons as in example 6b, until nerve cells and/or tissue are evident. The ALS plus primary neural cells/tissue or neuronal LTM is next implanted into the animal's spinal cord near or at the site of degeneration, or at several sites along the spinal cord if degeneration is pervasive.

The treated animal is then maintained and observed for 8 weeks or longer, as required, while monitoring for evidence of spinal cord regeneration, such as new-found movement, feeling and sensation. Several treatments with neuronal LTM or ALS systems having primary neural cells and/or tissue may be performed, to increase the spinal cord regeneration seen, depending upon the severity of degeneration in the animal to be treated.

Such a procedure may be used on animals, including humans, suffering from a wide-spectrum of neurodegenerative diseases such as Lou Gehrig's disease, Huntington's disease, spinal cord compression due to crushed vertebrae, spinal cord severance, etc.

7

In Vivo Protocol for Generating/Regenerating Cartilage Tissue Using In Vitro ALS Systems Seeded with Chondrocytes In one embodiment, a large number fibroblast cells were centrifuged, at approximately 1000 rpm for about 8 min, followed by removal of the supernatant. The resulting fibroblasts were then resuspended in ALS Medium and seeded into TRANSWELLS™ or BD FALCON™/BIOCOAT™ Cell Culture Inserts at superconfluency (between about 1,000 cells/mm to greater than 200,000 cells/mm3), and fed with ALS Medium every 2-3 days for about 2-3 weeks or longer at hyperconfluent conditions until the desired amount and thickness of ALS had formed. The ALS containing fibroblasts and extensive CDM was then seeded with chondrocytes (Cambrex CC-2550), and the basolateral side of the TRANSWELLS™ continued to be fed with ALS Medium while the apical side was fed with Chondrocyte Medium (Cambrex CC-3216) every 2-3 days for another 4-6 weeks or longer. With time and appropriate growth factors, secreted by the fibroblasts in response to the present of the seeded chondrocytes and so present in the ALS (but supplemental factors can also be added as required or desired), the chondrocytes began to differentiate into cartilage tissue.

The Autogenic Living Scaffold may also be first grown into specific shapes by molds, and may also be reshaped to some degree. For example, a "balloon" or hollow disc of a Fibroblast Autogenic Living Scaffold may be prepared by growing the fALS culture around a Teflon disc or sphere with a thin coating of an easily degradable protein or other substance and then slitting one side to remove the disc or sphere and thereby creating the hollow space or "balloon" shape. After preparation of the ALS "mold", it may be filled with chondrocytes in a gel (such as an alginate gel) that may be placed/injected into the open inner space of the ALS disc or balloon mold, and then closed back up to create dense, compact cartilage tissue over time. The ALS allows nutrients and gases to pass through it to the chondrocytes, while at the same time retaining most of the signaling molecules secreted by the chondrocytes and secreting certain growth factors and substances that promotes the formation of functional cartilage tissue. The high tensile strength of the Fibroblast ALS also creates mechanical stresses onto the chondrocytes and newly formed cartilage that promotes the development of functionally strong cartilage. The outside layer of ALS around the formed cartilage disc also promotes the attachment and integration of the cartilage disc once it is implanted. Such a procedure may be used to create, for example, cartilage discs for replacement within a vertebrate spinal column.

Any desired shape or size may be made by creating the appropriate ALS mold, and the resulting cartilage tissue formed within the ALS mold may be used to treat an animal, including a human, suffering from cartilage damage. The same is true of bone damage, where osteoblasts are used instead. In such treatments, the ALS mold plus interior seeded connective tissue cells, or plus interior cartilage tissue, is placed/inserted into the animal's joint, or placed/inserted near or at the site of injury where cartilage regeneration is desired, or at several sites.

The treated animal is then maintained and observed for several weeks and months or longer, as required, while monitoring for evidence of cartilage regeneration by using MRI imaging or other soft-tissue detection techniques, and by observation of physical indications such as joint function, levels of pain, strength, flexibility, etc. Several treatments with ALS molds and seeded chondrocytes may be performed, to increase the cartilage regeneration seen, depending upon the severity of the injury or cartilage degeneration in the animal to be treated.

Such a procedure may be used on animals, including humans, suffering from a wide-spectrum of cartilage degeneration conditions such as cartilage degradation/degeneration in the joints, including knees, ankles and fingers, in the spinal column, and in the nose, ear, throat, and elsewhere.

8

Living Tissue Matrix (LTM)

A strong and thick cell-produced Living Tissue Matrix (LTM) can be produced within three weeks, making it a viable and attractive alternative to reconstituted gels, such as cell-populated fibrin or collagen gels. Data from comparative studies show that a completely cell-produced ECM is mechanically superior to reconstituted ECM, and more closely resembles native in vivo ECM than reconstituted ECM. This strength is highly correlated to the fraction of very stable collagen. In addition to closely approximating native generating/regenerating tissue, LTMs also support significantly faster rates of cell adhesion, migration, proliferation, differentiation, and acquisition of in vivo-like morphology than reconstituted ECM. The extracellular matrix (ECM) portion of the LTMs consists of several components such as collagen I, collagen III, fibronectin, proteoglycans, sulfated glycosaminoglycans, hyaluronic acid, and decorin.

Extensive preliminary studies have indicated that these matrices are composed of numerous extracellular matrix proteins in amounts, ratios and arrangement that more closely resemble young, native, blastema-like tissue than any other matrices or scaffolds currently in existence. These matrices are embedded with multi-layered fibroblasts that created the LTM in the first place. Dedifferentiating these multi-layered fibroblasts in the matrix could essentially lead to a blastema-like structure that can be implanted onto the site of tissue injury for restoration of a functional multi-tissue type structure. Transdifferentiating some or all of these multi-layered fibroblasts in the matrix could then aid the blastema-like structure so formed to start developing and differentiating along a more controlled pathway.

Figure 14:
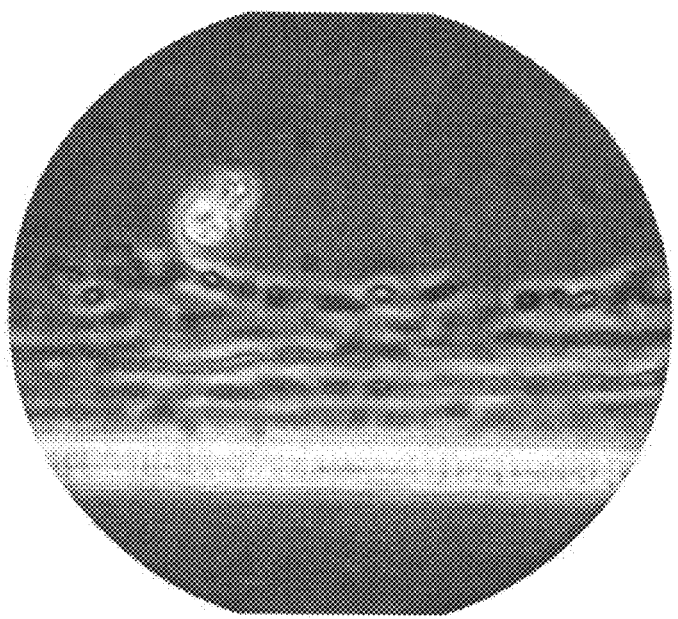
FIG. 14 shows early nerve differentiation on Living Tissue Matrix. Human neural cell bodies stained with Hu16A11 (brown), a marker of early neurogenesis.
Figure 15A:
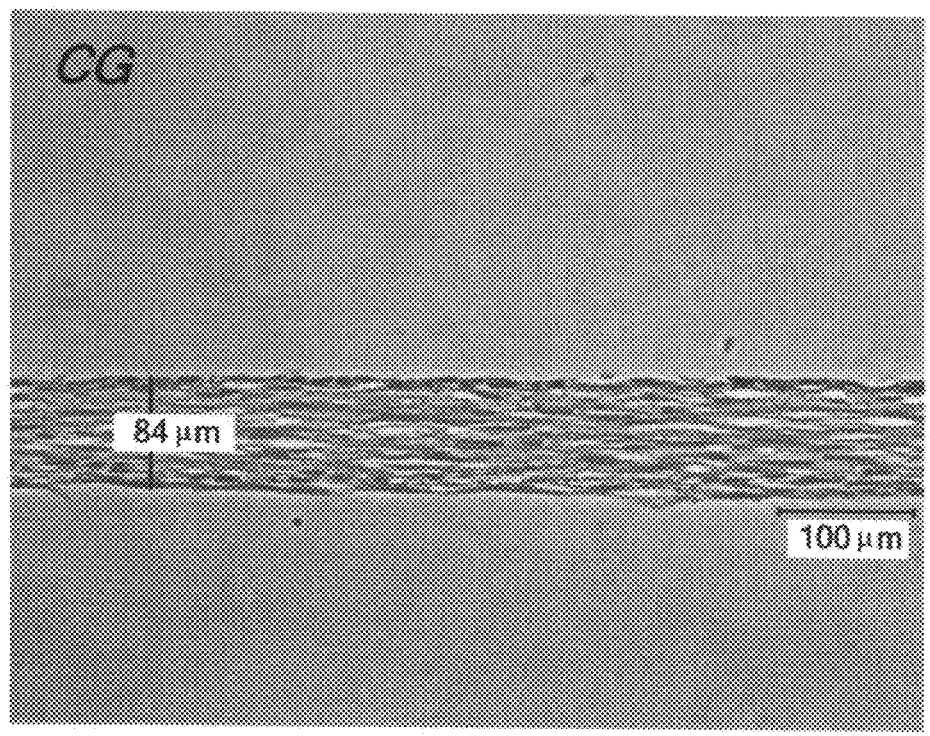
FIG. 15A shows Hematoxylin and Eosin (H&E) stained sections of fibroblast-populated collagen gel (CG), 84 µm thick, as measured by digital image analysis.
Figure 15B:
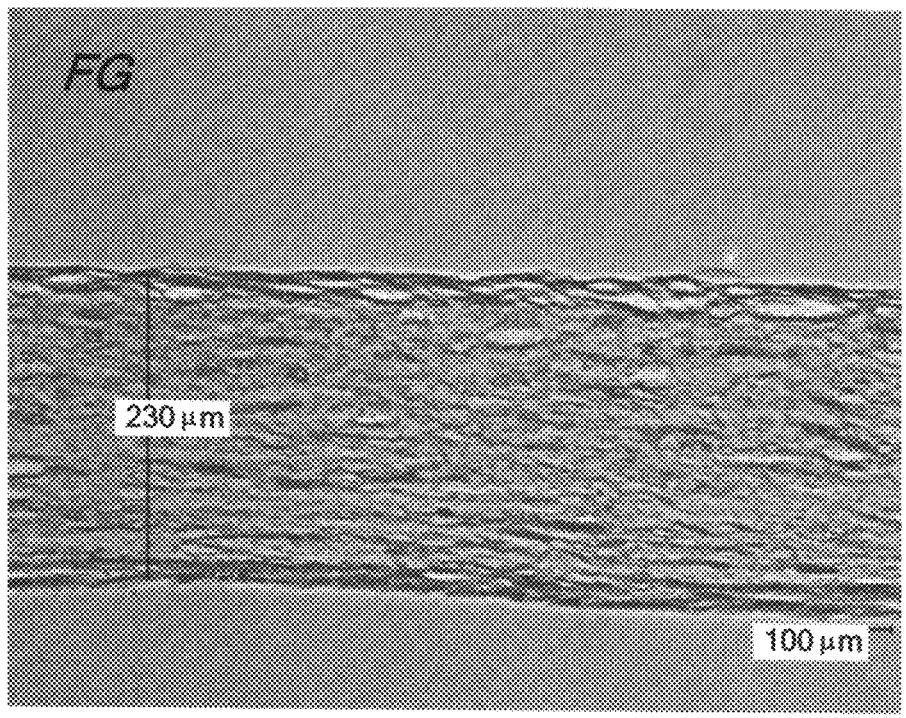
FIG. 15B shows fibroblast-populated fibrin gel (FG), 230 µm thick, as measured by digital image analysis.
Figure 15C:
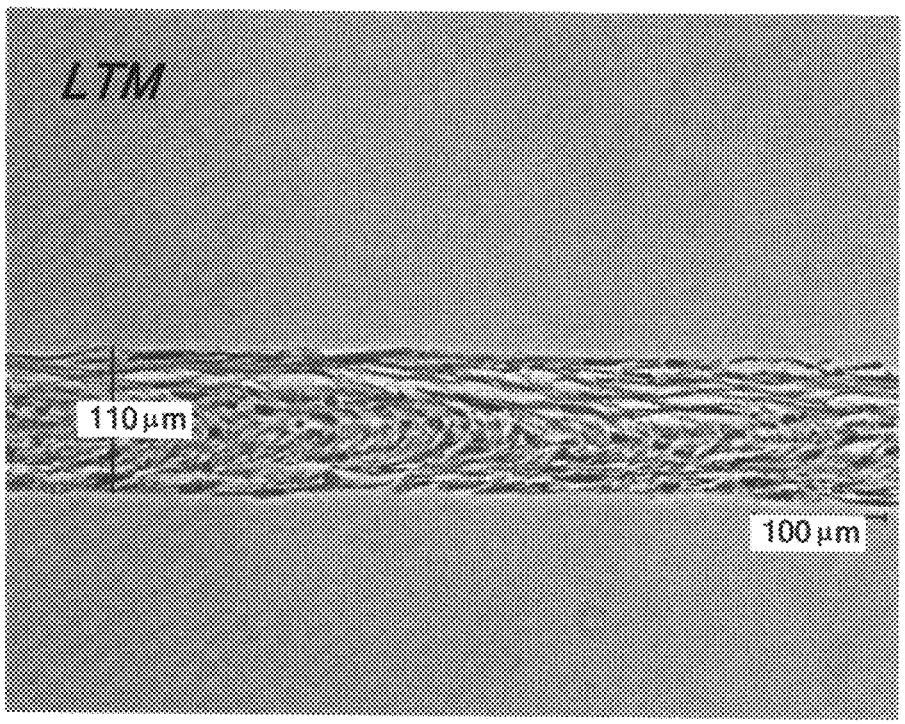
FIG. 15C shows Living Tissue Matrix (LTM) fed with the same serum-supplemented media that the CG and FG above were fed with, 110 µm thick, as measured by digital image analysis.
Figure 15D:
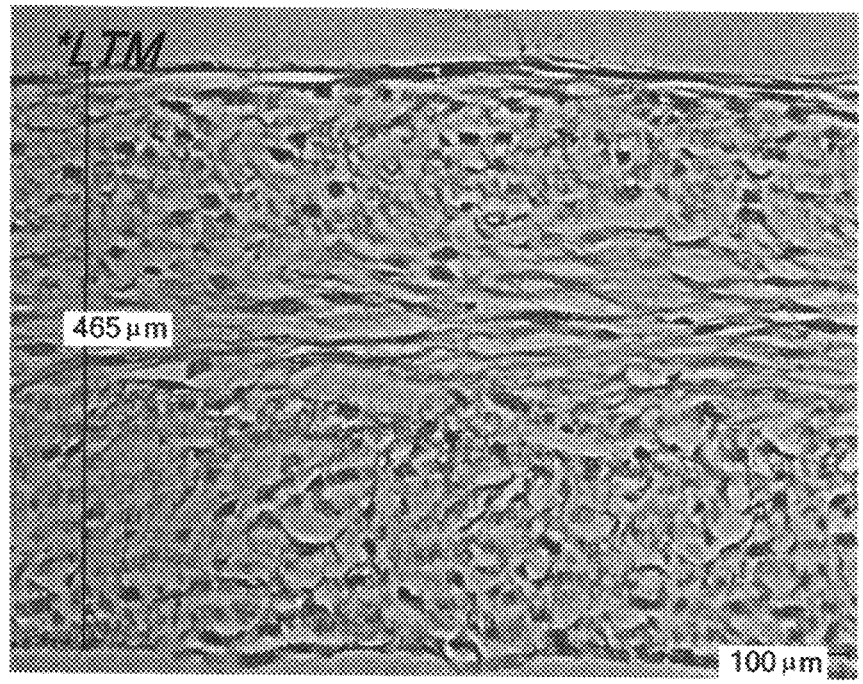
FIG. 15D shows Living Tissue Matrix (*LTM) fed with Matrix Media, 465 µm thick, as measured by digital image analysis.
Figure 15E:
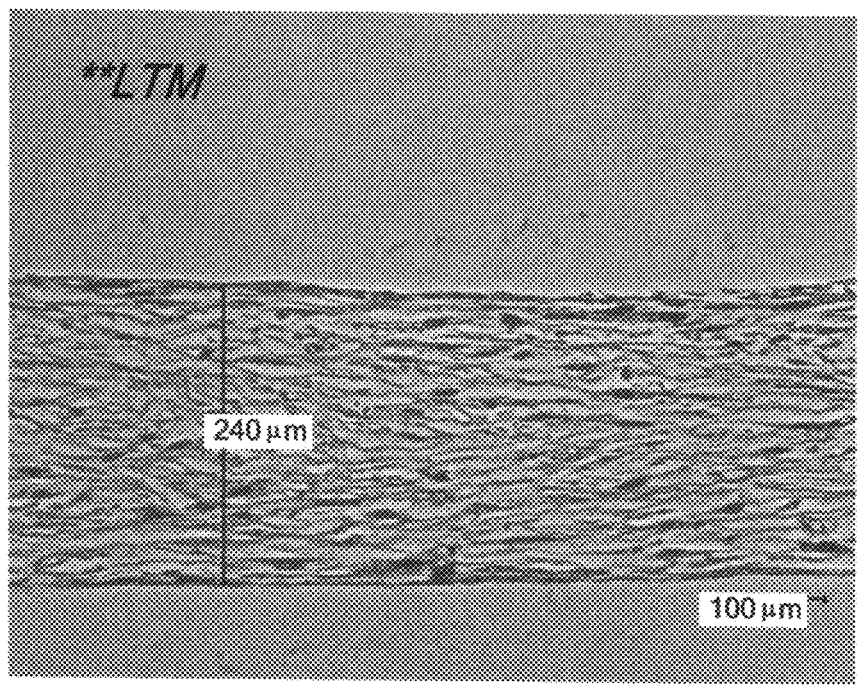
FIG. 15E shows Living Tissue Matrix (**LTM) fed with a modified Matrix Media, 240 µm thick, as measured by digital image analysis. All micrographs for FIGS. A-E were taken at 200×. Scale bars=100 µm.

FIG. 14 shows an H&E stained cross-section of early nerve differentiation on cell-produced Living Tissue Matrices. Human neural cell bodies having Hu16A11 markers (a marker of early neurogenesis) as visible, with the stained markers discernable as dark (brown) stained regions in the neural cell bodies.

9

Genetically Engineering Fibroblasts to Make a Stronger and Thicker ALS or LTM

A human gene coding for fibroblast growth factor 2 (FGF-2) was inserted into the genome of human neonatal foreskin fibroblasts (obtained from the American Type Culture Collection (ATCC, Manassas, Va.)) under the regulation of a β-actin promoter. These transformed or genetically engineered fibroblasts, produced a significantly stronger and thicker cell-derived matrix than control fibroblast cultured for a 3-week period according to the methods of example 2. The genetically engineered fibroblasts were found to secrete several-fold higher concentrations of FGF-2 into the extracellular space of the ALSs or LTMs than the wild-type fibroblasts. These higher FGF-2 concentrations caused an increase in the rate of extracellular matrix protein synthesis by the fibroblasts within the ALSs or LTMs.

10

Methods for Preparing and Analyzing Living Tissue Matrices (LTMs) or Autogenic Living Scaffolds (ALSs) and their Cell-Derived Matrix (CDM) Component Versus Fibroblast-Populated Collagen Gels and Fibrin Gels A. Cells Human neonatal foreskin fibroblasts (HFFs, American Type Culture Collection, Manassas, Va.) were cultured in T-300 tissue culture flasks (BD Biosciences, Bedford, Mass.) with high glucose Dubelco's modified Eagle' medium (DMEM, Mediatech, Herndon, Va.) supplemented with 10% bovine calf serum (BCS, Hyclone, Logan, Utah), and 1% penicillin/streptomycin/ampothericin B (Invitrogen, Carlsbad, Calif.) at 37° C. in humidified, 10% $CO_2$ conditions. Cells were harvested at 90% confluency with a 10 min application of 0.25% trypsin/0.05% EDTA solution (Mediatech). Two million, passage 5 cells were used for each sample in all experiments.

B. Standard Serum-Supplemented Medium

DMEM with 10% fetal bovine serum (FBS, ATCC), 150 μg/ml (519 μM) L-ascorbic acid phosphate magnesium salt n-hydrate (Wako Pure Chemicals, Japan), and 1% penicillin/streptomycin/amphotericin B (Invitrogen).

C. Chemically-Defined Medium

A 3:1 ratio of DMEM (high glucose (4.5 g/L); with L-glutamine and sodium pyruvate (Mediatech) and Ham's F12 (Invitrogen) with the addition of 5 μg/ml insulin (Sigma-Aldrich, St. Louis, Mo.), 5 ng/ml selenious acid (Sigma-Aldrich), $10^{-4}$ M ethanolamine (Sigma-Aldrich), 150 μg/ml L-ascorbic acid phosphate magnesium salt n-hydrate (Wako), 2.5 ng/ml epidermal growth factor (EGF (BD Biosciences)) in 5 μg/ml human serum albumin, EMD (Biosciences, San Diego, Calif.), 5 ng/ml basic fibroblast growth factor (bFGF (BD Biosciences $1.0 \times 10^{-7}$ M dex-amethasone (Sigma-Aldrich), $2 \times 10^{-10}$ M L-3,3',5-triiodothyronine (Sigma-Aldrich), $4 \times 10^{-3}$ M L-analyl-L-glutamine (GLUTAMAX™) (Invitrogen), 1 μg/ml glutathione (reduced) (Sigma-Aldrich), and 1% penicillin/streptomycin/amphotericin B (Invitrogen). Growth factors were added fresh at each feeding, except for **CDM, where the growth factors were added at the correct concentration (2.5 ng/ml EGF and 5.0 ng/ml bFGF) into the entire stock medium at the start of the experiment.

D. Collagen Gel, Fibrin Gel and ALS/LTM Preparation

Fibroblast-populated collagen gels (CGs) were prepared according to methods known in the art by mixing 0.2 ml of collagen stock solution (5 mg/ml of 5 mM HCl-extracted rat tail tendon collagen in 5 mM acetic acid), 0.05 ml 5X DMEM (Mediatech), 0.65 ml DMEM (Mediatech) with cells, 0.1 ml fetal bovine serum (FBS, ATCC), 150 μg L-ascorbic acid phosphate magnesium salt n-hydrate (Wako) and 1% penicillin/streptomycin/amphotericin B (Invitrogen) at room temperature. One milliliter of the resulting solution was added into each 24 mm diameter well. The initial collagen concentration was 1.0 mg/ml, and the initial cell concentration was 2,000,000 cells/ml in 10% FBS.

Fibroblast-populated fibrin gels (FGs) were prepared based on the methods known in the art. Briefly, HFFs in standard serum-supplemented medium were added to a fibrinogen solution (Sigma-Aldrich F4753 type IV). One-ml samples were mixed with 4 units of bovine thrombin (Sigma-Aldrich, T7513) at room temperature. One milliliter of the resulting solution was added into each 24 mm diameter well. The initial fibrinogen concentration was 1.0 mg/ml, and the initial cell concentration was 2,000,000 cells/ml in 10% FBS.

ALSs/LTMs were prepared by mixing the 2 million, passage 5 HFFs with standard serum-supplemented medium or the chemically-defined medium described above (for *CG, *CDM and **CDM) at room temperature into a final volume of 1 ml per sample. The initial cell concentration was 2,000,000 cells/ml in 10% FBS. The 1 ml samples of collagen gels, fibrin gels, and CDMs were pipetted onto 24 mm diameter, porous inserts (0.4 pm TRANSWELLS™, Corning Life Sciences, Acton, Mass.) suspended above standard 6-well plates, and allowed to sit undisturbed at room temperature. After a 1-hour period, 3 ml of standard serum-supplemented medium or chemically-defined medium (for *CD, *CDM and **CDM) was carefully added below, and 1 ml added above, each sample and the samples were incubated at 37° C. in humidified, 10% CO, conditions. Samples were fed every other day (3 ml below and 2 ml above each porous insert) with the same medium for 3 weeks.

E. Mechanical Testing

After 3 weeks in culture, the samples were exposed to $ddH_2O$ for 1 hour to lyse the cells and eliminate the contractile forces produced by the fibroblasts, and then equilibrated in phosphate buffered saline (PBS, Mediatech) for biomechanical testing. The human penile skin was obtained through Analytical Biological Serives Inc. (Wilmington, Del.) and shipped cold in RPMI medium with antibiotics and tested within 12 h of removal from the subject. The thickness, failure tension, failure strain, and ultimate tensile strength (UTS) of the samples were determined by a novel tissue inflation device that measures the displacement and pressure at which a sample bursts when inflated with PBS at a constant rate of 1 ml/min. The sample is circularly clamped at and inflated through a 1-cm diameter opening, thus causing the sample to form a spherical cap before failing. The increasing pressure applied to the sample was measured by an on-board pressure transducer (model PX102-025GV, Omega Engineering, Stamford, Conn.). The displacement of the center of the cap was measured with a laser displacement system (LDS-080, Keyence, Woodcliff Lake, N.J.). The LSD-080 also measured the thickness of each sample after being slightly compressed by a small reflective disk (1.3 g, 1.3 cm diameter) for 1 minute. The maximum membrane tension, T, was calculated using the Law of Laplace for a spherical membrane:

$$T = \tfrac{1}{2}PR, \quad (eq. 1)$$

where P is the pressure when the tissue bursts and R is the corresponding radius at the point of rupture, calculated assuming a spherical cap geometry by:

$$R = (w^2 + a^2)/2w, \quad (eq. 2)$$

where a is the radius of the clamp (5 mm) and w is the displacement at the center of the sample at failure measured by the laser.

The ultimate tensile strength (UTS) was calculated by:

$$UTS = T/t, \quad (eq. 3)$$

where t is the initial thickness of the specimen before inflation. The actual thickness at the time of bursting was less than this value. Thus the calculated UTS (engineering stress) is less than the true stress at failure, since the thickness of the specimens decreased as they were being inflated.

The ultimate tensile strength per collagen density (UTS/Collagen Density) was calculated by:

$$UTS/\text{Collagen Density} = UTS/(\text{Total Collagen}/\pi t(D/2)^2) \quad (\text{eq. 4})$$
$$= T/(\text{Total Collagen}/\pi(D/2)^2),$$

where D is the diameter of the constructs (2.4 cm).

The failure strain was determined from the equibiaxial strain at the pole estimated from the displacement data using the approximate relationship:

$$\text{Failure Strain} = \tfrac{2}{3}(w/a)^2 - \tfrac{2}{15}(w/a)^4 + \tfrac{2}{35}(w/a)^6. \quad (\text{eq. 5})$$

F. Biochemical Analysis

Following biomechanical testing, the samples were weighed (wet weight), lyophilized overnight, and then weighed again (dry weight). Each lyophilized sample was solubilized in 1 ml of 0.5 M acetic acid and 1 mg/ml pepsin (Sigma-Aldrich) and incubated overnight at 20° C. with rotation. This extraction step was repeated twice to achieve complete extraction of the acid and pepsin soluble fraction of collagen. The samples were then centrifuged at 14,000 rpm for 1 hour at 15° C., and the supernatant was combined with samples from the other two extractions and used for determining non-acid and pepsin extractable collagen content using the SIRCOL™ Assay (Biocolor, Belfast, N. Ireland). The SIRCOL™ Assay quantified the content of intact collagen monomers in the solution, and did not detect degraded collagen (these amounts were 5-10% of the actual collagen content (data not shown) determined by a hydroxyproline assay (see methods below)). Total non-collagenous protein content of each extract was determined with the TP-BLUE™ Total Protein Assay (Biocolor) using Coomassie brilliant blue G. Total protein content was obtained by adding this value to the total amount of collagen obtained for each sample. The remaining pellets of each sample were digested with Proteinase K (Invitrogen), 50 µg in 500 µl solution of 10 mM EDTA and 0.1 M sodium phosphate (pH 6.5) (Fisher) overnight at 60° C. A 100 µl aliquot of the digest was used for determining sulfated glycosaminoglycan and proteoglycan content (that did not include hyaluronic acid) with the BLYCAN™ Assay (Biocolor). A 10 µl aliquot of the digest was then used to determine DNA content, and thus cell number (assuming 8 pg of DNA per cell), with Hoechst 33258 dye (Amersham Biosciences, Piscataway, N.J.) on a DNA Quant 200 fluorometer (Amersham Biosciences). 100-200 µl aliquots of the Proteinase K digests were used to determine the non-acid and pepsin extractable collagen content (insoluble collagen fraction) with a hydroxyprofine assay. The hydroxyproline assay was based on the methods of Edwards and O'Brien (1980) and consisted of hydrolyzing each sample in 6.0 M HCl for 16 hours at 110° C., followed by drying of the samples under vacuum, reconstituting to 2.0 ml with assay buffer (consisting of 5 g/l citric acid (Sigma-Aldrich), 1.2 ml/i glacial acetic acid (EMD Chemicals, Gibbstown, N.J.), 12 g/l sodium acetate (VWR, Bridgeport, N.J.), and 3.4 g/l sodium hydroxide (VWR)), mixing with 1.0 ml of Chloramine-T reagent (made from 62 mM chloramine-T solution (VWR) in 20.7% ddH20, 26% n-propanol (VWR) and 53.3% of assay buffer) for 20 minutes at room temperature, adding 1.0 ml of freshly prepared dimethylaminobenzaldehyde reagent (made from 15 g of p-dimethylaminobenzaldehyde (Sigma-Aldrich) in 60 ml of n-propanol (VWR) and 26 ml of 60% perchloric acid (VWR)) and incubating each sample at 60° C. for 15 minutes, cooling each sample in tap water for 5 minutes, and measuring the absorbance of each sample at 550 nm within 45 minutes. Absorbance readings were correlated with collagen amount using a standard curve and a conversion factor of 10 µg collagen to 1 µg 4-hydroxyproline. The standard curve was created and the conversion factor determined with known amounts of Trans-4-hydroxy-L-proline (Sigma-Aldrich) and rat tail type I collagen.

G. Histology and Transmission Electron Microscopy

One sample from each group was prepared for histological evaluation by fixing in 10% zinc formalin (VWR) for 1 hour, followed by washing and storing in 4° C. ethanol (VWR). The samples were embedded onto paraffin blocks, sectioned into 10 µm thick sections, and stained with hematoxylin and eosin (H&E). The stained sections were imaged and photographed at 200× with a Nikon Eclipse E600 microscope and Spot digital camera (Diagnostic Instruments, Sterling Heights, Mich.). One sample from each group (except **CDM and penile dermis) was fixed for transmission electron microscopy (tEM) according to the methods of Gibson and Lang (1979). Briefly, the samples were fixed in 2% glutaraldehyde for 1 hour, rinsed 3 times in sodium cacodylate buffer, fixed in osmium tetroxide for 10 minutes, and dehydrated in 10 minute ethanol (VWR) steps followed by two washes in propylene oxide (all from Electron Microscopy Sciences, Hatfield, Pa.). The samples were then embedded in epon-araldite resin (Electron Microscopy Sciences). Briefly, the samples were embedded in a 1:1 ratio of propylene oxide to Epon Araldite for 2 hours, followed by embedding in 100% Epon Araldite for 3 hours, and then transferring each sample to embedding molds with fresh 100% Epon Araldite and cured in a 60° C. oven overnight. 60-90 nm gold- and silver-colored sections were stained for 5 minutes with urinyl acetate saturated in 50% ethanol, followed by staining for 20 minutes in lead citrate according to the methods of Venable and Coggesmall (1965). The stained sections from each of the samples were then imaged with a ZEISS electron microscope for observation of cell, collagen, and ECM morphology. The average collagen fibril diameter and density were calculated from the average measured diameters and number of collagen fibrils per square micrometer from 5 randomly chosen fields taken at high magnification (57,000× or 88,000×). The collagen diameters were measured at the thinnest point of cross-sectioned collagen fibrils with a 5× magnified ruler. If a randomly chosen field fell on a grid, then another field continued to be randomly chosen until it fell solely on the sample.

H. Statistics

Error bars indicate one standard deviation in all figures. Statistical differences between groups were determined using ANOVA with Tukey HSD post hoc analysis (SPSS, Inc., Chicago, Ill.). Differences were considered significant with $p<0.05$. Linear regression was performed and the $R^2$-values were obtained for determining the degree of association between the independent and dependent variables (SPSS, Inc.).

Results and Discussion

Experiments were designed and carried out to determine whether the extracellular matrix (ECM) produced and assembled solely by hyperconfluent cells is mechanically superior to ECM generated by allowing cells to compact and remodel gels cast from purified solutions of collagen or fibrin. To reduce experimental variability, all groups were grown in parallel with two million human foreskin fibroblasts from the same batch, fed with the same standard serum-supplemented media at the same time, and grown for 3-weeks next to each other on the same 6-well plates. The collagen gels (CGs) and fibrin gels (FGs) started out at a thickness of 2.2 mm and contracted to a thickness 83±5 µm and 218±5 µm, respectively. The cell-derived matrices (CDMs), on the other hand, started out at slightly more than a single cell layer thick and grew to 125±6 µm, with the synthesized ECM organizing into several alternating layers that were at approximate right-angles to each other, resembling native soft connective tissue (FIG. 17). After 3 weeks in culture, the CDMs were considerably stronger than the CGs and significantly stronger than the FGs (see Table 1).

Other measurements of CDM thickness was determined using digital image analysis, as indicated in FIG. 15. FIGS. 15A-E show Hematoxylin and Eosin (H&E) stained sections of fibroblast-populated collagen gel (CG), fibrin gel (FG), and three cell-derived matrices (CDM, *CDM, and **CDM), respectively. All samples were grown for 3 weeks starting with the same initial number of fibroblasts. Fibroblasts were embedded in 1 mg/ml of collagen in the collagen gel, and in 1 mg/ml fibrin in the fibrin gel. The collagen and fibrin gels started at 1 mm thickness and contracted to 84 µm thick and 230 µm thick, respectively, over the first few days. The cell-derived matrices started at 2-3 cell layers thick and grew to 110 µm (CDM), 465 µm (*CDM), and 240 µm (**CDM) and in thickness, respectively, over the 3-week culture period. The CDMs were at least 5 times stronger (120 N/m for LTM versus 25 N/m for CG and FG) than the collagen and fibrin matrices (see FIG. 16B) and contained numerous extracellular matrix proteins in amounts, ratios and arrangement that resembled young, native, blastema-like tissue. All micrographs were taken at 200× magnification. The thickness was measured by digital image analysis. Scale bars=100 µm. The values for the CGs and FGs are in line with results obtained by other researchers and indicate that cell-produced ECM (i.e. CDM) can be made stronger than reconstituted ECM within a relatively short period of time.

Figure 16A:
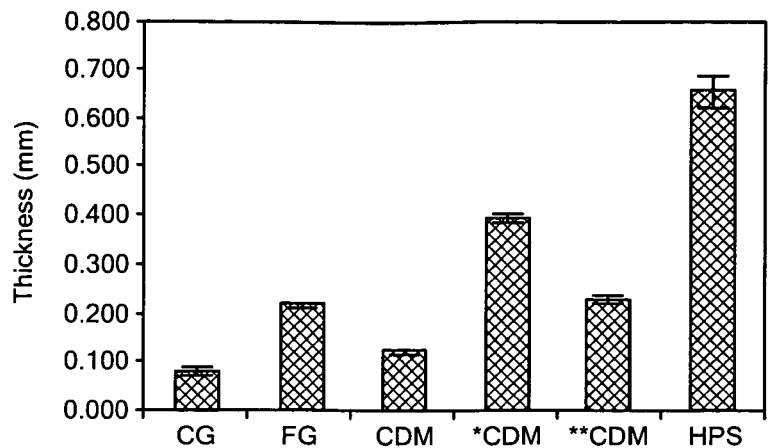
FIG. 16A is a graphical representation of the results in Table 1 showing the thickness (µm) of the fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).

An embodiment of the presently defined invention also provides a relatively simple chemically-defined medium for promoting high ECM synthesis by multilayered fibroblasts. Embodiments of the resulting minimal serum-free medium are similar to a serum-supplemented medium, except that in place of supplementation with serum, the chemically-defined medium is supplemented with basic fibroblast growth factor (bFGF), epidermal growth factor (EGF), dexamethasone and L-3,3′,5-triiodothyronine, and a few other components that were determined to be necessary for cell growth that are present in serum (insulin, selenious acid, and a lipid precursor). The presence of these few components instead of serum resulted in a doubling (**CDMs: growth factors added into the stock medium at the start of the 3-week culture period) or tripling (*CDMs: growth factors added fresh at each feeding) in thickness (see Table 1, and FIG. 16A), and a 40% (*CDM) or 210% (**CDM) increase in the ultimate tensile strength (UTS) (Table 1, and FIG. 16F) over standard serum-supplemented samples (CDM). The matrix produced using either version of the chemically-defined medium also resulted in a doubling of the failure strain (Table 1 and FIG. 16J), a quadrupling of the proliferation rate (Table 1 and FIG. 16I), and a quintupling of the fraction of non-acid and pepsin extractable collagen (Table 1 and FIG. 16K)—a parameter that is highly correlated (adjusted $R^2$=0.977) with the strength of the sample matrices. Interestingly, when collagen gels were fed with the chemically-defined medium (*CG), the contractile forces within the collagen gels became so great that they detached from the wells and contracted into themselves within 24 h of feeding them with the chemically-defined medium. This excessive contraction prevented a comparison of the effects of the chemically-defined medium and the serum-supplemented medium on the development of gels and is the subject of further studies.

In addition, the structural characteristics and biochemical composition between the five types of matrix were compared, as well as with native penile skin, to determine how these differences correlated with their biomechanical properties. These studies were done to provide further insight into the mechanisms of cell-mediated strengthening of ECM. Human penile skin was to compare native soft connective tissue to the 5 different living tissue equivalents (LTEs) produced in this study, even though it is several-fold weaker than normal skin, since the fibroblasts used in making the LTEs were derived from neonatal human foreskin.

Although it is known that fibroblasts entrapped in purified collagen synthesize far less ECM proteins than in monolayer cultures, while fibroblasts entrapped in purified fibrin retain their ability to produce ECM protein, our data also surprisingly demonstrate that fibroblasts in self-produced collagen-rich matrices produce an even greater amount of ECM proteins such as collagen than in purified fibrin gels. Moreover, although the cell-derived matrices synthesized a similar amount of collagen as that of the collagen gels, the CDM-synthesized collagen did not appear to result in any inhibition of ECM synthesis in the cell-derived matrices. Specifically, the total protein synthesized by the cells in the cell-derived matrices was significantly more than the net increase in total protein in the collagen gels and fibrin gels (see Table 1 and FIG. 16E).

These values are higher but in line with the results obtained by other researchers for gels and cell-produced matrices (Grinnell et al., 1989; Huang et al., 1993; Clark et al., 1997; Neidert et al., 2002). These differences could be due to the much greater cell density of our cultures that might have signaled the fibroblasts to synthesize more ECM as in the CDM cultures. These differences might also be due to the use of porous inserts that provided a shorter diffusion distance for nutrients for cells on the basal side of the samples (the use of porous inserts resulted in a more than 50% increase in thickness (but no effect on UTS) over samples grown on regular 6-well plates (data not shown)), or the 80% greater concentration of L-ascorbate, in the more stable form of L-ascorbic acid phosphate magnesium salt n-hydrate (1 week stability versus 24 h stability for L-ascorbate).

Figure 16B:
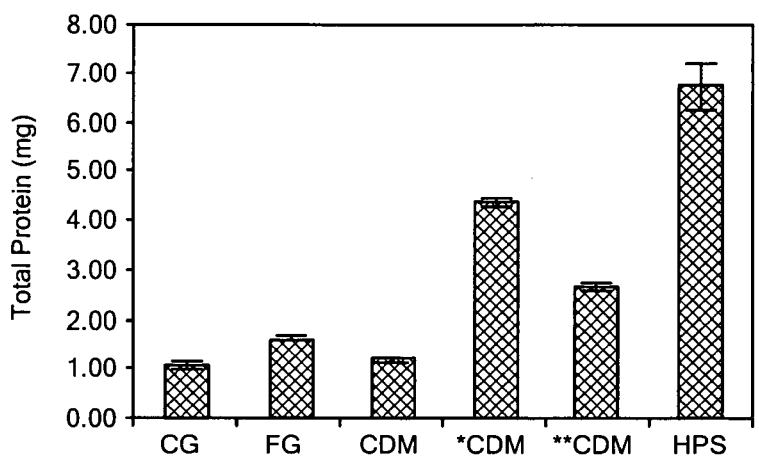
FIG. 16B is a graphical representation showing the tensile strength (N/m) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16C:
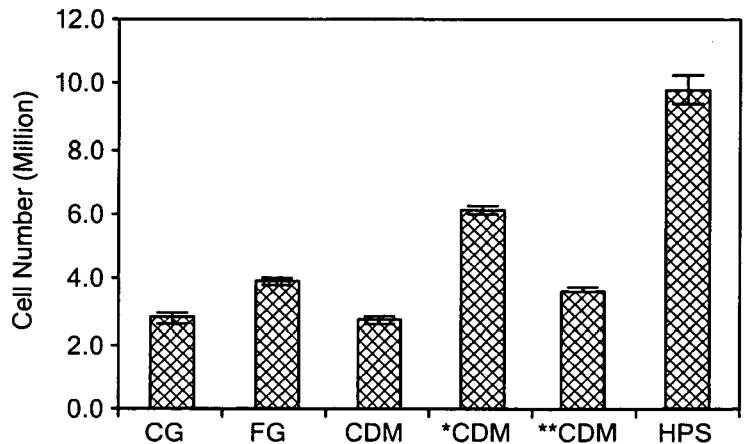
FIG. 16C is a graphical representation of the results in Table 1 showing the total collagen (mg) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16D:
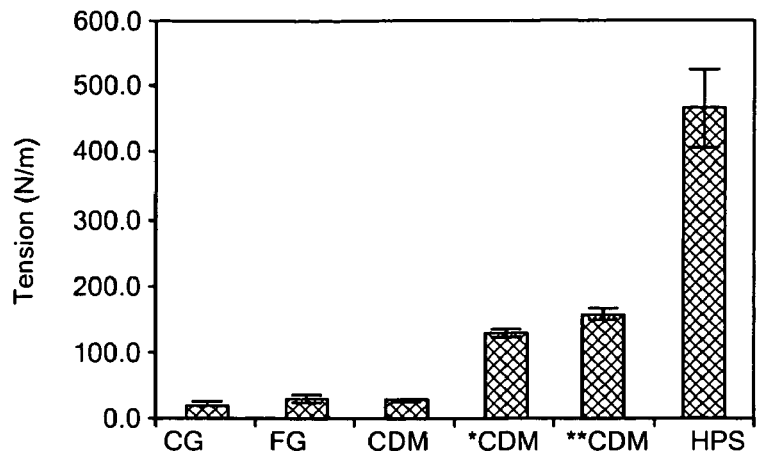
FIG. 16D is a graphical representation of the results in Table 1 showing the total proteoglycans and glycosaminoglycans (µg) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16E:
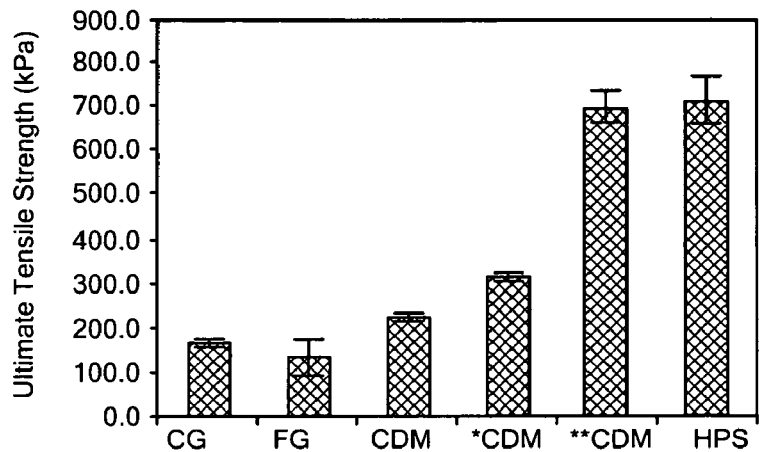
FIG. 16E is a graphical representation of the results in Table 1 showing the total protein (mg) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16F:
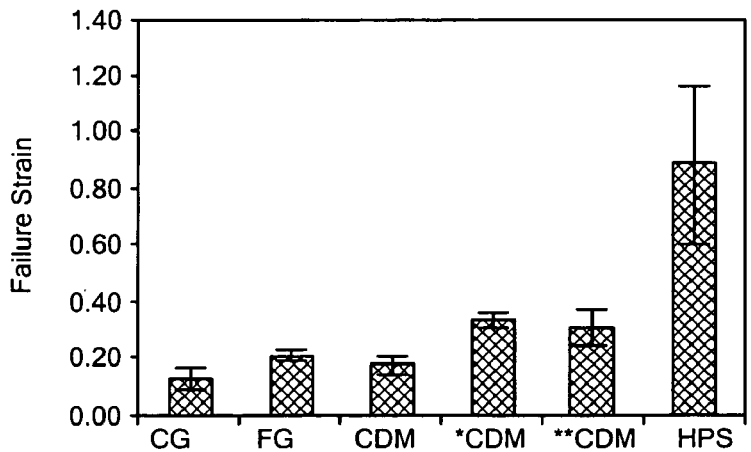
FIG. 16F is a graphical representation of the results in Table 1 showing the ultimate tensile strength (kPa) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16G:
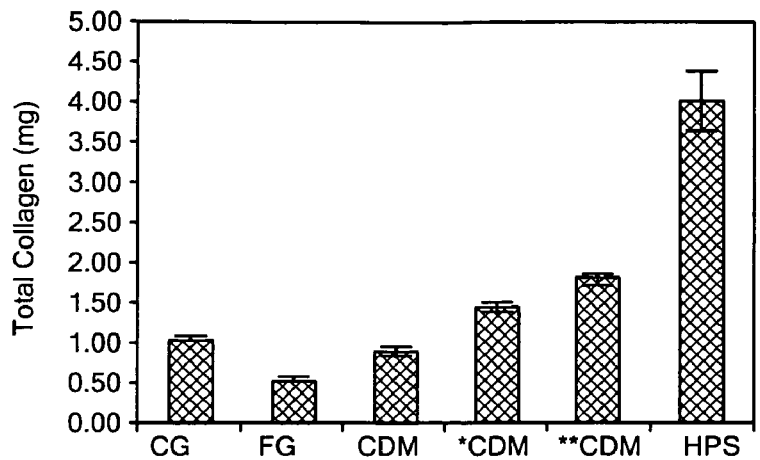
FIG. 16G is a graphical representation showing the % collagen of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16H:
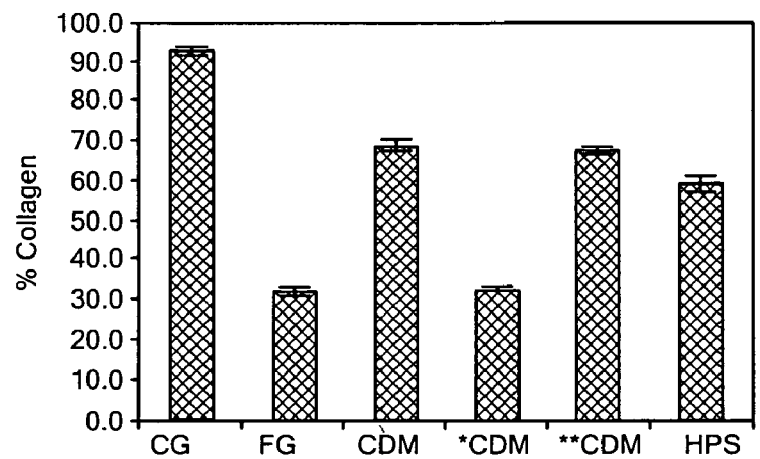
FIG. 16H is a graphical representation showing the % proteoglycans and glycosaminoglycans of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16I:
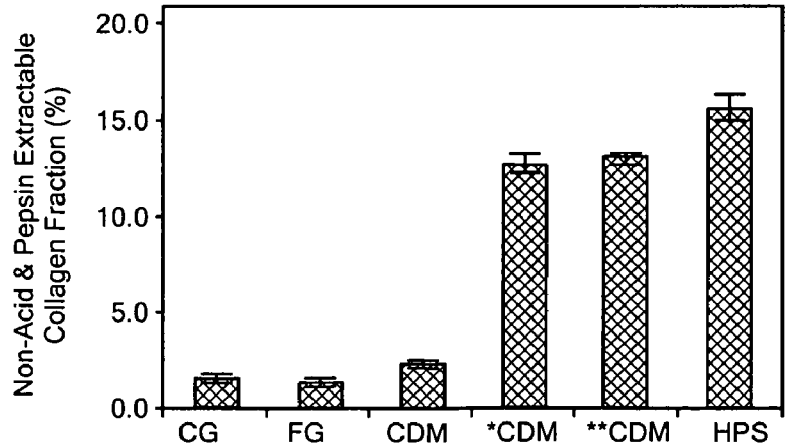
FIG. 16I is a graphical representation of the results in Table 1 showing the cell number (millions) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16J:
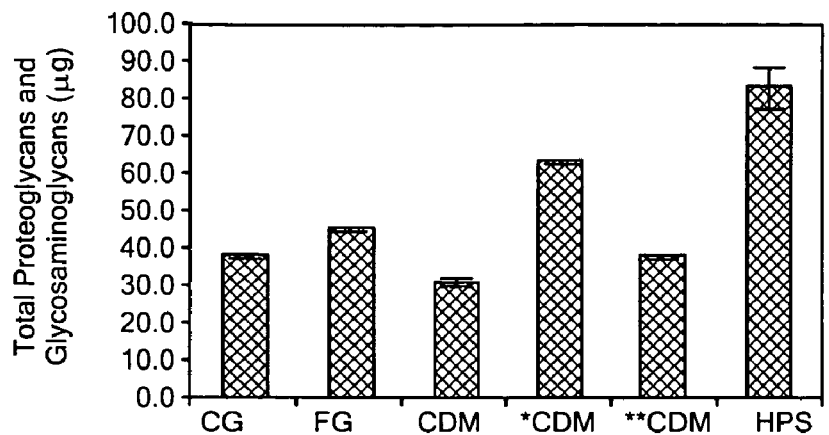
FIG. 16J is a graphical representation of the results in Table 1 showing the failure strain of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 16K:
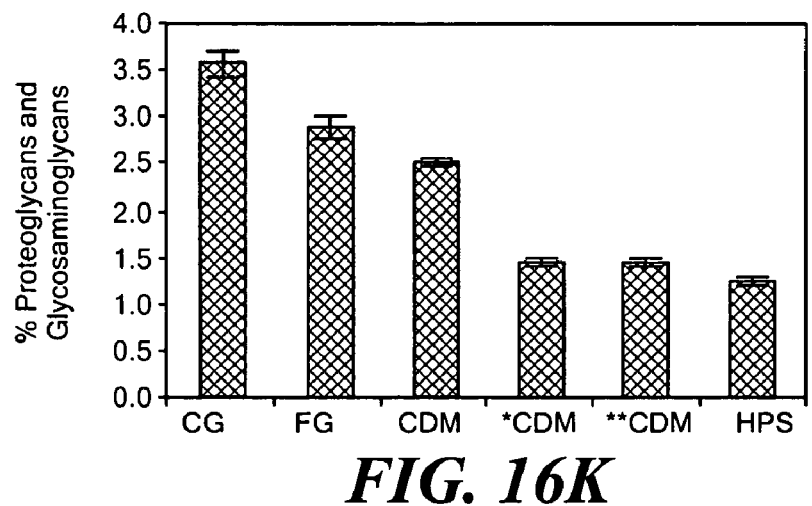
FIG. 16K is a graphical representation of the results in Table 1 showing the non-acid and pepsin extractable collagen fraction (%) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).

The cell-derived matrices also had a significantly greater fraction of non-acid and pepsin extractable collagen (insoluble collagen fraction) than the collagen and fibrin gels (see Table 1 and FIG. 16K). The non-acid and pepsin extractable collagen fraction was the amount of collagen that was not solubilized by repeated 0.5 M acetic acid and pepsin (1 mg/ml) extraction steps over a 3-day period. The non-acid and pepsin extractable collagen density provides a measure of very stable collagen in the tissues that is highly cross-linked or bundled to resist extraction. The UTS/Collagen Density, a metric that is independent of the thickness of the samples and represents the strength of the constructs normalized per unit of collagen, was likewise significantly greater for the cell-derived matrices than the collagen gels (Table 1 and FIG. 16L). The high value of UTS/Collagen Density for the fibrin gels (25.9±2.4 kPa/mg/cm$^3$—see Table 1) might be due to ECM proteins other than collagen, such as fibrin, in the gel. However, others have found that the UTS of fibrin gels are correlated to the total collagen amount in the constructs ($R^2$=0.77 at day 21), and our study found that the UTS correlated to the collagen density ($R^2$=0.73 at day 21) not just in fibrin gels but also in collagen gels and cell-derived matrices. Our results indicate that UTS of the CDMs of the presently claimed invention correlate even more closely to the non-acid and pepsin extractable collagen density ($R^2=0.993$) than to collagen density. Thus, the strength of living tissue equivalents as described here, as well as native soft connective tissue, is not just correlated with collagen density, but more specifically to a very stable form of collagen represented by the non-acid and pepsin extractable collagen density.

The strength of soft connective tissues, as well as living tissue equivalents such as fibroblast-populated collagen gels, is generally attributed to the collagen density and average collagen fibril diameter. As summarized in Table 1, observation by transmission electron microscopy (tEM) revealed that the diameter of the collagen fibrils in the CDMs, *CDMS, collagen gels and fibrin gels were 46±5 nm, 48±5 nm, 52±10 nm and 47±5 nm, respectively, while the collagen density was significantly greater for the CDMs (79±2 fibrils/$\mu m^2$), *CDMs (80±2 fibrils/$\mu m^2$) and collagen gels (81±4 fibrils/$\mu m^2$) than for the fibrin gels (28±4 fibrils/$\mu m^2$, p<0.01). These diameters fall within the range of collagen fibril diameters (40-100 nm) found in native soft connective tissue.

In the present case, although most of the collagen in the collagen gel consisted of large, approximately 56 nm diameter fibrils, there was a small presence of approximately 46 nm diameter fibrils; presumably newly synthesized collagen (see FIG. 17), indicating that some of the original collagen in the gel had been degraded since the total amount of collagen in the collagen gels remained unchanged over the 3-week period. And although the collagen gels disclosed herein had by far the greatest collagen density and the largest collagen fibril diameters, they were significantly weaker than the cell-derived matrices grown under identical conditions. As can be seen in FIGS. 17A-17D, distribution of collagen fibrils. CDMs, collagen gels, and *CDMs had a more than 2.5 times greater density of collagen fibrils at around 80 fibrils/$\mu m^2$ than fibrin gels at 28 fibrils/$\mu m^2$. Collagen fibrils are shown by arrows, and all micrographs were taken at 12,000× with the scale bar=1 $\mu m$. The collagen fibrils of the cell-derived matrices (FIGS. 17C and D) appeared more parallel and to consist of more parallel alternating layers than any of the other groups (see upper portion of CDM where the micrograph consists of cross-sections of thousands of parallel collagen fibrils). The collagen fibrils of the collagen gels (FIG. 17A) appeared somewhat parallel but consisted of only a few alternating layers, while the collagen fibrils of the fibrin gels (FIG. 17B) appeared only parallel in small regions of the ECM.

Without being limited to theory, this discrepancy could be due to a greater presence of intra-molecular covalent cross-links between the collagen fibrils or more extensive bundling of the collagen fibrils into fibers in the cell-derived matrices than in the collagen gels and fibrin gels. The non-acid and pepsin extractable collagen fraction was closely correlated to the UTS/Collagen Density values for all these groups ($R^2=0.93$), except for the fibrin gels ($R^2=0.11$). The *CDMs and **CDMs, which had a several-fold greater fraction of non-acid and pepsin extractable collagen than any of the other samples, also had a higher thermal and enzymatic stability than any of the other samples (data not shown). The very stable collagen represented by the non-acid and pepsin extractable collagen fraction appears to consist of highly cross-linked or bundled collagen that resists extraction and gives rise to a more resistant structure that leads to strengthening of the matrix.

Figure 16L:
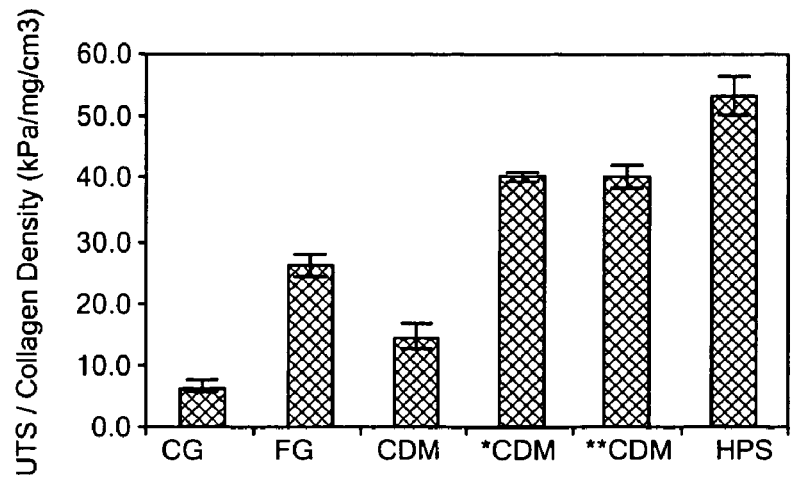
FIG. 16L is a graphical representation of the results in Table 1 showing the UTS/collagen density (kPa/mg/cm$^3$) of fibroblast-populated collagen gel (CG) and fibrin gel (FG), and cell-derived matrix (CDM) fed with serum-supplemented medium; and cell-derived matrices (*CDM and **CDM) fed with Matrix Media, compared to human penile skin (HPS).
Figure 17A:
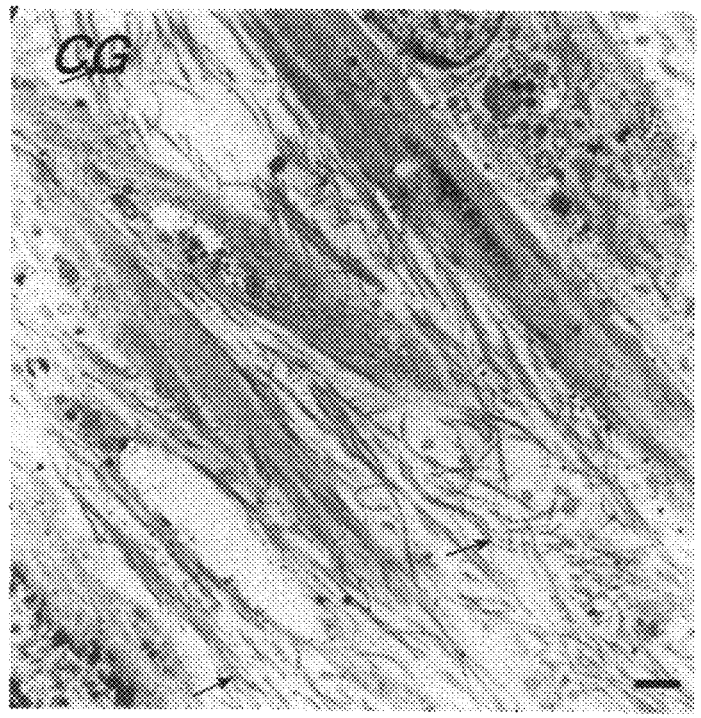
FIG. 17A shows a TEM 12,000×; scale bar=1 µm) of the distribution of collagen fibrils (arrows) in the collagen gel (CG), wherein most (from the collagen gel) are about 56±5 nm in diameter with a small number (presumably secreted by fibroblasts I the gel) about 46±5 nm in diameter. The collagen density was 81±4 fibrils/µm$^2$.
Figure 17B:
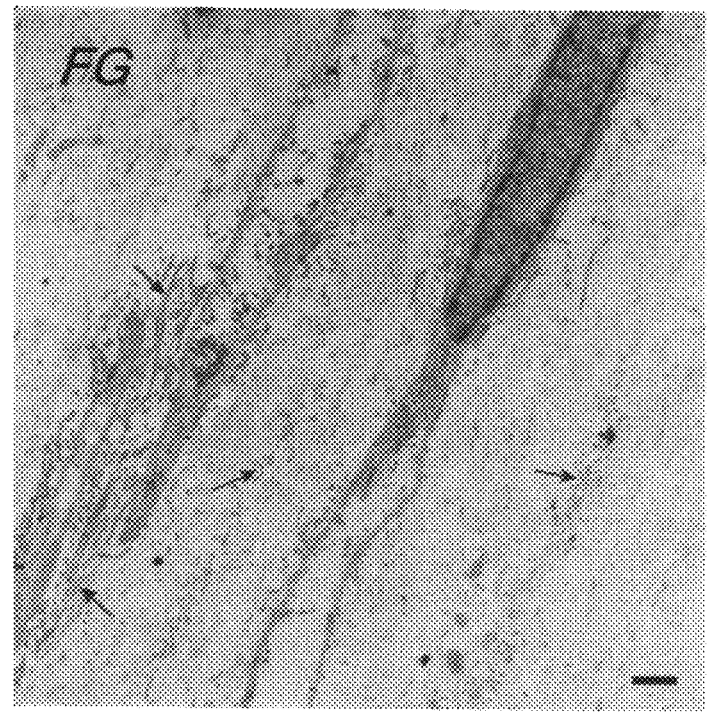
FIG. 17B shows a TEM 12,000×; scale bar=1 µm) of the distribution of collagen fibrils (arrows) in the fibrin gel (FG) wherein the collagen fibrils have a diameter of about 48±5 nm in diameter. The collagen density was 28±4 fibrils/µm$^2$, ($p<0.01$).
Figure 17C:
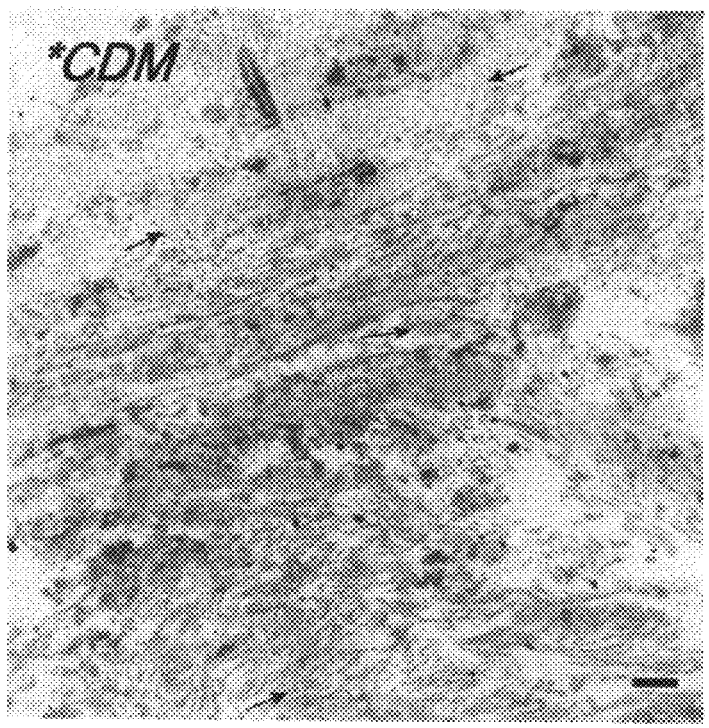
FIG. 17C shows a TEM (12,000×; scale bar=1 µm) of the distribution of collagen fibrils (arrows) in the cell-derived matrix (CDM) wherein the collagen fibrils have a diameter of about 52±10 nm in diameter. The collagen density was 79±2 fibrils/µm$^2$.
Figure 17D:
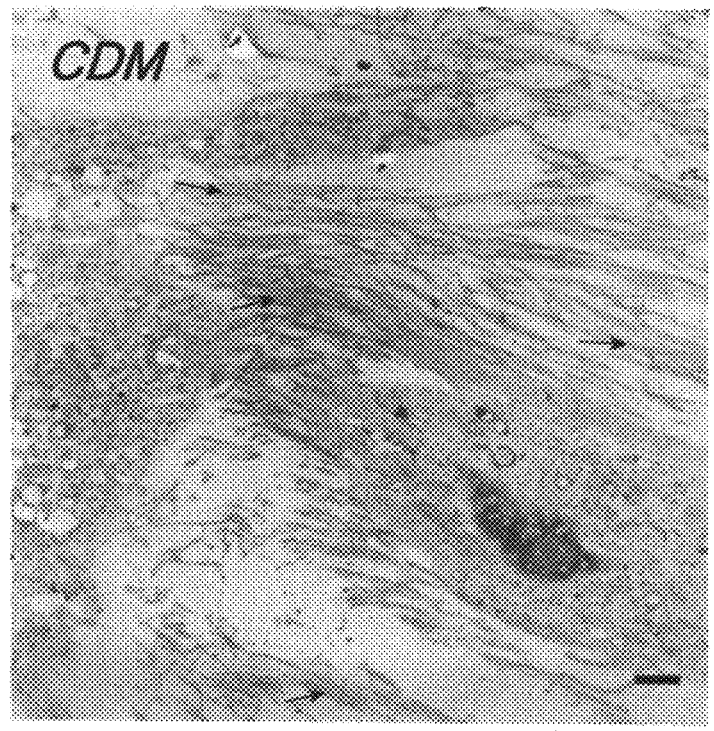
FIG. 17D shows a TEM (12,000×; scale bar=1 µm) of the distribution of collagen fibrils (arrows) in the cell-derived matrix (*CDM) fed with Matrix Media wherein the collagen fibrils have a diameter of about 47±5 nm in diameter. The collagen density was 80±2 fibrils/µm$^2$.

Looking at FIG. 16, a graphical depiction of the data in Table 1, it can be seen in FIGS. 16B and 16F that all types of cell-derived matrices were stronger than collagen gels (CG) and fibrin gels (FG). *CDMs and **CDMs were significantly thicker (FIG. 16A) and contained far more total protein (FIG. 16E) than their serum-supplemented companions (CDMs, collagen gels and fibrin gels), but had only half the percentage of proteoglycans and glycosaminoglycans (FIGS. 16D and 16H). *CDMs and **CDMs also contained a significantly higher fraction of non-acid and pepsin extractable collagen (FIG. 16K), and were stronger per microgram of collagen (UTS/Collagen Density) than collagen gels or fibrin gels (FIG. 16L). CDMs were more than twice as strong as collagen gels per microgram of collagen, indicating the possibility that the collagen in the CDMs was more organized for strength than in collagen gels. In addition to collagen, a substantial proportion of the strength of *CDMs and fibrin gels was also due to other ECM proteins. *CDMs and CDMs were significantly more extensible than CDMs, collagen gels and fibrin gels. Human penile skin (HPS) most closely resembled CDM mechanically, and *CDM and **CDM biochemically.

The lowered growth factor concentration over time that occurs naturally in vivo during the wound healing response, where the high concentration of growth factors in a fresh clot decreases over time as it is invaded and reconstructed by fibroblasts, was approximated by adding the growth factors (EGF and bFGF) directly into the feeding media at the start of the 3-week culture period and taking advantage of the natural loss of growth factor activity in media over time. This one-time addition of growth factors at the start of the 3-week period (**CDM) resulted in a matrix with about ½ the thickness of parallel samples (*CDM) for which the growth factors were added fresh at every feeding (see Table 1 and FIG. 16A). The thickness was highly correlated with total protein content ($R_{adj}^2=0.9$), which in turn correlated with total cell number ($R_{adj}^2=0.874$. Interestingly, the **CDMs had significantly more total collagen than *CDMS, although the *CDMs had almost twice as much total protein as the CDMs (Table 1 and FIG. 16C). Since collagen is the major extracellular matrix protein providing strength, the CDMs, with a more than two-fold greater fraction of collagen than the *CDMS, were also almost twice as strong as the *CDMs (Table 1 and FIG. 16F).

Cell-derived matrices grown for longer periods (up to 6 weeks) further continued to increase in thickness and strength (data not shown). It is possible that the **CDMs developed mostly in thickness for the first part of the growth period followed by development in strength for the remainder of the growth period, since adding lower concentrations of fresh growth factors at every feeding instead resulted in matrices that were significantly stronger than the *CDMs but significantly thinner than the **CDMs (data not shown). This effect appears to be due to the fact that EGF stimulates the synthesis of non-collagenous proteins but inhibits the transcription of type 1 collagen genes, while high bFGF concentrations favor increased cell proliferation over enhancing the synthesis and strengthening of the ECM. Thus a decrease in total growth factor activity over time results in less synthesis of non-collagenous proteins, but an increase in the strength of the synthesized ECM by the resulting increase in collagen synthesis. Many growth factors, including bFGF, can also accumulate and retain their activity for relatively long periods of time within ECM. Thus some of the added growth factors might have accumulated in the ECM during the first part of the culture period and then used up continuously as the matrix developed. The failure strains for the *CDMs and **CDMs were also significantly greater than for their serum-supplemented counterparts (Table 1 and FIG. 16J), closer mimicking native soft connective tissue.

These results demonstrate that living tissue equivalents are stronger and thicker when they are cell-produced—in other words, when the cells are allowed to grow and develop their own mechanical environment rather than being supplied with a scaffold, such as gels or other biopolymer materials. This strength appears to be due to a greater fraction of very stable collagen and the significantly greater synthetic rate of fibroblasts in ALSs/LTMs than in gels. The LTMs and their cell-derived matrix component (*CDM and **CDM) produced and described herein have potential for use as soft connective tissue substitutes since they are produced solely from cells fed with a chemically-defined medium that does not contain animal components. The rapid growth and lack of expensive serum makes the development of LTMs as soft connective tissue substitutes commercially more viable, and opens the door to mainstream acceptance and appeal.

Due to the relative simplicity of the chemically-defined medium, these cell-produced living tissue equivalents may also serve as in vitro biological models for the effects of nutritional components and pharmaceutical products on the growth and development of soft connective tissue, for examining the numerous in vivo conditions and processes such as wound healing and connective tissue formation, and for investigating the development and interaction of different cells and tissues in a soft connective tissue environment that is developed solely from cells in vitro. The higher thermal and enzymatic stability and mechanical integrity of cell-derived matrices over both collagen and fibrin gels may also allow them to retain their structural integrity longer in in vivo conditions. The ability to grow LTMs thick and strong in a relatively short period of time in chemically-defined conditions provides a commercially viable option for wound repair and tissue regeneration as an attractive alternative to the use of fibrin gels, collagen gels and even native tissues.

i) incubating the fibroblast cells at a concentration of at least about 200,000 cells/cm$^2$ in defined chemical media containing components that promote proliferation and extracellular matrix synthesis of said fibroblast cells; and ii) isolating the construct from the media, wherein the cells are incubated for a period of time in the media that is sufficient to produce a construct having a thickness and porosity that enables cellular migration of additional cells throughout the construct wherein the construct has a failure strain of at least about 0.2.

2. The construct of claim 1, wherein the fibroblast cells are seeded at a concentration of at least about 200,000 cells/cm$^2$.

3. The construct of claim 1, wherein the defined chemical media is serum-free media comprising base media, basic fibroblast growth factor, epidermal growth factor, dexamethasone, L-3,3',5-triiodothyronine, insulin, selenious acid, and a lipid precursor.

4. The construct of claim 1, wherein said construct has a tensile strength of at least 200 kilopascals within three weeks of growth.

5. The construct of claim 3, wherein the base media is selected from the group consisting of Dulbecco's Modification of Eagle's Medium (DMEM); Ham's F-12 (F12); Ham's F-10 (F10); Iscove's Modification of DMEM (IDMEM); MEDIUM 199; Alpha MEM; Basal Medium Eagle with Earle's BSS; DMEM:F1.2 1:1 with L-Glutamine; Glasgow's MEM with L-glutamine (GMEM); IMDM with HEPES, with or without L-Glutamine; L-15, without L-Glutamine; McCoy's 5A Modified Medium; Medium 199; MEM Eagle; MEM Eagle-Earle's BSS, with or without L-Glutamine;

TABLE 1

Results from mechanical and biochemical analysis of human penile skin and cell-derived matrices (CDMs, *CDMs, **CDMs), fibroblast-populated collagen gels and fibrin gels containing human foreskin fibroblasts. Numbers indicate mean +/− SD. Numbers in parentheses indicate approximate initial amount. Collagen fibril diameters and densities were measured in proximity to cell surfaces.

| Measure | Collagen gel | Fibrin gel | CDM | *CDM | **CDM | Penile Skin |
|---|---|---|---|---|---|---|
| Ultimate Tensile Strength (kPa) | 168.5 ± 43.1 | 133.2 ± 10.6 | 223.2 ± 9 | 314.5 ± 7.2 | 697.1 ± 36.1 | 713.0 ± 55.2 |
| Thickness (μm) | 83 ± 5 (2,220 μm) | 218 ± 5 (2,220 μm) | 125 ± 6 (~30 μm) | 395 ± 6 (~30 μm) | 225 ± 7 (~30 μm) | 651 ± 30 |
| Failure Strain | 0.13 ± 0.02 | 0.21 ± 0.03 | 0.18 ± 0.03 | 0.33 ± 0.03 | 0.31 ± 0.06 | 0.88 ± 0.28 |
| Total Protein (mg) | 1.08 ± 0.03 (1.0 mg) | 1.58 ± 0.04 (1.0 mg) | 1.25 ± 0.06 | 4.40 ± 0.08 | 2.65 ± 0.07 | 6.74 ± 0.44 |
| Total Collagen (mg) | 0.99 ± 0.02 (1.0 mg) | 0.51 ± 0.03 | 0.85 ± 0.03 | 1.40 ± 0.04 | 1.78 ± 0.06 | 3.98 ± 0.37 |
| Non-Acid and Pepsin Extractable Collagen Fraction (%) | 1.5 ± 0.1 | 1.3 ± 0.1 | 2.3 ± 0.2 | 12.8 ± 0.5 | 13.1 ± 0.3 | 15.7 ± 0.7 |
| Collagen Density (mg/cm$^3$) | 26.5 ± 1.5 | 5.2 ± 0.2 | 15.1 ± 0.9 | 7.8 ± 0.2 | 17.4 ± 0.1 | 13.5 ± 0.7 |
| UTS/Collagen Density (kPa/mg/cm$^3$) | 6.4 ± 1.9 | 25.9 ± 2.4 | 14.5 ± 1.1 | 40.3 ± 0.4 | 40.0 ± 1.9 | 52.9 ± 3.1 |
| Collagen Fibril Diameter (nm) | 52 ± 10 | 47 ± 5 | 46 ± 5 | 48 ± 5 | — | — |
| Collagen Fibril Density (fibrils/μm$^2$) | 81 ± 4 | 28 ± 4 | 79 ± 2 | 80 ± 2 | — | — |
| Total Proteoglycans & Glycosaminoglycans (μg) | 38.4 ± 0.7 | 45.4 ± 0.9 | 31.3 ± 0.5 | 64.3 ± 0.6 | 38.4 ± 0.4 | 83.0 ± 5.7 |
| Wet Weight/Dry Weight | 16.4 ± 0.6 | 20.1 ± 0.4 | 13.0 ± 0.5 | 19.5 ± 0.2 | 20.3 ± 0.6 | 21.7 ± 0.4 |
| Cell Number (million) | 2.8 ± 0.1 (2.0 million) | 4.0 ± 0.1 (2.0 million) | 2.8 ± 0.1 (2.0 million) | 6.1 ± 0.1 (2.0 million) | 3.6 ± 0.1 (2.0 million) | 9.8 ± 0.4 |

What is claimed:

1. A three-dimensional cell-produced scaffold construct comprising extracellular matrix synthesized in vitro by fibroblast cells, wherein said construct is produced by a process comprising:

MEM Eagle-Flanks BSS; NCTC-109; Richter's CM Medium; RPMI 1640 with HEPES; RPMI 1640 and a combination thereof.

6. The construct of claim 5, wherein the serum-free defined chemical media further comprises additional components selected from the group consisting of platelet derived growth factor (PDGF), L-cysteine, Trolox and combinations thereof.

7. The construct of claim 3, wherein the serum-free defined chemical media comprises:
   (i) L-ascorbic acid phosphate magnesium salt n-hydrate in a concentration range of from 0.1 mM to 3 mM;
   (ii) epidermal growth factor in a concentration range of from 0.002 nM to 2 nM;
   (iii) basic fibroblast growth factor in a concentration range of from 0.03 nM to over 3 nM;
   (iv) insulin in a concentration range of from 10 µM to 1000 µM;
   (v) L-3,3',5-triiodothyronine in a concentration range of from 0.1 nM to 10 nM;
   (vi) ethanolamine in a concentration range of from 1 µM to 10,000 µM;
   (vii) selenious acid in a concentration range of from 10 mM to 1000 mM;
   (viii) Glutamax in a concentration range of from 0 mM to 10 mM; and
   (ix) dexamethasone in a concentration range of from 1 nM to 1000 nM.

8. The construct of claim 3, wherein the serum-free defined chemical media comprises a 3:1 ratio of DMEM (high glucose (4.5 g/L); with L-glutamine and sodium pyruvate) and Ham's F12 medium supplemented with the following components:
   (i) $4.2 \times 10^{-10}$ M epidermal growth factor;
   (ii) $2.8 \times 10^{-10}$ M basic fibroblast growth factor
   (iii) $8.6 \times 10^{-5}$ M insulin
   (iv) $1.0 \times 10^{-7}$ M dexamethasone
   (v) $3.2 \times 10^{-4}$ M L-ascorbic acid phosphate magnesium salt n-hydrate
   (vi) $2 \times 10^{-10}$ L-3,3',5-triiodothyronine
   (vii) $10^{-4}$ M ethanolamine
   (viii) $3.9 \times 10^{-8}$ M selenious acid
   (ix) $4 \times 10^{-3}$ M Glutamax
   (x) $3.3 \times 10^{-6}$ M glutathione (reduced); and
   (xi) 1% penicillin/streptomycin/amphotericin B.

9. The construct of claim 8, wherein the serum-free defined chemical media further comprises an additional component selected from the group consisting of platelet derived growth factor in a concentration of from 0.1 ng/ml to 10 ng/ml; L-cysteine in a concentration range of from 0.1 mM to 1 mM, and combinations thereof.

10. The construct of claim 1, wherein the fibroblast cells are seeded at a density of between 200,000 to 1,000,000 cells/cm².

11. The construct of claim 3, wherein the medium is replaced every 2-3 days.

12. The construct of claim 1, wherein the construct has a growth rate in the media such that it is capable of achieving a thickness of greater than 100 µm within three weeks of growth.

13. A three-dimensional cell-produced scaffold construct comprising fibroblast cells and extracellular matrix synthesized in vitro by said fibroblast cells, wherein said construct has a thickness and porosity that enables cellular migration throughout the construct, wherein the construct has a growth rate in the media such that it is capable of achieving a thickness of greater than 100 µm within three weeks of growth, wherein the construct is made by a process comprising:
   i) incubating the fibroblast cells at a concentration of at least about 200,000 cells/cm² in defined chemical media containing components that promote proliferation and extracellular matrix synthesis of said fibroblast cells; and
   ii) isolating the construct from the media.

14. A three-dimensional cell-produced scaffold construct comprising extracellular matrix synthesized in vitro by fibroblast cells, wherein said construct is produced by a process comprising:
   i) incubating the fibroblast cells at a concentration of at least about 200,000 cells/cm² in defined chemical media containing components that promote proliferation and extracellular matrix synthesis of said fibroblast cells; and
   ii) isolating the construct from the media,
wherein the construct has a porosity such that it is capable of achieving a thickness of greater than 200 µm.

15. The construct of claim 13, wherein the fibroblast cells are seeded at a concentration of at least 200,000 cells/cm² in serum-free defined chemical media.

16. The construct of claim 15, wherein the serum-free defined chemical media comprises base media, basic fibroblast growth factor, epidermal growth factor, dexamethasone, L-3,3',5-triiodothyronine, insulin, selenious acid, and a lipid precursor.

17. The construct of claim 16, wherein the base media is selected from the group consisting of Dulbecco's Modification of Eagle's Medium (DMEM); Ham's F-12 (F12); Ham's F-10 (F10); Iscove's Modification of DMEM (IDMEM); MEDIUM 199; Alpha MEM; Basal Medium Eagle with Earle's BSS; DMEM:F12 1:1 with L-Glutamine; Glasgow's MEM with L-glutamine (GMEM); IMDM with HEPES, with or without L-Glutamine; L-15, without L-Glutamine; McCoy's 5A Modified Medium; Medium 199; MEM Eagle; MEM Eagle-Earle's BSS, with or without L-Glutamine; MEM Eagle-Hanks BSS; NCTC-109; Richter's CM Medium; RPMI 1640 with HEPES; RPMI 1640 and a combination thereof.

18. The construct of claim 17, wherein the serum-free defined chemical media further comprises additional components selected from the group consisting of platelet derived growth factor (PDGF), L-cysteine, Trolox and combinations thereof.

19. The construct of claim 15, wherein the serum-free defined chemical media comprises:
   (i) L-ascorbic acid phosphate magnesium salt n-hydrate in a concentration range of from 0.1 mM to 3 mM;
   (ii) epidermal growth factor in a concentration range of from 0.002 nM to 2 nM;
   (iii) basic fibroblast growth factor in a concentration range of from 0.03 nM to over 3 nM;
   (iv) insulin in a concentration range of from 10 µM to 1000 µM;
   (v) L-3,3',5-triiodothyronine in a concentration range of from 0.1 nM to 10 nM;
   (vi) ethanolamine in a concentration range of from 1 µM to 10,000 µM;
   (vii) selenious acid in a concentration range of from 10 nM to 1000 nM;
   (viii) Glutamax in a concentration range of from 0 mM to 10 mM; and
   (ix) dexamethasone in a concentration range of from 1 nM to 1000 nM.

20. The construct of claim 15, wherein the serum-free defined chemical media comprises a 3:1 ratio of DMEM (high glucose (4.5 g/L); with L-glutamine and sodium pyruvate) and Ham's F12 medium supplemented with the following components:
   (i) $4.2 \times 10^{-10}$ M epidermal growth factor;
   (ii) $2.8 \times 10^{-10}$ M basic fibroblast growth factor
   (iii) $8.6 \times 10^{-5}$ M insulin (iv) $1.0 \times 10^{-7}$ M dexamethasone
(v) $3.2 \times 10^{-4}$ M L-ascorbic acid phosphate magnesium salt n-hydrate
(vi) $2 \times 10^{-10}$ M L-3,3',5-triiodothyronine
(vii) $10^{-4}$ M ethanolamine
(viii) $3.9 \times 10^{-8}$ M selenious acid
(ix) $4 \times 10^{-3}$ M Glutamax
(x) $3.3 \times 10^{-6}$ M glutathione (reduced); and
(xi) 1% penicillin/streptomycin/amphotericin B.

21. The construct of claim 20, wherein the serum-free defined chemical media further comprises an additional component selected from the group consisting of platelet derived growth factor in a concentration of from 0.1 ng/ml to 10 ng/ml; L-cysteine in a concentration range of from 0.1 mM to 1 mM, and combinations thereof.

22. The construct of claim 15, wherein the cells are seeded at a density of between 200,000 to 1,000,000 cells/cm$^2$.

23. The construct of claim 15, wherein the medium is replaced every 2-3 days.

24. The construct of claim 1, wherein said construct:
   (a) is seeded with additional cells that grow and are integrated three dimensionally throughout said construct;
   (b) provides mechanical support for said additional cells; and
   (c) provides components for development of said additional cells.

25. The construct of claim 13, wherein said construct:
   (a) is seeded with additional cells that grow and are integrated three dimensionally throughout said construct;
   (b) provides mechanical support for said additional cells; and
   (c) provides components for development of said additional cells.

26. The construct of any one of claim 1, 13, 14, 24 or 25, wherein said fibroblast cells are maintained at a density of about 1,000 cells/mm$^3$ to greater than about 200,000 cells/mm$^3$.

27. The construct of any one of claim 1, 13, 14, 24 or 25, wherein said construct further comprises additional cells, tissue or any combination thereof.

28. The construct of any one of claim 1, 13, 14, 24 or 25, wherein said construct promotes differentiation, dedifferentiation, transdifferentiation or any combination thereof, of cells or tissue either within or in contact with the construct in vitro or in vivo.

29. The construct of any one of claim 1, 13, 14, 24 or 25, wherein said construct promotes cell growth, proliferation, migration and/or acquisition of in vivo-like morphology or any combination thereof, either within or in contact with the construct in vitro or in vivo.

30. The construct of any one of claim 1, 13, 14, 24 or 25, wherein said construct is an ex vivo cell-produced tissue.

31. The construct of claim 24, wherein said additional cells, tissue or combination thereof, comprise:
   (a) stem cells;
   (b) progenitor cells;
   (c) cells or tissue of a connective, epithelial, muscle, nerve or glandular origin; and
   (d) cells of the vascular and/or non-vascular organ origin selected from the group consisting of neuroblastomas, myoblasts, astrocytes, cardiomyocytes, skeletal muscle myoblasts, hepatocytes, chrondrocytes, osteoblasts, fibroblasts, keratinocytes, Schwan cells, nerve cells, glial cells, epithelial cells, endothelial cells, smooth muscle cells, skeletal muscle cells, cardiac muscle cells, stromal cells, mesanglial cells, mesenchymal cells, hematopoietic cells, dendritic cells, immune system cells, neural tissue, hepatic tissue, aortic tissue, venous tissue, capillary tissue, cartilage, bone, muscle, glands, and hair follicles.

32. The construct of any one of claim 1, 13, 14, 24 or 25, wherein said construct provides mechanical support, structural support, nutritional support, developmental support, support for wound repair, or supports the growth or regeneration of cells, tissue, organs, or any combination thereof.

33. The construct of any one of claim 1, 13, 14, 24 or 25, wherein said construct comprises neural cells.

34. The construct of claim 33, wherein the lifespan of said neural cells is extended at least about two-fold compared to neural cells in the absence of the construct.

35. The construct of claim 33, wherein the fragility of said neural cells is reduced compared to neural cells in the absence of said construct.

36. The construct of any one of claim 1, 13, 14, 24 or 25, wherein said construct begins attaching to a site of implantation within about 36 hours, and continues attaching for several days, weeks, or months depending on the site of implantation and degree of immune system activity at the site of implantation.

37. The construct of claim 1, wherein some of said fibroblast cells are genetically engineered.

38. The construct of claim 13, wherein said construct has a tensile strength of at least 200 kilopascals within three weeks of growth.

39. The construct of claim 1, wherein said cellular migration throughout said construct comprises migration of cells from a subject into said construct upon implantation thereof into said subject.

40. The construct of claim 27, wherein said additional cells, tissue or combination thereof, comprise:
   (a) stem cells;
   (b) progenitor cells;
   (c) cells or tissue of a connective, epithelial, muscle, nerve or glandular origin; and
   (d) cells of the vascular and/or non-vascular organ origin selected from the group consisting of neuroblastomas, myoblasts, astrocytes, cardiomyocytes, skeletal muscle myoblasts, hepatocytes, chrondrocytes, osteoblasts, fibroblasts, keratinocytes, Schwan cells, nerve cells, glial cells, epithelial cells, endothelial cells, smooth muscle cells, skeletal muscle cells, cardiac muscle cells, stromal cells, mesanglial cells, mesenchymal cells, hematopoietic cells, dendritic cells, immune system cells, neural tissue, hepatic tissue, aortic tissue, venous tissue, capillary tissue, cartilage, bone, muscle, glands, and hair follicles.

41. The construct of claim 13, wherein some of said fibroblast cells are genetically engineered.

42. The construct of claim 13, wherein said cellular migration throughout said construct comprises migration of cells from a subject into said construct upon implantation thereof into said subject.

43. The construct of claim 25, wherein said additional cells, tissue or combination thereof, comprise:
   (a) stem cells;
   (b) progenitor cells;
   (c) cells or tissue of a connective, epithelial, muscle, nerve or glandular origin; and
   (d) cells of the vascular and/or non-vascular organ origin selected from the group consisting of neuroblastomas, myoblasts, astrocytes, cardiomyocytes, skeletal muscle myoblasts, hepatocytes, chrondrocytes, osteoblasts, fibroblasts, keratinocytes, Schwan cells, nerve cells, glial cells, epithelial cells, endothelial cells, smooth muscle cells, skeletal muscle cells, cardiac muscle cells, stromal cells, mesanglial cells, mesenchymal cells, hematopoietic cells, dendritic cells, immune system cells, neural tissue, hepatic tissue, aortic tissue, venous tissue, capillary tissue, cartilage, bone, muscle, glands, and hair follicles.

44. The construct of claim 14, wherein the fibroblast cells are seeded at a concentration of at least 200,000 cells/cm$^2$ in serum-free defined chemical media.

45. The construct of claim 44, wherein the serum-free defined chemical media comprises base media, basic fibroblast growth factor, epidermal growth factor, dexamethasone, L-3,3',5-triiodothyronine, insulin, selenious acid, and a lipid precursor.

46. The construct of claim 45, wherein the base media is selected from the group consisting of Dulbecco's Modification of Eagle's Medium (DMEM); Ham's F-12 (F12); Ham's F-10 (F10); Iscove's Modification of DMEM (IDMEM); MEDIUM 199; Alpha MEM; Basal Medium Eagle with Earle's BSS; DMEM:F12 1:1 with L-Glutamine; Glasgow's MEM with L-glutamine (GMEM); IMDM with HEPES, with or without L-Glutamine; L-15, without L-Glutamine; McCoy's 5A Modified Medium; Medium 199; MEM Eagle; MEM Eagle-Earle's BSS, with or without L-Glutamine; MEM Eagle-Hanks BSS; NCTC-109; Richter's CM Medium; RPMI 1640 with HEPES; RPMI 1640 and a combination thereof.

47. The construct of claim 46, wherein the serum-free defined chemical media further comprises additional components selected from the group consisting of platelet derived growth factor (PDGF), L-cysteine, Trolox and combinations thereof.

48. The construct of claim 44, wherein the serum-free defined chemical media comprises:
(i) L-ascorbic acid phosphate magnesium salt n-hydrate in a concentration range of from 0.1 mM to 3 mM;
(ii) epidermal growth factor in a concentration range of from 0.002 nM to 2 nM;
(iii) basic fibroblast growth factor in a concentration range of from 0.03 nM to over 3 nM;
(iv) insulin in a concentration range of from 10 µM to 1000 µM;
(v) L-3,3',5-triiodothyronine in a concentration range of from 0.1 nM to 10 nM;
(vi) ethanolamine in a concentration range of from 1 µM to 10,000 µM;
(vii) selenious acid in a concentration range of from 10 nM to 1000 nM;
(viii) Glutamax in a concentration range of from 0 mM to 10 mM; and
(ix) dexamethasone in a concentration range of from 1 nM to 1000 nM.

49. The construct of claim 44, wherein the serum-free defined chemical media comprises a 3:1 ratio of DMEM (high glucose (4.5 g/L); with L-glutamine and sodium pyruvate) and Ham's F12 medium supplemented with the following components:
(i) $4.2 \times 10^{-10}$ M epidermal growth factor;
(ii) $2.8 \times 10^{-10}$ M basic fibroblast growth factor
(iii) $8.6 \times 10^{-5}$ M insulin
(iv) $1.0 \times 10^{-7}$ M dexamethasone
(v) $3.2 \times 10^{-4}$ M L-ascorbic acid phosphate magnesium salt n-hydrate
(vi) $2 \times 10^{-10}$ M L-3,3',5-triiodothyronine
(vii) $10^{-4}$ M ethanolamine
(viii) $3.9 \times 10^{-8}$ M selenious acid
(ix) $4 \times 10^{-3}$ M Glutamax
(x) $3.3 \times 10^{-6}$ M glutathione (reduced); and
(xi) 1% penicillin/streptomycin/amphotericin B.

50. The construct of claim 20, wherein the serum-free defined chemical media further comprises an additional component selected from the group consisting of platelet derived growth factor in a concentration of from 0.1 ng/ml to 10 ng/ml; L-cysteine in a concentration range of from 0.1 mM to 1 mM, and combinations thereof.

51. The construct of claim 44, wherein the cells are seeded at a density of between 200,000 to 1,000,000 cells/cm$^2$.

52. The construct of claim 44, wherein the medium is replaced every 2-3 days.

53. The construct of claim 14, wherein said construct:
(a) is seeded with additional cells that grow and are integrated three dimensionally throughout said construct;
(b) provides mechanical support for said additional cells; and
(c) provides components for development of said additional cells.

* * * * *